(12) United States Patent
Burns et al.

(10) Patent No.: US 10,668,048 B2
(45) Date of Patent: Jun. 2, 2020

(54) COMPOUNDS FOR INHIBITING BACTERIAL GROWTH VIA PHOSPHATIDYLGLYCEROL BINDING

(71) Applicant: Wichita State University, Wichita, KS (US)

(72) Inventors: Dennis H. Burns, Wichita, KS (US); Douglas S. English, Derby, KS (US)

(73) Assignee: Wichita State University, Wichita, KS (US)

( * ) Notice: Subject to any disclaimer, the term of this patent is extended or adjusted under 35 U.S.C. 154(b) by 0 days.

(21) Appl. No.: 16/048,009

(22) Filed: Jul. 27, 2018

(65) Prior Publication Data

US 2019/0029998 A1    Jan. 31, 2019

Related U.S. Application Data

(63) Continuation-in-part of application No. PCT/US2017/015428, filed on Jan. 27, 2017.

(60) Provisional application No. 62/289,027, filed on Jan. 29, 2016.

(51) Int. Cl.

| | | |
|---|---|---|
| *A61K 31/407* | (2006.01) | |
| *C07D 487/22* | (2006.01) | |
| *A01N 43/90* | (2006.01) | |
| *C07D 273/08* | (2006.01) | |
| *C07D 321/00* | (2006.01) | |
| *A01N 43/72* | (2006.01) | |
| *A01N 43/22* | (2006.01) | |
| *A61P 31/04* | (2006.01) | |
| *A61K 31/357* | (2006.01) | |
| *A61K 31/395* | (2006.01) | |

(52) U.S. Cl.
CPC ............ *A61K 31/407* (2013.01); *A01N 43/22* (2013.01); *A01N 43/72* (2013.01); *A01N 43/90* (2013.01); *A61K 31/357* (2013.01); *A61K 31/395* (2013.01); *A61P 31/04* (2018.01); *C07D 273/08* (2013.01); *C07D 321/00* (2013.01); *C07D 487/22* (2013.01)

(58) Field of Classification Search
CPC ........ A01N 43/22; A01N 43/72; A01N 43/90; A61K 31/357; A61K 31/395; A61K 31/407; A61P 31/04; C07D 273/08; C07D 321/00; C07D 487/22
See application file for complete search history.

(56) References Cited

U.S. PATENT DOCUMENTS

| | | |
|---|---|---|
| 2007/0281915 A1 | 12/2007 | Love et al. |
| 2012/0010187 A1 | 1/2012 | Hoffman et al. |
| 2014/0179742 A1* | 6/2014 | Prestwich ............ A61K 31/045 514/333 |

OTHER PUBLICATIONS

Koralegedara et al., The Journal of Organic Chemistry, 2011, 76, 1930-1933 (Year: 2011).*
Alliband et al., The Journal of Organic Chemistry, 2013, 78, 356-362 (Year: 2013).*
International Search Report and Written Opinion in corresponding PCT Application Serial No. PCT/US2017/015428, dated Apr. 7, 2017.
Iyer, et al., "Biophysical characterization and immunization studies of dominant negative inhibitor (DNI), a candidate anthrax toxin subunit vaccine", Hum Vaccin Immunother., Nov. 2013; 9(11): 2362-70.
Thomas, et al., "Carbohydrate modified catanionic vesicles: probing multivalent binding at the bilayer interface", J Am Chem Soc., Apr. 22, 2009; 131(15):5471-7.
Koralegedara, et al., "Initial Structural Studies of Charged Receptors That Bind to Inorganic Phosphate Anion and to an Anionic Phospholipid Found in Bacterial Membranes", J. Org. Chem., 2011, 76 (6), pp. 1930-1933.
Alliband, et al., "Synthesis and Characterization of Picket Porphyrin Receptors That Bind Phosphatidylglycerol, an Anionic Phospholipid Found in Bacterial Membranes", J. Org. Chem., 2013, 78 (2), pp. 356-362.
Alliband, et al., "Developing a targeting system for bacterial membranes: measuring receptor-phosphatidylglycerol Interactions with 1H NMR, ITC and fluorescence correlation spectroscopy", Org. Biomol. Chem., 2015, 13, 502.

* cited by examiner

*Primary Examiner* — Jean P Cornet
(74) *Attorney, Agent, or Firm* — Hovey Williams LLP

(57) ABSTRACT

Antibacterial small molecule compounds, termed liptins, bind to phosphatidylglycerol in bacterial plasma membranes. The small molecule compounds comprise a three-dimensional complementary binding pocket for phosphatidylglycerol, disrupting membrane function in a bacteriostatic or bactericidal manner. Methods of inhibiting bacterial growth and/or treating Gram-positive or Gram-negative bacterial infection using such compounds are also disclosed.

8 Claims, 31 Drawing Sheets

Scheme 1

Scheme 2

MIC: Control   1   2   3   4   5

MIC: Control   5   10   15   20

COMPOUNDS FOR INHIBITING BACTERIAL GROWTH VIA PHOSPHATIDYLGLYCEROL BINDING

CROSS-REFERENCE TO RELATED APPLICATIONS

The present application is a continuation-in-part of International Patent Application No. PCT/US2017/015428, filed Jan. 27, 2017, which claims the priority benefit of U.S. Provisional Patent Application Ser. No. 62/289,027, filed Jan. 29, 2016, entitled PHOSPHATIDYLGLYCEROL RECEPTORS FOR TREATING BACTERIAL INFECTIONS, each of which is incorporated by reference in its entirety herein.

FEDERALLY SPONSORED RESEARCH OR DEVELOPMENT

This invention was made with government support under # P20 GM103418 awarded by the National Institutes of Health. The United States government has certain rights in the invention.

BACKGROUND OF THE INVENTION

Field of the Invention

The present invention relates to small molecules that bind to phosphatidylglycerol for treating bacterial infections.

Description of Related Art

Although antibiotics still remain the first line of defense against pathogenic bacteria, there has been an emergence of many strains of multidrug-resistance (MDR) bacteria. The emerging crisis of bacterial antibiotic resistance is considered to be epidemic. Besides the well-known cases of Gram-positive MRSA and VRSA (*S. aureus*), there is a threat of truly untreatable infections by MDR and pan-drug resistant (PDR) Gram-negative bacteria. Pathogenic strains of *Acinetobacter baumannii, Escherichia coli, Klebsiella pneumonia*, and *Pseudomonas aeruginosa* are now resistant to some (MDR) or all (PDR) antibiotics commonly used to treat these Gram-negative bacteria, such as penicillins, cephalosporins, carbapenems, monobactams quinolones, aminoglycosides, tetracyclines and polymyxins. Extensively drug-resistant strains (XDR) of *Mycobacterium tuberculosis* and carbapenem-resistant (CRE) strains of *Klebsiella pneumoniae* are up and coming threats with high mortality rates of those infected. These MDR pathogens (commonly called superbugs) are a threat to US public health and national security. Indeed, infectious diseases remain the second-leading cause of death worldwide and the third-leading cause of death in the United States. Every year over 23,000 Americans die of nosocomial infections caused by antibiotic resistant bacteria (and with untold billions of dollars added to health care costs). To make matters worse, during this same time period there has been a continuous decrease in the number of newly approved antimicrobial agents for use in the United States, a situation that has become a cause of grave concern to the medical community.

Conventional antibiotics work by disrupting a specific cell target (e.g., cell wall synthesis, protein or DNA synthesis), and bacteria have evolved myriad ways to by-pass the antibiotic's single target, leading to resistance. Due to the rapid rise in bacterial resistance for extant antibiotics, there has been a growing interest in the use of antimicrobial peptides (AMPs) or their mimics as potential antibiotics. Cationic AMPs are able to permeabilize the bacterial cell wall by binding to the negative lipopolysaccharide of Gram-negative bacteria or the teichoic acids and peptidoglycan layer of Gram-positive bacteria via "self-promoted uptake." The outer leaflet of prokaryotic cell inner membrane contain an abundant supply of acidic (anionic) phospholipids, such as phosphatidylglycerol (PG), whereas the outer leaflets of eukaryotic cell membranes are almost exclusively composed of zwitterionic phospholipids. Antimicrobial cationic peptides utilize this difference in lipid head structure to bind to anionic phospholipids of the bacterial membrane. AMP-membrane complex formation is followed by insertion of its hydrophobic portion into the membrane, leading to eventual disruption of the membrane and to cell death. Bacteria have been exposed to such peptides since the dawn of multicellular organisms, yet have shown only limited resistance, likely because targeting a membrane causes a broad range of molecular consequences, which are difficult to overcome by evolving a specific resistance mechanism.

AMPs kill bacteria by disrupting membrane structure. FIG. 1 shows the barrel-stave, carpet and toroidal pore models used to describe the way cationic peptides disrupt the bacterial membrane. More recent studies have shown that the activity of AMPs was not limited to perforation of bacterial membranes. They can also inhibit cellular processes such as DNA/RNA synthesis, protein synthesis, cell division, cell wall synthesis and protein folding, by translocating across the bacterial plasma membrane. The barrel-stave model describes the formation of antimicrobial peptide dimers and multimers after the binding of the peptides to the negatively charged bacterial membrane. This assembly of AMPs penetrates the membrane with their hydrophobic part facing the lipid bilayer and the hydrophilic components forming the internal lumen pores. The assembled peptide molecules inside the pore have a barrel like structure. In the carpet model, the peptides cover the surface of the outer membrane of the bilayer and destroy it with concomitant pore formation. The toroidal pore formation involves the fixation of the inner and outer lipid bilayer by the AMPs Unfortunately, there are many impediments to the use of AMP's as antibiotics, such as high production costs, low bioavailability, degradation by serum proteases and reduced activity by serum salts. Perhaps most importantly, due to limited membrane selectivity, AMPs or their mimics can exhibit host toxicity (systemically, AMPs are contained in, and brought to the site of infection by, cells such as macrophages and neutrophils). Very few AMPs have shown success in clinical trials (not due to lack of activity but for inability to demonstrate an advantage over existing antibiotics), and those cationic antimicrobial peptides presently licensed are for topical use only. These disadvantages have shifted focus from the use of AMPs or their mimics as antimicrobial agents that can be used systemically.

SUMMARY OF THE INVENTION

Described herein are synthetic small molecule compounds, termed "liptins," which are defined herein to refer to small molecules that bind to the PG head group in solution, in synthetic lipid membranes, or in bacterial membranes (plasma or outer) via multifunctional groups correctly aligned with both the phosphate anion portion and glycerol hydroxyl portion of PG. In supramolecular chemistry vernacular, the liptin is the anion receptor and the lipid head-group the ligand. The liptin compounds comprise a scaffold comprising functional groups (aka binding units) arranged to present a three-dimensional binding pocket for PG. More specifically, the liptin scaffold is structured such that it will place binding units in proper orientation to interact with both the phosphate anion portion and glycerol hydroxyl portion of PG head group. This requires correct alignment of binding units along an 8-10 angstrom head group length. Note that the PG head group is positioned orthogonal to the fatty acid hydrocarbon tails. Use of hydrogen bonds in binding units provides for fine control over directionality of interactions within the liptin-PG complex. This enhances the liptin's binding affinity and selectivity for PG. Accordingly, the liptins comprise functional groups capable of hydrogen bonding with neutral (glycerol hydroxyls) and/or charged oxygens (phosphate anion portion) in PG.

As such certain embodiments of the invention are concerned with antibacterial small molecule compounds that bind to PG in bacterial plasma membranes (see FIG. 1B). These small molecule compounds generally comprise a central scaffold and a plurality of functional groups, at least one functional group for binding to an anion, and at least one functional group for glycerol binding. As such, the scaffold and functional groups cooperatively form a three-dimensional complementary binding pocket for PG.

For example, liptin structures preferably comprise at least two sets of binding units, with one set designed to bind to the anion portion of the PG head group and one set that binds with the neutral glycerol hydroxyls. Usually this means the stronger of the two hydrogen-bonding binding units will interact with the anionic phosphate head group portion (more effective stabilization of charge), especially if the liptin scaffold has positively charged ammonium groups (Coulombic interactions). Thus, the liptins present complementary and multifunctional binding pockets for the PG lipid's head group aligning correctly with the phosphate anion portion and (neutral) glycerol head group of PG. For example, the working examples demonstrate that the four pickets on meso-phenyl rings of a porphyrin scaffold, or on the ortho-para substituents on a linked bis-phenol scaffold, when appropriately functionalized, formed a complementary binding pocket to the PG lipid's multifunctional head group. Thus, the liptins are the first target-based designed small molecule capable of tight binding to a lipid anionic head group at a membrane interface using non-covalent interactions. The liptin design results in high binding affinity, unlike AMPs that use non-specific Coulombic interactions to bind to bacterial plasma membranes. Also unlike AMPs that permeate the bacterial membrane, certain liptins according to the invention appear to stay strongly bound to the lipid head group.

The liptins disrupt various physiochemical properties of plasma membranes. For example, upon bonding, the liptin 3e-PG complex dramatically alters the effective lipid head group size and charge from mono-anionic to tetra-cationic. This, in turn, alters the physical chemistry and disrupts the homeostasis of the lipidome, with lowered cell viability appearing to be attributable to depolarization and/or loss of bacterial plasma membrane function.

Also described herein are antibacterial compositions comprising a bacteriostatic or bactericidal amount of an antibacterial small molecule compound according to embodiments herein, dispersed in a pharmaceutically-acceptable carrier.

These compounds and compositions are useful in inhibiting bacterial growth, killing bacteria, as well as in treating bacterial infection in a subject suffering from an infected area. The methods generally comprise contacting the infected area or the bacteria with a therapeutically-effective amount of an antibacterial small molecule compound according to embodiments described herein. Thus, described herein is a new therapeutic modality to treat bacterial infections, and would save lives for those with infections, particularly those that are resistant to conventional antibiotics. Due to the general nature of the membrane damage caused by liptins, the rate of resistance occurrence is expected to be low. Liptins have a high potential to be developed into highly efficient antimicrobials of broad spectrum.

Further, fluorescent liptins that bind the PG head group and alter membrane properties have utility as molecular tools to study the dynamics of lipid-lipid and lipid-protein interactions essential for bacterial membrane integrity and function. This could help identify the roles of lipid-lipid and lipid-protein interactions in bacterial membrane integrity and function, interactions that are difficult to target with current tools. As importantly, the development of supramolecular recognition principles for targeting many kinds of membrane lipids would provide a new set of biophysical tools to enhance basic understanding of heterogeneous membrane function.

BRIEF DESCRIPTION OF THE DRAWINGS

FIG. 11 D is a photograph of MIC experiments with *S. faecalis* cultures;

DETAILED DESCRIPTION

Figure 1A:
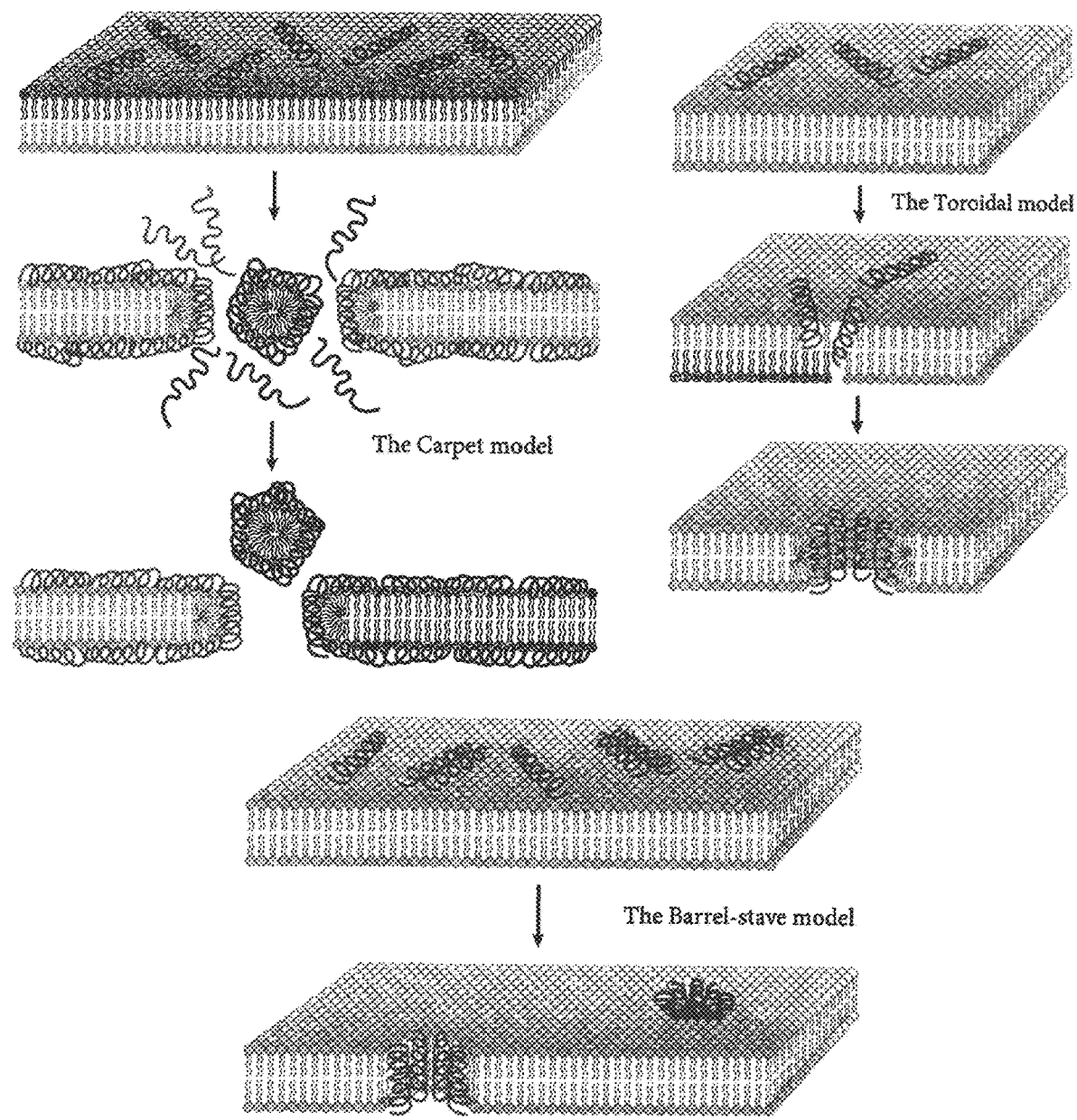
FIG. 1A is a representation of three models of pore formation by AMP molecules Brogden, K. A., Antimicrobial Peptides: Pore formers or metabolic inhibitors in bacteria? Nat. Rev. Microbiol., 2005. Vol. 3: p. 238-250.
Figure 1B:
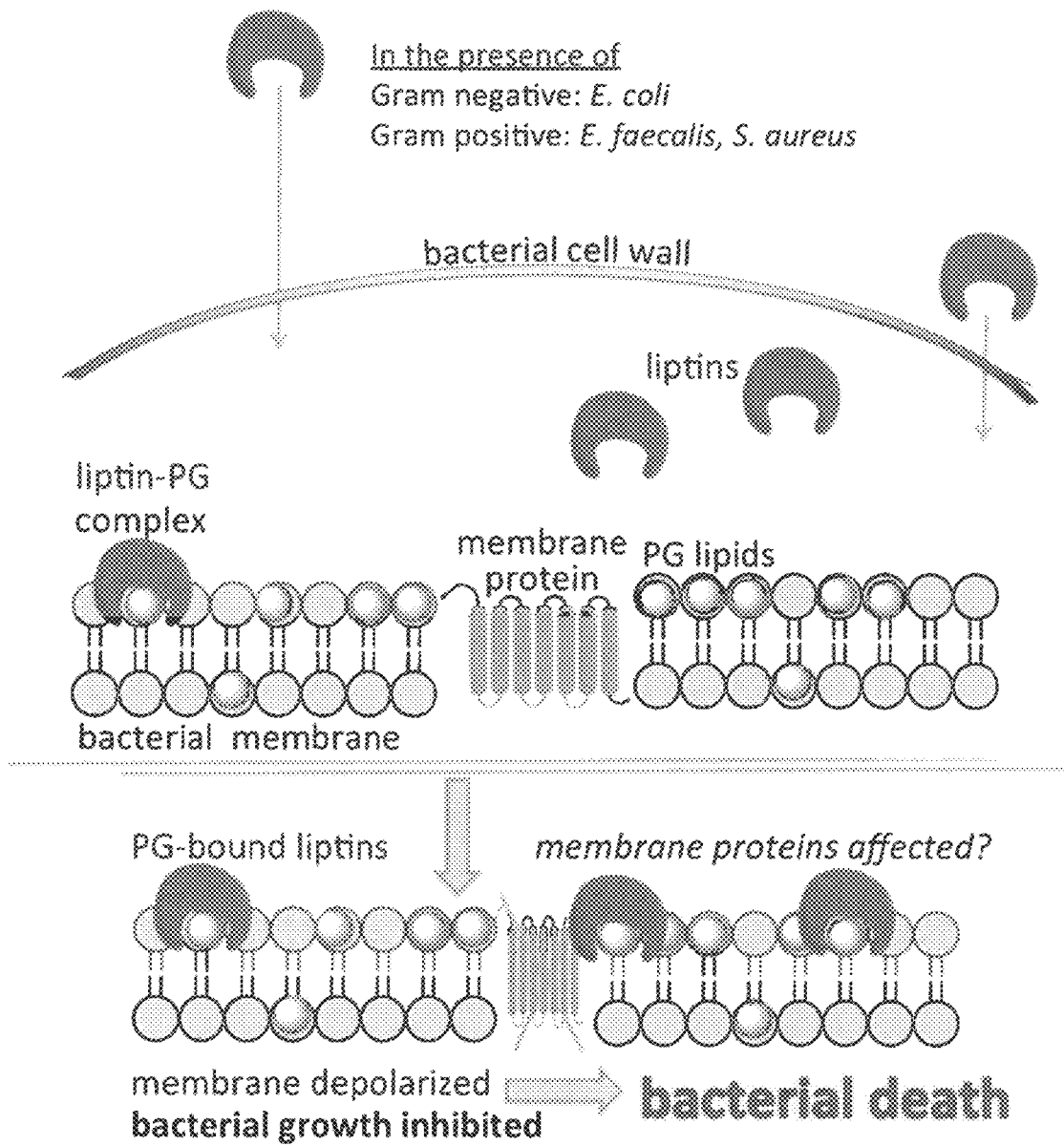
FIG. 1B is a cartoon illustration of the mechanism of action of the liptins on PG.

The present invention is concerned with new therapeutic modalities for treating bacterial infection and represents a new approach to antimicrobials. The major phospholipid components of both Gram-negative and Gram-positive bacterial membranes are anionic cardiolipin (CL) and phosphatidylglycerol (PG) and zwitterionic phosphatidylethanolamines (PE), while the outer leaflets of eukaryotic cell membranes are almost exclusively composed of zwitterionic phospholipids. In prokaryotes, the relative abundance of PE and PG can vary between species and with life-cycle and environmental factors, but PG is always present in significant quantities and makes up approximately 20-30% of the lipid content in *E. coli*, 12% in *B. subtilis* and up to 50-60% in *Staphylococcus aureus* and *Streptococcus pneumonia*. Recent work indicates that lipid homeostasis appears crucial for specific protein placement within cytosolic membrane hyperstructures and hence for cellular processes in the cell life cycle. Thus, disrupting the lipidome may well disrupt several important cellular processes.

The present invention is broadly concerned with the new class of small molecule compounds referred to herein as liptins, having antibacterial (aka bacteriostatic, and/or bactericidal) activity against Gram-negative and Gram-positive bacteria. In this disclosure, the term "small molecule" refers to synthetic compounds in which the molecular weight does not exceed 2000 grams per mole. These liptins are at least bacteriostatic, and in some cases can be bactericidal. The term "bacteriostatic" as used herein means that the liptin at least stops or slows down bacterial reproduction (biostatic), while not necessarily killing the bacteria. In other words, when the liptin is removed, the bacteria may resume growth and/or proliferation. In some cases, at higher concentrations (>10 µM), the liptin is preferably bactericidal, killing the bacteria. At lower concentrations (10 µM or less), the liptins can be used in methods of inhibiting bacterial growth, and in some cases as part of treating bacterial infection.

These liptins are small molecule compounds that bind anionic PG lipids in bacterial plasma membranes, disrupting the membrane, and resulting in inhibition of bacterial cell growth, or bacterial cell death. As described herein, the liptins have a three-dimensional complementary binding pocket for the PG head group, and thus a binding affinity and selectivity for bacterial PG. Thus, the liptins comprise H-bonding functional groups that can bind to an anion, in this case, the phosphate anion portion of the PG headgroup. There can be more than one of these groups on a liptin, and liptins can be acyclic or cyclic. In one or more embodiments, the liptin is based upon one of two scaffolds: a porphyrin ring; or a macrocyclic system comprising two linked phenol rings, which preferably contain one or more ammonium groups for positively-charged hydrogen bonding. There are a number of different donor groups for anions, with the list expanding greatly in recent years. Classic H-bonding donor groups also include, without limitation:

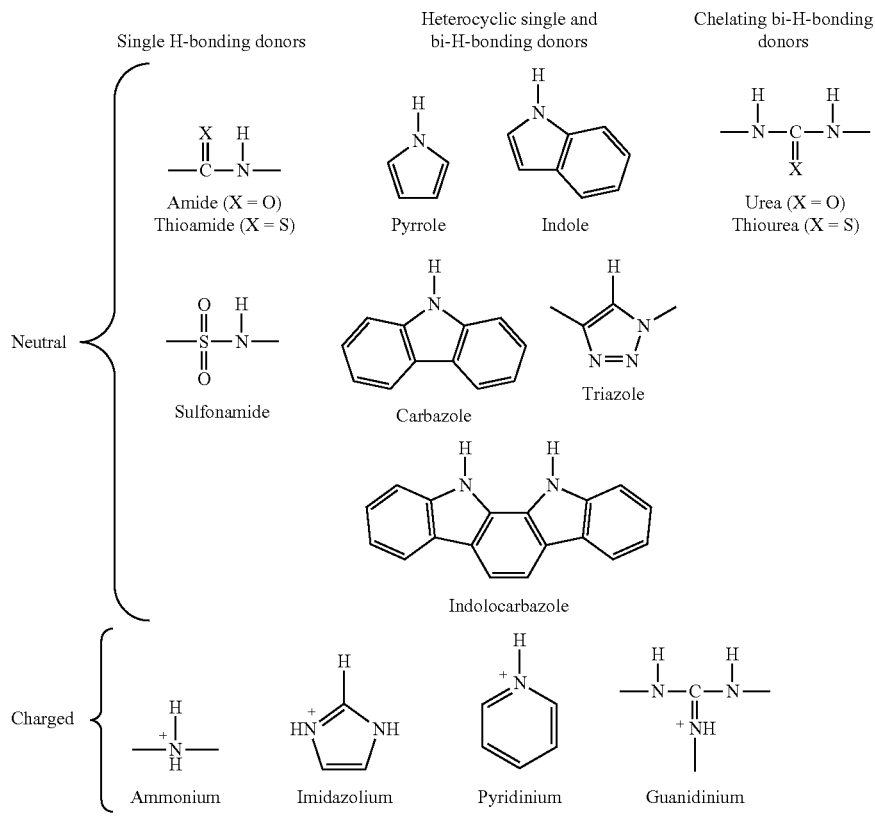

This list is not exhaustive, but provides good examples.

Advantageously, the small molecules also bind to the glycerol portion of the PG headgroup found in the bacterial plasma membrane. Exemplary functional groups for glycerol binding include, without limitation groups that are both H-bond donors and H-bond acceptors with hydroxyl groups for formation of neutral H-bonds (e.g., —OH, —CONH$_2$, —CONHOH, —NHCONHR'—CO$_2$H). Also, ammonium groups may form charged hydrogen-bonds with the oxygen atom in the glycerol headgroup. Thus, overall the small molecule structure can be neutral or charged.

Exemplary compounds for use as liptins include:

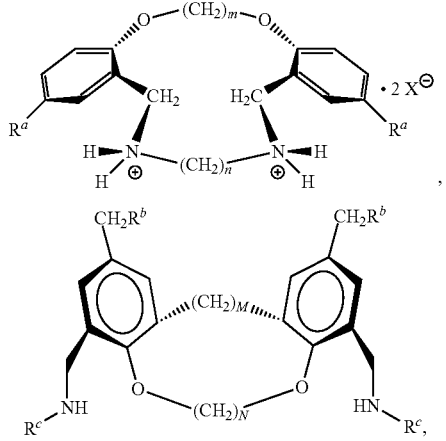

-continued

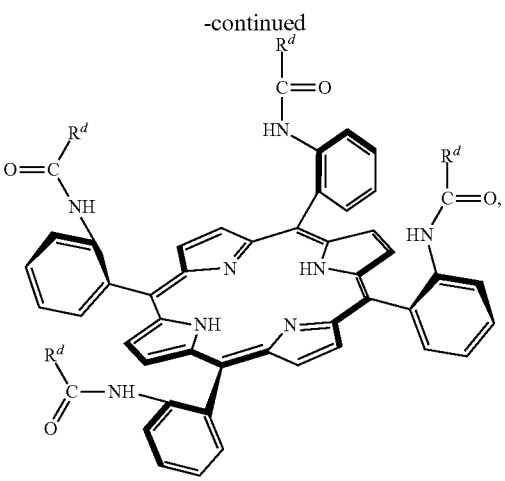

and combinations thereof, where:
X$^-$ is PF$_6^-$, CF$_3$CO$_2^-$, or any other anionic counter ion, such as halogen anions (e.g., Cl$^-$ or Br), phosphate anions (e.g., H$_2$PO$_4^-$), organophosphate anions (e.g., R$^e$HPO$_3^-$), sulfate anions (e.g., HSO$_4^-$), organosulfonate anions (e.g., R$^e$SO$_3^-$), or other carboxylate anions (e.g., CH$_3$CO$_2^-$ or R$^e$CO$_2^-$), where each R$^e$ is an alkyl or aryl group.
m is 3, 4, or 5;
n is 3, 4, 5, or 6;
M is 3, 4, or 5;
N is 1, 2, 3, or 4;
each R$^a$ is —(CH$_2$)$_2$CONHC$_6$H$_{13}$, —CH$_2$CONHC$_6$H$_{13}$, —(CH$_2$)$_2$CONH(CH$_2$)$_y$NHCOCH$_3$, —(CH$_2$)$_2$CONH $(CH_2)_yNHCONH(CH_2)_yCH_3$, $-(CH_2)_2CONHOH$, or $NHNHCONH(CH_2)_yCH_3$, where each y is 1, 2, 3, or 4;

each $R^b$ is $-CH_2CH_2OH$, $-CH(OH)CH_2OH$, or $-CH_2CO_2NHOH$;

each $R^c$ is $-CONHPh$, $(2H)^+ +X^-$, or $-C(=NH^+)NHR'$, where R' is an alkyl (e.g., $C_1$-$C_8$ alkyl) or aryl group; and each $R^d$ is $-COHN$-alkyl (preferably C3-C8 alkyl), $-CONHCH_2CH_2OCH_2C_6H_5$, $-CONHCH_2CH_2OH$, $-CONH(CH_2CH_2O)_3CH_2CH_3$, $-CONHCH_2CH_2CH_3$, $-CH_2NH_3^+X^-$, $-CH_2NH_2^+CH_2C_6H_5$, $-CH_2NH_2^+CH_2CH_2CH_3$, $-CH_2NH_2^+CH_2(CH_2)_4CH_3$, $-CH_2CH_2(OCH_2CH_2)_yCH_3$, $-CH_2Ph$, or $-CH_2R''$, where R'' is 2-(aminomethyl)-5-methylphenol or 5-(aminomethyl)-2-methylphenol, wherein any of the foregoing alkyl or aryl groups may be substituted or unsubstituted.

Thus, the liptins for use in the invention contain within their complementary binding pocket multiple hydrogen bonding functional groups able to align correctly and specifically with the PG lipid's phosphate anion portion and the glycerol hydroxyl groups. These liptins bind to the PG displayed on the surface of bacterial plasma membranes with high affinity and selectivity, and the resulting liptin-PG complex formation has been shown to inhibit bacterial growth in both Gram-negative and Gram-positive bacteria. This result is most likely from the depolarization of the plasma membrane upon liptin complexation with PG. A synthetic advantage to the liptin porphyrin structure is the inherent symmetry of the four pickets that are capable of alignment with the two different sets of lipid functional groups. NMR studies have been used to determine binding motifs within the liptin-PG complex. Using the thermodynamics of binding (determined from NMR and ITC techniques) associated with particular liptin-PG complex structures enables us to iteratively change liptin design to enhance liptin affinity for PG.

Compositions according to the invention comprise a bacteriostatic or bactericidal amount of the liptin dispersed in a pharmaceutically-acceptable carrier. In general, the compositions may comprise from about 0.1 to about 95% of the liptin, based upon the total weight of the composition taken as 100%, and preferably from about 0.5 to about 50% of the liptin. The amounts will depend upon the desired use, the particular agent used, and the particular carrier(s) selected. The term carrier is used herein to refer to a base, diluent, excipient, vehicle, or the like, in which the liptin may be dispersed for administration or application. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained.

A pharmaceutically-acceptable carrier would naturally be selected to minimize any degradation of the liptin or other agents and to minimize any adverse side effects in the subject, as would be well known to one of skill in the art. Pharmaceutically-acceptable ingredients include those acceptable for veterinary use as well as human pharmaceutical use, and will depend on the route of administration. Exemplary carriers include aqueous solutions such as normal (n.) saline (~0.9% NaCl), phosphate buffered saline (PBS), sterile water/distilled autoclaved water (DAW), aqueous dextrose solutions, aqueous glycerol solutions, ethanol, normal allantoic fluid, various oil-in-water or water-in-oil emulsions, dimethyl sulfoxide (DMSO), petroleum jelly, cocoa butter, cottonseed oil, olive oil, sodium pyruvate, vitamin E, white petrolatum, white wax, stearyl alcohol, cholesterol, mineral oil, ceryl ester wax, sodium lauryl sulfate, propylene glycol, polyethylene glycol, and the like.

Other ingredients may be included in the composition, such as adjuvants, other active agents, preservatives, buffering agents, salts, other pharmaceutically-acceptable ingredients, including residual amounts of ingredients used in pharmaceutical manufacturing.

In some embodiments, the bacteriostatic compositions of the invention consist essentially or even consist of the liptin dispersed in a carrier. In some embodiments, the compositions are substantially free of additional bactericidal or bacteriostatic agents, where the term "substantially free" means having no significant amount of that component purposefully added to the composition to import a certain characteristic (as contrasted with intentional ingredients listed above), it being understood that trace amounts of incidental elements and/or impurities may sometimes find their way into a desired end product (e.g., due to contamination from incidental additives or through contact with certain processing and/or holding equipment). In some embodiments, the compositions are substantially free of antibiotics, antimicrobial peptides, alkaline earth metals, and the like. As liptins are synthetic molecules, such ingredients if present, preferably represent no more than 0.05%, preferably less than 0.005%, and more preferably less than about 0.001% by weight of the composition taken as 100% by weight in total.

Methods of inhibiting bacterial growth are also described herein. The methods generally comprise contacting bacteria with the liptin. In one or more embodiments, the liptin is in a composition, which is then contacted with the bacteria. In one or more embodiments, the liptin is administered or applied to a subject suffering from a bacterial infection. Thus, methods of treating bacterial infection in a subject suffering from a bacterial infection are also described herein. The methods generally comprise contacting an infected area of the subject with a liptin described herein. In one or more embodiments, the liptin is in a composition, which is then contacted with the area. An "infected area" of the subject, as used here, may refer to a defined site of local infection, such as a wound, but is also used to refer to a systemic infection characterized by the presence of pathogenic microorganisms or their components in the blood or tissues and organs other than primary infected area of the subject. Regardless, the infection is due to Gram-negative or Gram-positive bacteria. Thus, in one or more embodiments, methods of the invention comprise directly and/or topically applying a liptin to an infected area of the subject. In one or more embodiments, methods of the invention comprise systemically administering a liptin to the subject, for example, remote from the infected area, such as by introducing a liptin into the blood circulation system of the subject.

Various routes of administration can be used depending upon the particular carrier and other ingredients used. For example, topical administration may involve rubbing, dabbing, or otherwise applying liptins to the infected area, followed by an appropriate dressing, gauze, bandage, or other covering, if desired. The liptins can also be injected intramuscularly, subcutaneously, intradermally, or intravenously using a needle and syringe, or a needleless injection device. The liptins can also be administered mucosally, such as intranasal administration. Oral administration is also contemplated, provided that the liptins are formulated appropriately for passage through the gastrointestinal system (e.g., in an enteric-coated dosage form). In some embodiments, the methods described herein are useful for reducing the effects, severity, or morbidity of bacterial infection, as described herein.

Methods of the invention will utilize a therapeutically effective amount of liptin in inhibiting bacterial growth or treating bacterial infection. As used here, a "therapeutically effective" amount refers to the amount that will elicit the biological or medical response of a tissue, system, or subject that is being sought by a researcher or clinician, and in particular elicit some desired inhibitory effect as against the bacterial infection by reducing bacterial growth and/or killing bacteria. Thus, a therapeutically amount of liptin includes bacteriostatic as well as bactericidal amounts of liptin. One of skill in the art recognizes that an amount may be considered therapeutically "effective" even if the condition is not totally eradicated or prevented, but it or its symptoms and/or effects are improved or alleviated partially in the subject.

In some embodiments, the liptins are provided in unit dosage form in a suitable container. The term "unit dosage form" refers to a physically discrete unit suitable as a unitary dosage for use. Each unit dosage form may contain a predetermined amount of liptin (and/or other active agents) in the carrier calculated to produce the desired effect. In other embodiments, the liptins can be provided separate from the carrier (e.g., in its own vial, ampule, sachet, or other suitable container) for on-site mixing before administration to a subject. A kit comprising the liptins is also disclosed herein. The kit further comprises instructions for administering the liptins to a subject.

Our studies with Gram-negative and Gram-positive bacteria and studies of protein overexpression in *E. coli* suggest liptin-complex formation changes the plasma membrane physical properties. Liptin binding interrupts lipid head group interactions, altering membrane fluidity, or disrupting lipid microdomains and therefore protein localization and function. Additionally, liptin-PG complex formation has been shown to depolarize the plasma membrane, which will lead to the observed inhibition of bacterial replication and growth.

The liptins used in the invention have broad spectrum action against both Gram-negative and Gram-positive bacteria. A key advantage of liptins in this class is sparing of the endogenous microbiome. In some embodiments, these liptins exhibit bacteriostatic effects that the immune system capitalizes on through normal clearance methods. Unlike invading pathogens, endogenous flora are protected from immune responses due to peripheral tolerance mechanisms. Therefore, even as these liptins do impede bacterial growth universally, immune cells will not clear endogenous organisms.

In one or more embodiments, the liptin has a minimum inhibitory concentration (MIC) of from about 1 to about 4 preferably between 1 and 4 µM. It will be appreciated that the MIC of the liptins are stated in micromolar (µM), because the liptin molecule is relatively large and weighs nearly twice as much as most conventional antibiotics. Accordingly, the lowest concentration of liptin that inhibits growth of bacteria is more precisely provided as a unit of concentration in the micromolar range. The liptins would be effective against one or more of the following pathogenic microbes: *Acinetobacter baumannii, Escherichia coli, Staphylococcus aureus* (including MRSA), *Enterococcus faecalis, Mycobacterium smegmatis, Streptococcus pneumoniae, Streptococcus pyogenes, Streptococcus mitis, Streptococcus mutans, Streptococcus bovis, Klebsiella pneumoniae, Pseudomonas aeruginosa, Enterococcus faecium, Staphylococcus epidermidis, Staphylococcus haemolyticus, Salmonella typhimurium, Bacillus subtilis, Neisseria meningitides, Neisseria gonorrhoeae, Haemophilus influenzae*, and the like.

The invention provides a significant advancement in the art, of a completely new therapeutic modality to treat bacterial infections, whereby formation of the liptin-PG complex at the plasma membrane by itself disrupts bacterial cellular processes inhibiting bacterial growth and/or causing bacterial cell death, without the need for any adjuvants, or other antibiotic agents. Liptin-PG complex formation, by changing membrane properties, causes some or perhaps many membrane proteins, such as transporter proteins, to function less efficiently or perhaps not at all, or keep membrane protein complexes necessary for function from forming, or inhibit transporter functions. For example, any deleterious effects on a bacteria's SecYEG or TAT secretory systems (both composed of multi-protein assemblies), ion channels or bacterial two component systems, all found in the cytosolic membrane, could inhibit growth, replication, interfere with bacterial virulence mechanisms (i.e., prevent pilus or biofilm formation, or slow or stop the production of bacterial toxins and effectors), and in general lower the bacteria's vitality. The action of the liptins on fundamental features, such as bacterial membrane function prevents selection pressure for the emergence of resistant strains. In a broader sense, the liptins can also be used to study the organizing principles in membrane heterogeneity, and the interactions of bacterial membrane protein hyperstructures and lipid microdomain structures.

Figure 2A:
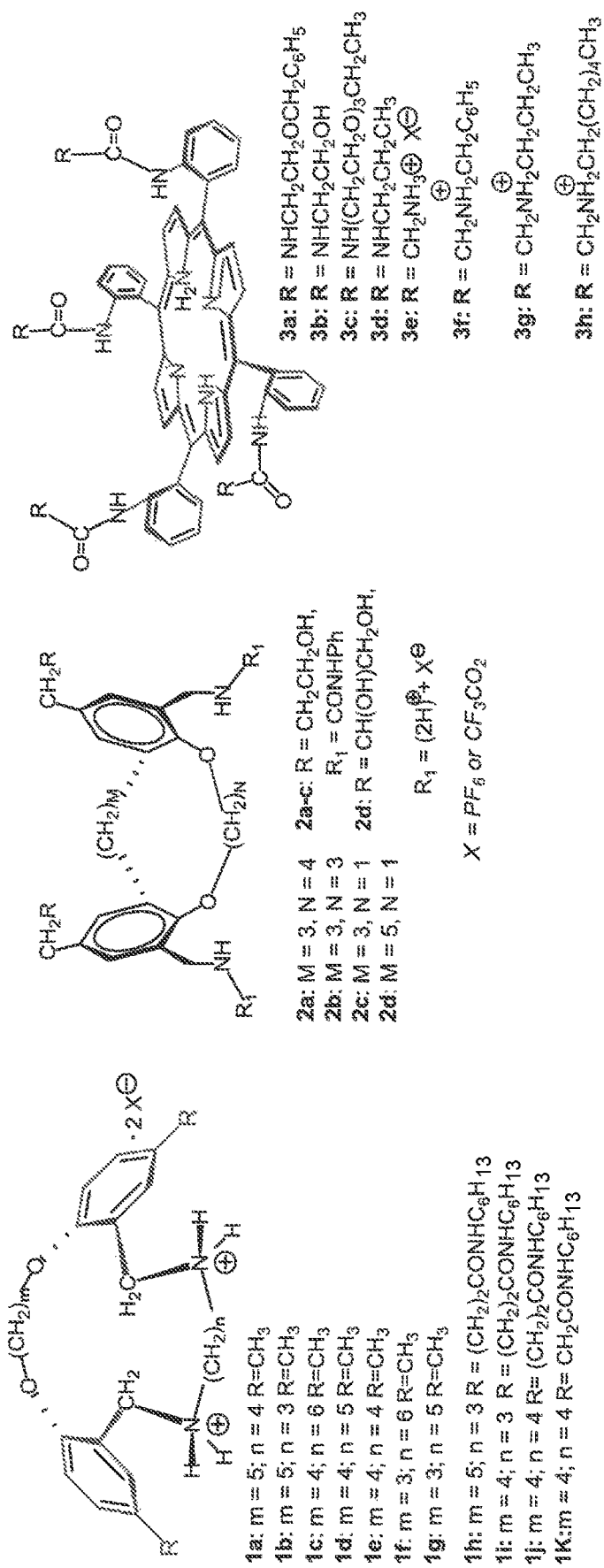
FIG. 2A is an illustration of representative families of multifunctional small molecules (liptins) that have been synthesized and which bind selectively to PG.
Figure 3:
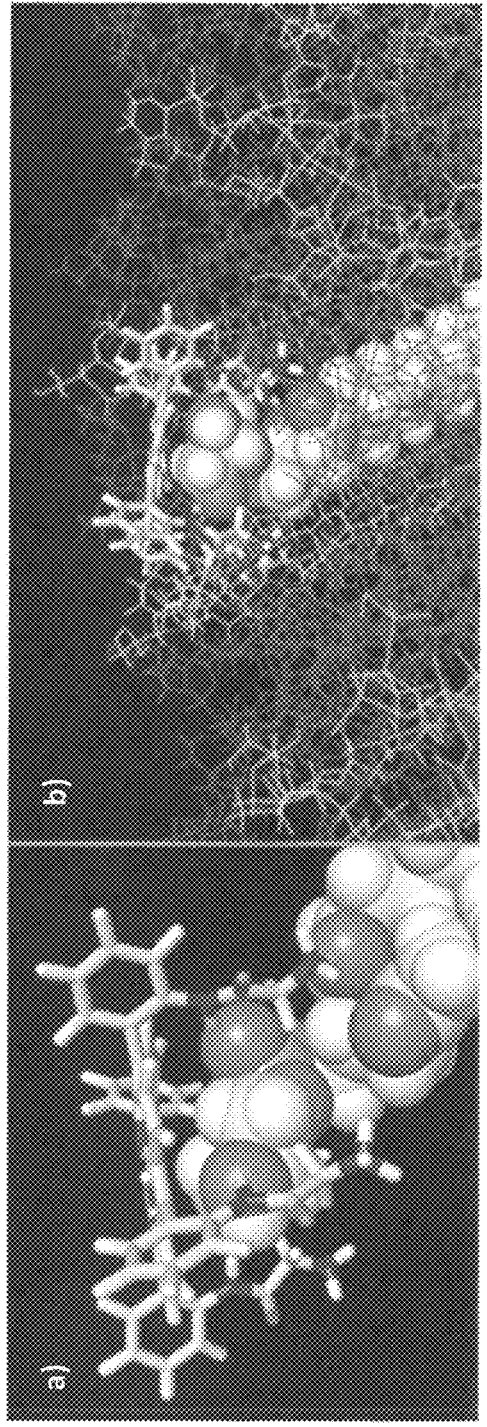
FIG. 3 is a Molecular Dynamic simulation with a porphyrin-based molecule that binds selectively to PG involving a heterogeneous bilayer lipid patch.

As noted, the liptin/PG binding significantly perturbs lipid-lipid interactions by altering the PG head group charge and size and leads to measurable changes in membrane physical properties (such as the fluidity and viscoelasticity of the membrane) and, ultimately, the viability of cell membrane function. FIG. 3 shows Molecular Dynamic simulations with a porphyrin-based liptin (3e, see FIG. 2A) involving a heterogeneous bilayer lipid patch in explicit water solvent illustrates how our small molecule liptin caps the lipid head group.

Specifically, the bound PG lipid is illustrated as a space-filling representation, while other PG and PE lipids are in stick representation. Liptin 3e is shown in a stick representation in both FIGS. 3A and 3B. All water molecules have been removed for clarity.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention. It is important to note that with these following examples we show 1) liptins are the first target-based designed small molecule capable of tight binding to a lipid anionic head group at a membrane interface using non-covalent interactions, and 2) completely different structures (3e and 1h-k), that only have in common the target PG lipid head group, show similar in vitro effects via a new mechanism of action. The data establishes a proof of concept that liptin-PG complex formation (by itself) results in highly bacteriostatic and/or bactericidal action by disrupting plasma membrane homeostasis, notwithstanding differences in the particular liptin structures.

The first two examples clarify the structural requirements for a liptin binding pocket that exhibits multifunctional complementarity for the phosphatidylglycerol (PG) head group. Notably, the outer leaflet of prokaryotic plasma membrane contains an abundant supply of the anionic lipid PG, while the outer leaflets of eukaryotic cell membranes are almost exclusively composed of zwitterionic phospholipids. Thus, a liptin that binds to PG will selectively target the bacterial plasma membrane. Three families of liptins were prepared as presented in Example 1. Example 1 illustrates the synthesis and characterization of new liptins which can increase the binding affinity and selectivity for phosphatidylglycerol. The structures of the liptin-PG complexes were studied in solution, with mixed-lipid liposomes and synthetic vesicles, and with efflux studies to determine membrane leakage with liposomes, as presented in Example 2. Importantly, the studies of a porphyrin liptin at a membrane interface (Example 2) of a synthetic vesicle doped with PG show similarities to the liptin's solution binding motif and high selectivity of binding to PG because of binding pocket complementarity. Example 3 details how short-term and long-term bacterial growth and viability is affected by liptin 3e when it is introduced to both Gram-negative and Gram-positive bacterial strains, and the determination of MICs for Gram-negative and Gram-positive bacteria. Example 3 shows that liptin 3e, simply by binding to PG in the plasma membrane, depolarizes both the $S.$ $aureus$ and $E.$ $coli$ plasma membrane. Example 3 details the in vitro studies that measure the effects on development of bacterial resistance to a porphyrin picket PG liptin with both Gram-negative and Gram-positive bacterial strains by serial passage studies. Example 4 is an examination of toxicity of liptin 3e on eukaryotic hepatic cells. Example 5 is an initial examination of toxicity of liptin 3e on erythrocytes. Example 6 provides the additional characterization of liptins 3e-h and 1h-k. Included is an examination of how the binding of liptins 3e-h and 1h-k to PG liposomes affects membrane permeability via efflux experiments with carboxy-fluorescein dye leakage. Included are additional bacterial growth curves of Gram-negative and Gram-positive bacteria in BHI enriched medium with one inoculation of liptin 3e. Included are minimum inhibition concentrations and minimum bactericidal concentrations of liptins 1h-k in Muller Hinton culture with Gram-negative and Gram-positive bacteria. Included are Live Dead staining results of liptins 1h and 1k with Gram-negative and Gram-positive bacteria. Included are plasma membrane depolarization studies with liptins 1h and 1k with $E.$ $coli$ and $S.$ $aureus$. Included are scanning electron micrographs of $E.$ $coli$ and MRSA showing the comparison between treated and untreated bacterial cells with liptin 1k. Included is a molecular dynamics study of liptin 1h and a PG lipid patch showing the binding motif of the liptin 1k to PG in a membrane. Example 7 shows a toxicity study of eukaryotic HeLs (vaginal carcinoma) and A549 (lung epithelial carcinoma) cells with liptins 1h and 1k.

Example 1

In a project designed to develop targeting systems for bacterial membranes, we have generated novel families of small molecules (termed liptins) that are the first to show good complementarity with the PG head group (Koralegedara et al., J. Org. Chem. 2011, 76, 1930-1933; Alliband et al., J. Org. Chem. 2013, 78, 356-362; Alliband et al., Org. Biomol. Chem. 2015, 13, 502-512). Specifically, we have synthesized liptin's binding pocket with suitably spaced functionality to bind and correctly align with two different sets of lipid functional groups, the phosphate anion portion and the neutral glycerol hydroxyl groups. We demonstrated that the four pickets on meso-phenyl rings of a porphyrin scaffold, or the ortho-para substituents on two types of linked bis-phenol scaffolds, when appropriately functionalized, formed a complementary binding pocket to the PG lipid's multifunctional head group. Thus, the liptins are the first target-based designed small molecules capable of tight binding to a lipid anionic head group at a membrane interface using non-covalent interactions.

(1.1) Liptin Syntheses.

Figure 2B:
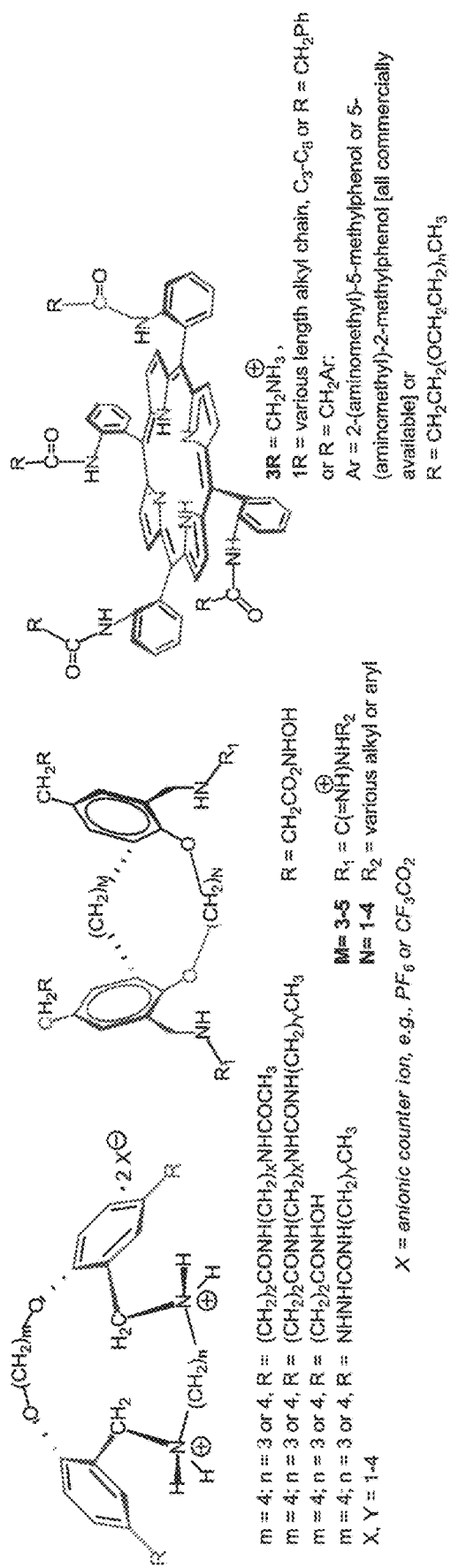
FIG. 2B is an illustration of additional proposed families of multifunctional small molecules (liptins) for selective binding to PG.

The preparations of liptins 1a-g and 3a-e (FIG. 2A) has been described in previous work. The detailed syntheses of 1h-k, 2a-d, and 3f-h (FIG. 2A) are presented below. Additional compounds have been contemplated, as illustrated in FIG. 2B. All liptins are furnished with binding-pocket (positively charged) ammonium and (neutral) amide or hydroxyl hydrogen-bonding groups able to align and bind with the phosphate anion portion and neutral glycerol portion of the PG head group, respectively. Molecular dynamics simulations using a lipid patch illustrated (FIG. 3) that the 3e-PG complex configuration at the membrane interface has its pickets pointing towards the membrane. This indicates that elaboration of all or some of the porphyrin pickets, as seen in 3f-h with groups able to insert into the membrane, will increase the complexation entropy via loss of solvent molecules and reduce complexation enthalpy via favorable interaction with lipid tails.

(1.1.1) Preparation of Bis-Phenol Liptins 1h-1k and Proposed Elaborations.

Figure 4:
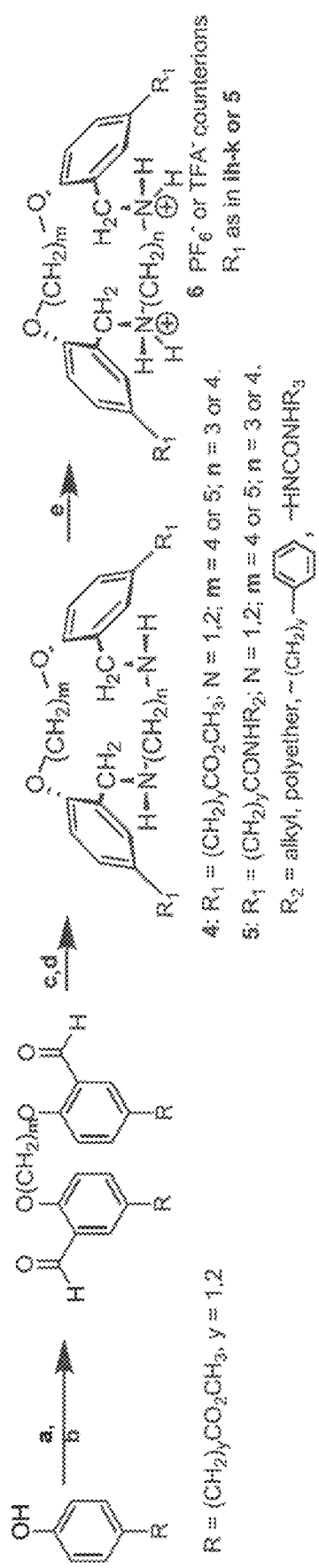
FIG. 4 is a reaction Scheme 1 for synthesis of liptins with bis-phenol-based scaffolds.

The binding of liptins 1a-g, R=CH$_3$, to PG in solution has been described, as part of previous work directed towards developing PG liptins as targeting moieties. Since then, we have replaced the liptin's methyl para-substituent with acetic or propanoic amide units for binding to the glycerol hydroxyl groups. Modeling indicates this is the correct length for the amides to hydrogen bond with the PG hydroxyl groups while the ammonium groups hydrogen bond to the phosphate anion portion. We have synthesized bis-phenols 1a-g (and will prepare additional bis-phenols 6) by starting with a phenol ring that contains the commercially available para-acetic or -propanoic ester (Scheme 1, FIG. 4). Coupling the di-ester 4 with a primary amine (compounds 5) followed by protonation furnished charged liptins 1a-g (or will furnish 6) able to H-bond with glycerol hydroxyl groups. Amide formation via the methyl ester proved to be straightforward using $La(Tf)_3$ as catalyst. Bis-amidation could also be accomplished by de-esterification followed by amidation of the di-acid with a primary amine using well known coupling reagents. Additionally, we can prepare other functionalized para-R groups with commercially available N-alkylhydrazinecarboxamides coupled to the bis-acid with TBTU to furnish liptins with semicarbazide urea functional groups to bind to the PG glycerol groups. Or, using commercially available ω-aminoalkylamides or ω-aminoalkylureas we can prepare the para-amide with additional amide or urea groups to interact with neighboring lipid head groups once the liptin forms a complex with membrane-bound PG.

(1.1.2) Preparation of Bis-Phenol Liptins 2a-2d and Proposed Elaborations.

Figure 5:
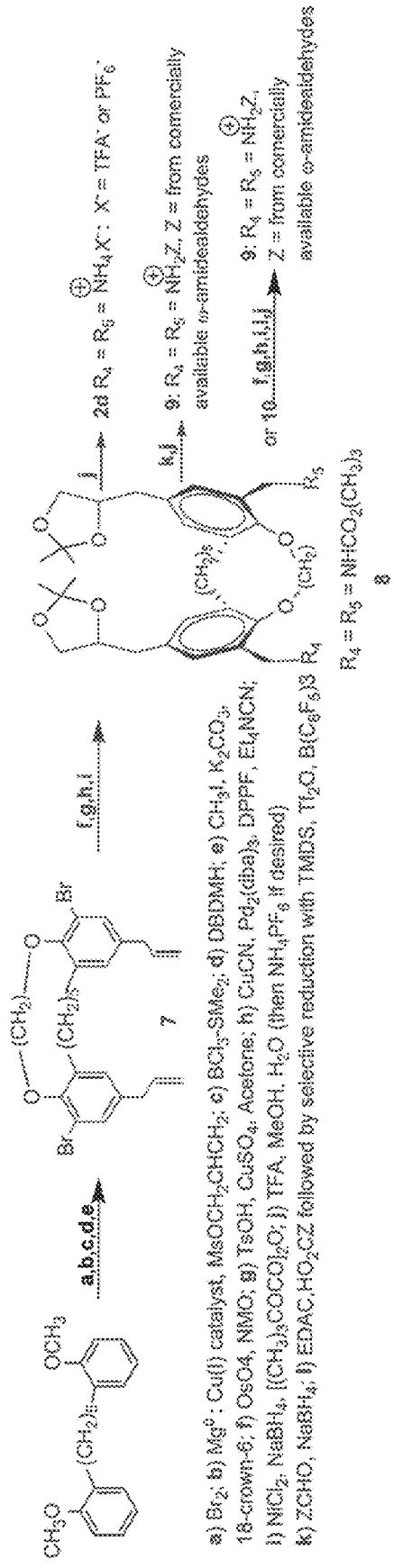
FIG. 5 is a reaction Scheme 2 for synthesis of a second class of liptins with bis-phenol-based scaffolds.

Liptins 2a-2d (FIG. 2A) have been prepared and characterized, but not published. However, example syntheses of several precursors required for the preparation of liptins 2a-2d, via precursors 7-8, utilizing soluble copper catalyst developed in our laboratory to couple the two aromatic rings and to elaborate the ring structure is based upon our previous experience, as is our methodology to efficiently ureidoalkylate the bis-phenol intermediates (FIG. 5). Prior research has shown that urea liptins 2a or 2b exhibited no significant binding to PG, whereas 2c exhibited a rather modest binding constant for PG ($K_a \leq 10^2$ M$^{-1}$) in DMF solution. In contrast, inorganic phosphate anion bound more tightly to 2c ($K_a = 10^3$ M$^{-1}$), indicating the anion binding unit with one methylene unit linking the two phenolic oxygens was a complementary fit for phosphate anion. By adding two additional methylene groups to the bridge linking the two rings [i.e., now $(CH_2)_5$, 2d], the size of the pocket better accommodates the PG head group, leading to increased liptin 2c-PG binding with a $K_a \approx 500$ M$^{-1}$ in DMF. To further increase binding affinity, we changed the 3-hydroxypropane para-substituent into a 2,3-propane diol para-substituent (seen in 8 prepared from 7, FIG. 5). This increased the number of possible interactions between the liptin and the PG glycerol hydroxyls and reduced possible conformational constraints in the binding pocket when only two hydroxyl groups are present. FIG. 5 shows the synthetic pathway to prepare 2d with a ring linkage of five methylene units (same pathway can be used for four or six methylene units). Importantly, we changed the phosphate anion-binding urea groups to the stronger hydrogen-binding ammonium groups as shown in FIG. 5. Elaboration of 2d can be accomplished from reductive amination of an aldehyde with the ortho-methylamines to form 9. In this way hydrogen-bonding groups can be added to interact with neighboring lipid head groups. A second route would replace carbamate formation (during nitrile reduction) with amide formation (10) followed by mild, selective hydrosilation-deoxygenation of the amide to furnish 9. Additionally, the ortho-methylamines can be transformed into multiple, stronger hydrogen-bonding groups, such as guanidinium functional groups.

(1.1.3) Preparation of Elaborated Liptins 3f-h and Proposed Elaborations. Modification of Porphyrin Pickets with Membrane Insertion Units.

The structure of the entire picket in porphyrin liptins 3a and 3c was found to influence the enthalpy and entropy of lipid binding, suggesting that PG liptins elaborated with groups able to insert into membranes to interact with the lipid (and not just the lipid headgroup) would increase the liptin's overall membrane affinity and selectivity with the goal of lowering MIC's as determined from bacterial experiments. The synthetic manipulations employed allow us to determine experimentally how iterative changes in the lipid-liptin complex structure affect the $K_a$, enthalpy and entropy of non-covalent interactions ($^1$H NMR, FCS and ITC experiments).

A homologous series of alkyl additions to the pickets (above the ammonium groups) is intended to provide stabilizing van der Waals' interactions between the insertion unit and lipid tail, along with different insertion depth of picket structures within the membrane. Polyether insertion units allow for dipole-dipole and hydrophobic interaction, and aromatic insertion units with appropriately substituted ring substituents allow for hydrogen bonding interactions with the fatty acid ester groups. It may prove preferable to elaborate only one or two (cis) pickets as membrane insertion units to allow the same glycine ammonium binding motif for PG seen in 3e while still providing membrane insertion units.

Figure 6:
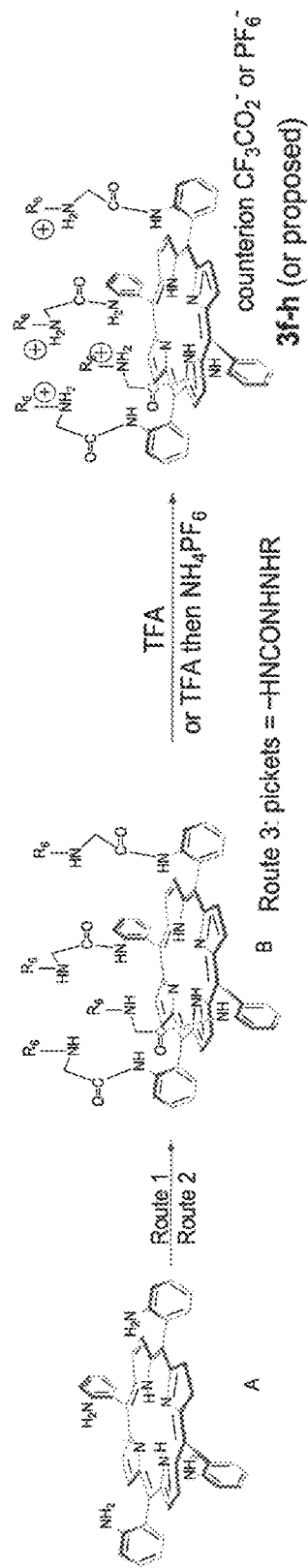
FIG. 6 is a reaction Scheme 3 for synthesis of liptins with porphyrin-based scaffolds.

Three potential routes to prepare porphyrins with extended pickets (3f-g are proposed) are presented in FIG. 6). Route 1 involves reductive amination of the uncharged glycine picket with an aldehyde. Route 2 involves amidation of the meso-phenylamines via addition of chloroacetyl chloride followed by the $S_N2$ addition of amines to the resultant alkyl chloride (examples of alkyl, polyether, or benzyl amines are shown in Scheme 1). Route 2 is capable of furnishing a more diverse set of pickets, and modeling has shown that the use of the aryl amines shown in Scheme 1 would position their phenolic OH groups to allow for hydrogen bonding with the lipid's fatty acid ester groups. At the present time, porphyrins 3f-h have been furnished using Route 2. Route 3 involves the transformation of the meso-phenylamines into phenylisocyanates, followed by the addition of a substituted hydrazine (prepared from an aldehyde and hydrazine to form the hydrazone followed by reductive amination or with commercially available hydrazines) to furnish a semicarbazide group whose nitrogen can be charged (FIG. 6). The urea portion of the semicarbazide would provide additional strong hydrogen-bonding sites for the glycerol hydroxyl groups. Porphyrin 3e that contains TFA counterions is quite water soluble, and we expect similar results with modified porphyrins.

(1.1.4) Elaboration of Porphyrins's Meso-Phenyl Rings: Liptin-PG Complex Interactions with Neighboring Lipid Head Groups.

Figure 7:
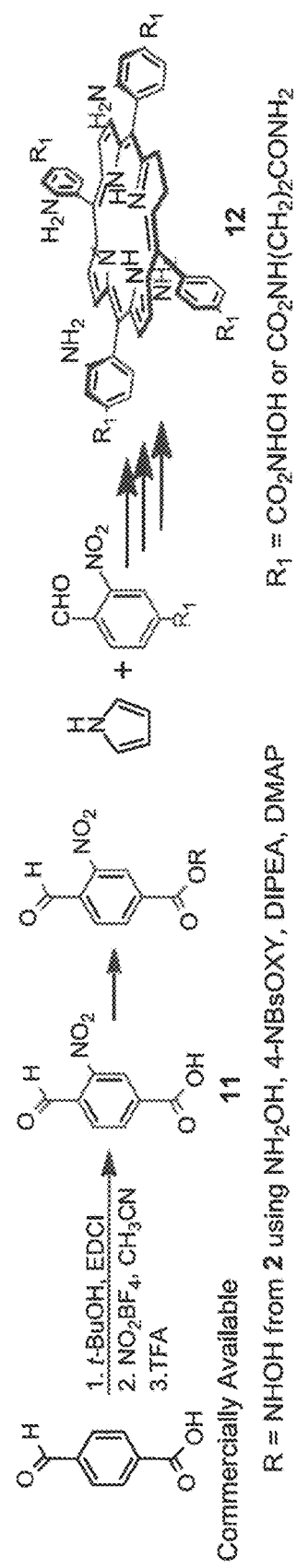
FIG. 7 is a reaction Scheme 4 a second class of liptins with porphyrin-based scaffolds.

A second method to increase overall membrane affinity is to prepare liptin porphyrins that not only bind to a specific PG lipid, but also engage in secondary interactions with neighboring PG or phosphatidylethanolamine (PE) lipids found in the bacterial plasma membrane. Modification of para-positions on the porphyrin's meso-phenyl rings with hydroxylamine or amide groups would provide additional binding units for neighboring lipid head groups via 1) H-bonding to adjacent lipid anionic phosphate groups, or 2) head group interaction with adjacent PE ammonium hydrogens or PG hydroxyl groups. Two possible para-substituents are hydroxamic acid or bis-amide groups that able to hydrogen bond to neighboring lipid head groups, whose synthetic pathway is shown in FIG. 7 (benzaldehyde precursor 11 and porphyrin 12). Use of the Adler method to furnish porphyrin A (FIG. 6) could lead to lower yields, and a Lindsey approach reacting 5-aryldipyrromethanes with substituted aromatic nitrobenzaldehydes, or via N-tosyl imines, may prove a longer but more fruitful approach. Also, polar meso-substituents will provide water solubility to the liptins, perhaps important if the extended pickets add hydrophobicity. As with liptins in general, such multidentate liptins will change the viscoelasticity of the plasma membrane and thereby interfere with lipidome homeostasis and perhaps interfere with membrane protein dynamics and function.

both the enthalpy and entropy associated with binding, for the TBA phosphatidylglycerol anion with a 1:1 stoichiometry of binding. The use of organic solvents allowed the determination of binding motif using $^1$H NMR. Spectroscopic studies showed that liptins with the preorganized (ortho-ring substituted) ammonium or urea groups found in compounds 1 or 2, or the four ammonium or urea pickets on the porphyrin ring as in 3, bound to the PG lipid's phosphate anion group via hydrogen bonds. Additionally, published spectroscopic data showed that the PG's glycerol hydroxyl group hydrogen-bonded with 3e's amide group, while unpublished data showed PG's glycerol hydroxyl group interacted with 2d' s bis-hydroxyl functional groups.

TABLE 1

| PG Liptin | 1b | 1e | 2c | 2d | 3a | 3c | 3e |
|---|---|---|---|---|---|---|---|
| $K_a$ (M$^{-1}$) | 2 × 10$^2$ | 2.5 × 10$^2$ | 4.2 × 10$^2$ | 1.7 × 10$^4$ | 2.1 × 10$^3$ | 3.7 × 10$^3$ | 2.8 × 10$^3$ |
|  | (±6 × 10$^1$) | (±4 × 10$^1$) | (±6 × 10$^1$) | (±1.4 × 10$^3$) | (±1 × 10$^2$) | (±4.5 × 10$^2$) | (±1.0 × 10$^3$) |
| ΔH (kcal mol$^{-1}$) |  |  | −1.4 |  | −2.8 | −1.2 | 0.7 |
|  |  |  | (±0.02) |  | (±0.07) | (±0.04) | (±0.09) |
| ΔS e.u. |  |  | 8 |  | 6 | 12 | 18 |

(1.1.5) Multiple Porphyrin Arrays.

Figure 8:
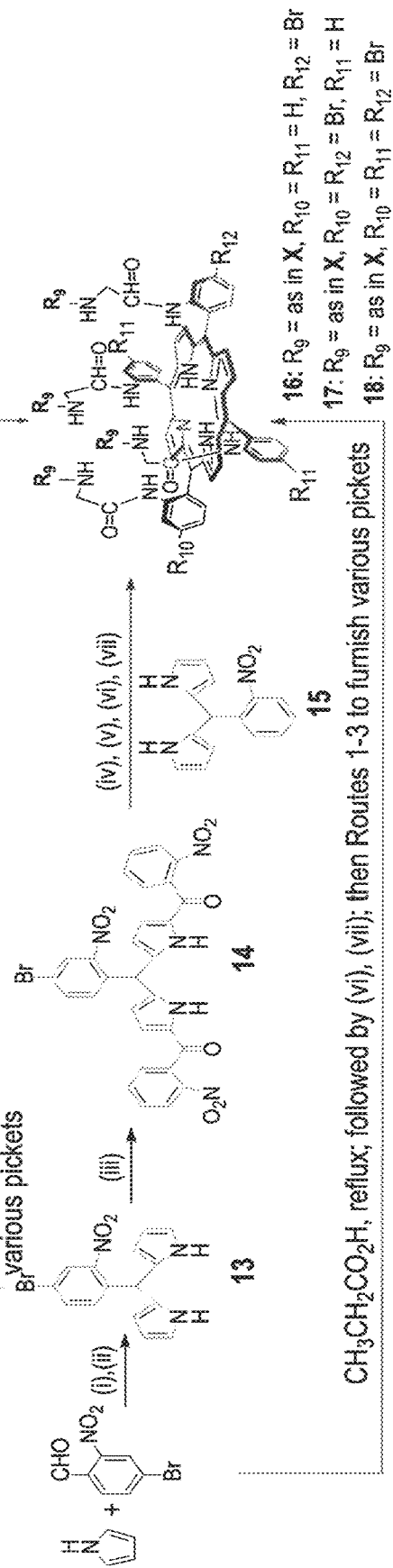
FIG. 8 is a reaction Scheme 5 of a third class of liptins with porphyrin-based scaffolds.

If results from the above experiments suggest that higher affinity and selectivity for PG liptins is desirable (to lower bacterial MIC), then we can undertake the synthesis of liptins with two or more PG binding units. Assuming the correct linker size, complex stability should be increased due to the well-known chelate effect. Synthetic routes to multiporphyrin arrays have been well established. While there are no reports of (covalently bound) multiple picket porphyrin arrays, we will prepare picket porphryins with the proper functionality to furnish a picket porphyrin dimer, trimer, or larger array via covalent assembly. The linker coupling the two porphyrins will need to be 8-10 angstroms or longer in length to allow for two bound PG lipids to reside side-by-side in the membrane. Coupling of the two porphyrin rings after the pickets have been prepared will avoid potential problems with the formation of an all a-atropisomer of multiple meso-phenylamines and the preparation in one reaction of multiple pickets. The preparation of a dimer will be 'proof of concept' that the picket dimer can be synthesized from porphyrin 16 using standard Sonogashira coupling in the preparation of multiple porphyrin arrays. Note that depending on the synthetic pathway, porphyrins can be prepared with one, two (5,15: trans), or with four bromophenyl groups (porphyrins 17,18) for linking via Sonogarshira coupling of alkynes to the bromophenyl position (FIG. 8).

Synthetic lipid vesicles with varying ratios of anionic and zwitterionic lipids will be utilized in binding studies with these elaborated porphyrin liptins to examine the affect porphyrin arrays have on lipid organization and membrane structure. In vesicles, these effects can be measured with differential scanning calorimetry and fluorescence polarization.

Example 2

(2.1) Determination of Liptin-PG Binding in Solution.

The lipid binding ability of liptins 1-3 (FIG. 2A) have been investigated in solution using isothermal titration calorimetry (ITC) and/or $^1$H NMR. Stoichiometry of binding was accomplished with Job plots using $^1$H NMR. Table 1 details liptin-PG association constants, and ITC data shows Results from ITC (errors in parentheses) for liptin-lipid complexes that exhibit 1:1 binding stoichiometry (1b, 1e, 2d from NMR titrations). Liptins 1b, 1e, 2c, 2d, 3a, 3c in DMF/5% CHCl$_3$; 3e in 50% DMSO, 45% CHCl$_3$, 5% CH$_3$OH.

To examine in detail the structural requirements needed for 1's scaffold to bind the phosphate anion portion of PG, we prepared a family of small molecules whose linkages between the two phenolic oxygens and two benzyl amines were of different lengths. In this way small molecule PG-liptins were constructed to support various binding motifs and maximize the entropic contribution to complexation. Because both the lipid head group and liptin were charged and studies were conducted in polar solvents, it was expected that complex formation would be entropy driven. As reported, liptins 1b and 1e both bound to PG, with association constants of 2-2.5×10$^2$ M$^{-1}$, and using ITC (results not shown) we determined that complex formation was indeed entropy driven.

The scaffolding in liptin 2 contained either neutral (urea, 2c) or charged (ammonium, 2d) groups to bind with the phosphate anion portion in PG, and hydroxyl groups on the para substituents to bind the glycerol hydroxyl groups. Liptin 2d, with the charged ammonium groups and four para-hydroxyl groups bound strongly to PG in 1:1 binding stoichiometry. Its association constant of approximately 2×10$^4$ M$^{-1}$ is almost two orders of magnitude stronger than the binding constant of 2c, showing that charged ammonium hydrogens bonds and two sets of bis-hydroxyl groups were important to efficient binding of PG in solution.

$^1$H NMR and isothermal titration calorimetry (ITC) were used to determine liptin 3's PG binding stoichiometry, liptin-lipid complex structure, binding constant, and associated thermodynamic properties of complexation in solution. Thermodynamic properties determined from ITC showed that liptin 3e-PG complex formation was entropy driven, while PG-binding for the neutral liptins 3a and 3c were driven by both enthalpy and entropy. All three exhibited association constants of 2-4×10$^3$ M$^{-1}$ in organic solution. $^1$H NMR spectroscopy detailed the binding motif of liptins 3a, 3c, and 3e, and showed that the PG headgroup was positioned just above the porphyrin ring with the liptin's urea or ammonium pickets aligned correctly to bind both the phosphate anion portion. In porphyrins 3a and 3c the urea groups interacted with the hydroxyl portion of PG, while in 3e the amide groups interacted with the hydroxyl portion.

Data for new liptins 1h, 1i, and 3f are shown in Table 2. The increase in $K_a$ from 1b to 1h is greater than one order of magnitude. We infer that 1h's para-amide functional group (as opposed to a non-hydrogen bonding para-methyl group in 1b) is hydrogen-bound to the PG hydroxyl group and results in a more thermodynamically stable complex. The association constants determined from ITC or NMR titrations for liptin 1h were very similar. However, the two liptins 1b and 1h were measured in different solvent systems due to different solubility requirements, which may also contribute to the large difference observed in association constants. The lower association constant for liptin 3f compared to liptin 3e may be due to steric bulk of the pickets which may make it more difficult for the PG head group to fully access the binding pocket. $^1$H NMR spectroscopy shows that the picket's amide groups of 3f are not involved in hydrogen bonding to the PG's glycerol group, and that the PG head group lies farther above the ring than in the 3e-PG complex.

TABLE 2

| PG Liptin | 1h | 1i | 3f |
|---|---|---|---|
| $K_a$ (M$^{-1}$) | $4.6 \times 10^3$ ($\pm 3.8 \times 10^2$) | $1.5 \times 10^3$ ($\pm 4.3 \times 10^2$) | $2.8 \times 10^3$ ($\pm 1.0 \times 10^3$) |
| $\Delta H$ (kcal mol$^{-1}$) | 0.6 ($\pm 0.03$) | 3.7 ($\pm 2.1$) | |
| $\Delta S$ e.u. | 19 | 27 | |

Results from ITC or NMR titrations (errors in parentheses) for liptin-lipid complexes that exhibit 1:1 binding stoichiometry for PG (3f from NMR titrations). Liptins 1h and 1i 40% DMSO, 60% CHCl$_3$, 3f in 20% DMSO, 80% CHCl$_3$.

(2.2) Determination of Liptin 3e Affinity and Selectivity of Binding PG at the Membrane Interface.

The porphyrin 3e was used to examine the liptin's affinity and selectivity for PG when PG was present as part of a membrane bilayer. In this example, fluorescence correlation spectroscopy (FCS) was used to measure the fraction of liptin bound to surfactant vesicles or liposomes containing a known amount of PG. This approach is fast, reliable and accurate, and is possible when the liptin is a stable fluorophore, as in the case of 3e.

FCS results are evaluated by treating the time dependent fluorescence intensity acquired from a dilute solution of the liptin using a focused laser beam as the excitation source. Temporal fluctuations in the fluorescence intensity are a result of the diffusion of the liptin through the focused laser beam. When the liptin binds to a vesicle, its apparent diffusion coefficient decreases by two orders of magnitude. The data is analyzed using a correlation analysis that results in an autocorrelation decay, GO, and presented in FIG. 9.

Figure 9:
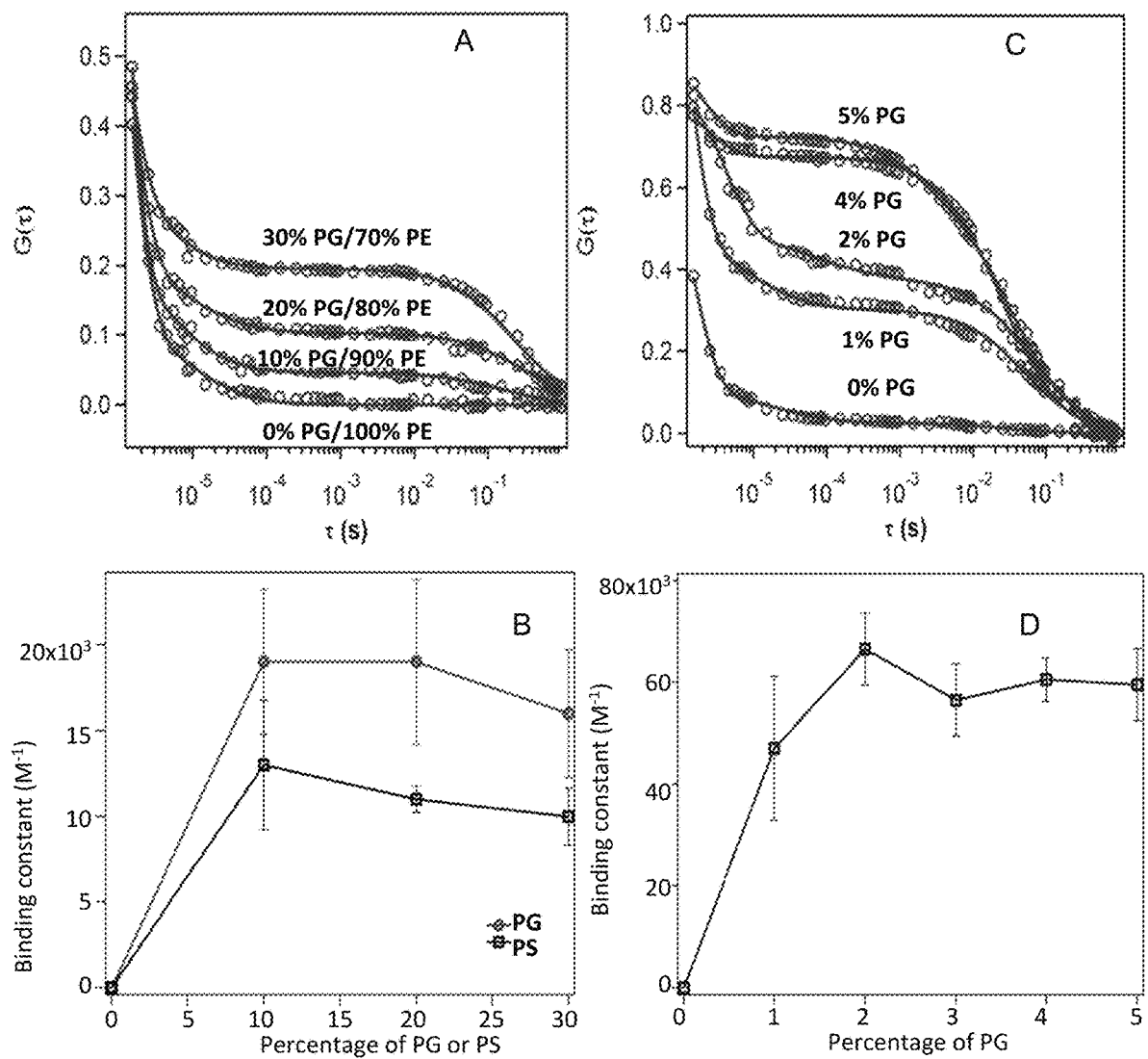
FIG. 9 is a representation of autocorrelation decays for liptin 3e membrane-bound to PG in (A) liposomes and (C) surfactant vesicles containing varying amounts of PG, with binding constants for each in (B) and (D), respectively.

FIG. panels 9A and 9C contain examples of autocorrelation decays for liptin 3e in with liposomes (FIG. 9A) and surfactant vesicles (FIG. 9C) containing varying amounts of PG. Specifically, FIG. 9 illustrates an autocorrelation analysis of liptin 3e binding to PG-doped membranes of liposomes and positively-charged surfactant vesicles. A) Autocorrelation decays for liptin with varying percentages of PG in PE liposome. B) Binding constant values as a function of PS and PG in PE liposome. C) Autocorrelation decays for liptin with varying percentages of PG in positively-charged surfactant vesicles. D) Binding constant of liptin with varying percentages of PG in positively-charged surfactant vesicles. In both examples, a slowly-decaying component becomes more prevalent in G(t) as the amount of PG present in the bilayer increases. The slowly decaying component arises from the slower diffusion of 3e, when bound to vesicles. Note that the decay of G(t)consists of a single fast component when the samples contain 0% PG. For a quantitative treatment, the autocorrelation decays are fit to a function that gives the binding fraction of the liptin in solution. In FIGS. 9A and 9C, the markers are the experimental data and the solid lines are the fits that determine the fraction of liptin bound, f. This quantity is then used to calculate the binding constant:

$$K = \frac{[\text{bound receptor}]}{[\text{free receptor}][\text{free } PG]} = \frac{f}{(1-f)\left(\frac{[PG]}{2} - [R]f\right)}$$

where [R] is the total concentration of liptin, and it has been assumed that half of the PG is located on the membrane inner leaflet and thus not available for binding. Binding constants are given in FIGS. 4B and 4D. Lipid vesicles containing 10-30% PG all exhibited a $K_a=10^4$ for 3e.

Our FCS studies revealed the following important discoveries:

1) PG binding affinities at the membrane interface are similar to those found for 3e in solution, on the order of $10^4$ M$^{-1}$.
2) Binding is specific for PG and is not attributed merely to pure Coulombic interactions; since no binding is observed in vesicles that contain anionic headgroups that differ from PG. Negligible binding of the liptin was observed when the surfactant vesicle contained no PG and the only anionic component was sodium dodecylbenzenesulfonate (SDBS), see FIG. 9D. When the vesicle contained as little as 1% of PG and 35% SDBS, the binding constant increased from negligible to $4.7 \times 10^4$ M$^{-1}$
3) Analysis of binding constants for 3e with lipid vesicles formed from binary mixtures of either PG or phosphatidylserine (PS) with phosphatidylethanolamine (PE) showed that binding is selective for PG over the PS (also anionic). Note that 30% PG: 70% PE is an approximation of an *E. coli* membrane composition.

Figure 10A:
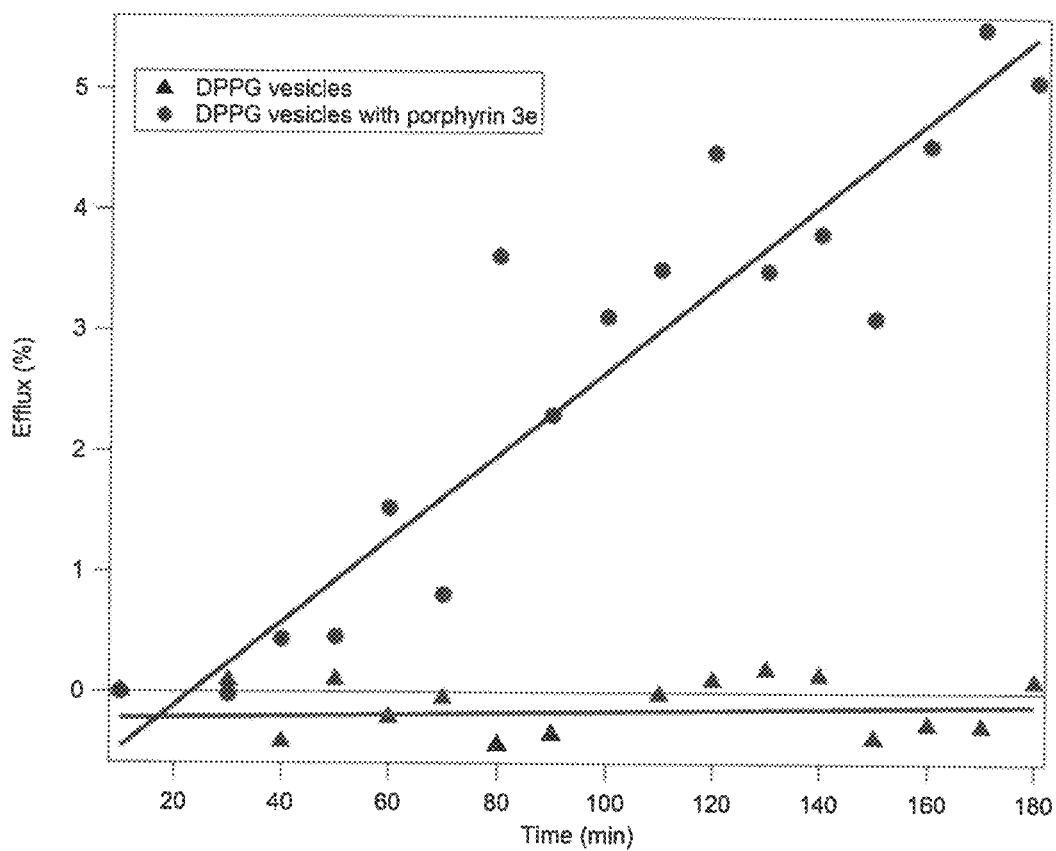
FIG. 10A is a graph from the initial efflux experiments in synthetic lipid vesicles showing a comparison of efflux data for carboxyfluorescein dye from vesicles with pure PG in the presence and absence of liptin 3e. Additional efflux experiments with liposomes containing a 20/80 mixture of PG and phosphatidylethanolamine to better simulate a bacterial membrane are shown in FIGS. 19A-F with liptins 3e-h and 1h-k.

(2.3) Physiochemical Effect of 3e Complexation with PG in Synthetic Lipid Vesicle (FIG. 10A).

Liptin/bilayer interactions were evaluated using conventional efflux measurements. These experiments make use of the self-quenching fluorescence of carboxyfluorescein. At relatively high concentrations (ca. 50 mM) the fluorescence from carboxyfluorescein is diminished by approximately 70% due to intermolecular interactions.

To perform efflux experiments vesicles were prepared by rehydrating a film of pure DPPG with a 50 mM solution of carboxyfluorescein in buffer. The solution was then extruded through a polycarbonate membrane with 200 nm pore size. The solution was extruded repeatedly for a series of seven passes after which the resulting vesicle-containing solution was purified on a size exclusion chromatography column packed with Sephadex50. After chromatography, the solution consists of vesicles filled with 50 mM dye solution suspended in dye-free buffer solution. Under these conditions, as the dye leaves the vesicles by efflux, fluorescence intensity increases. Monitoring the fluorescence intensity over time provides a measure of the rate at which dye crosses the membrane and an indication of the "leakiness" of the vesicle bilayer. Efflux can be expressed as % Efflux by the following expression:

$$\% \text{ Efflux} = \frac{F(t) - F_O}{F_\infty - F_O}$$

where $F_O$ is the fluorescence intensity corresponding to the initial sample when efflux first begins and $F_\infty$ is the intensity after efflux is complete and is determined by rupturing the vesicles by the addition of a small amount of concentrated detergent. F(t) is the fluorescence intensity measured as the efflux occurs.

FIG. 10A shows a comparison of efflux data for carboxyfluorescein from vesicles prepared with pure PG in the presence and absence of the liptin. At room temperature, there is no measureable efflux from the vesicles during the course of the three hour experiment. This changes dramatically when liptin 3e is added and efflux is 5% complete after three hours. The large increase in efflux rate indicates that liptin binding at the interface increases the permeability of the membrane.

Example 3

(3.1) Bacterial Experiments: Determination of Minimum Inhibitory Concentration (MIC).

Figure 10B:
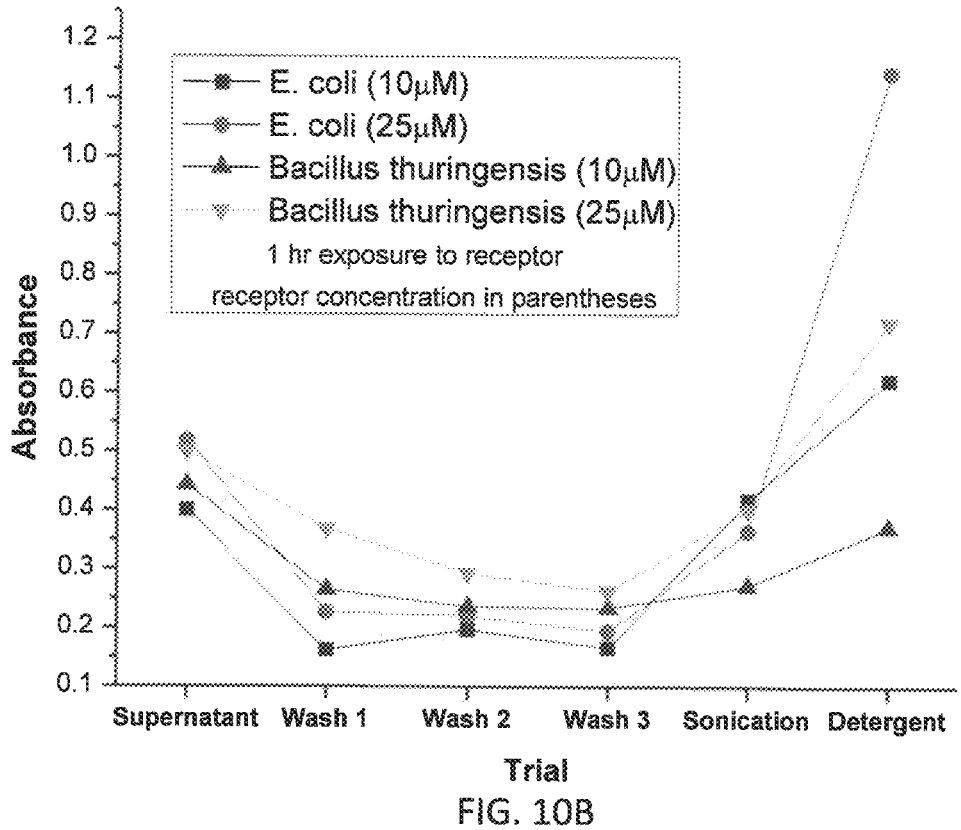
FIG. 10B is a graph of the results with liptin 3e used in cell lysis studies.

The uptake of phosphatidylglycerol liptin 3e by *E. coli* (Gram-negative *bacillus*), or *Staphylococcus aureus* or *Enterococcus faecalis* (both Gram-positive cocci) inhibits bacterial growth. We have reported that the 3e is able to penetrate both Gram-negative and Gram-positive bacterial walls and reach the plasma membrane. FIG. 10B shows the absorbance (420 nm) values of supernatants of various trials from cell lysis experiments with *E. coli* and *Bacillus thuringiensis* after incubating the bacterial solutions with liptin (10 or 25 μM) for 1 h. This previous work demonstrates that the liptin (previously referred to as a "receptor") binds to bacterial membrane components.

Here, we have determined the MIC of liptin 3e to be less than 2 μM. We assessed the MIC for *E. coli* and growth only in seen in control and 1 μM tubes, establishing an MIC between 1-2 μM. We also assessed the MIC for *Staph aureus* and growth was not observed in any tube except control, establishing an MIC at or below 1 μM.

Figure 11A:
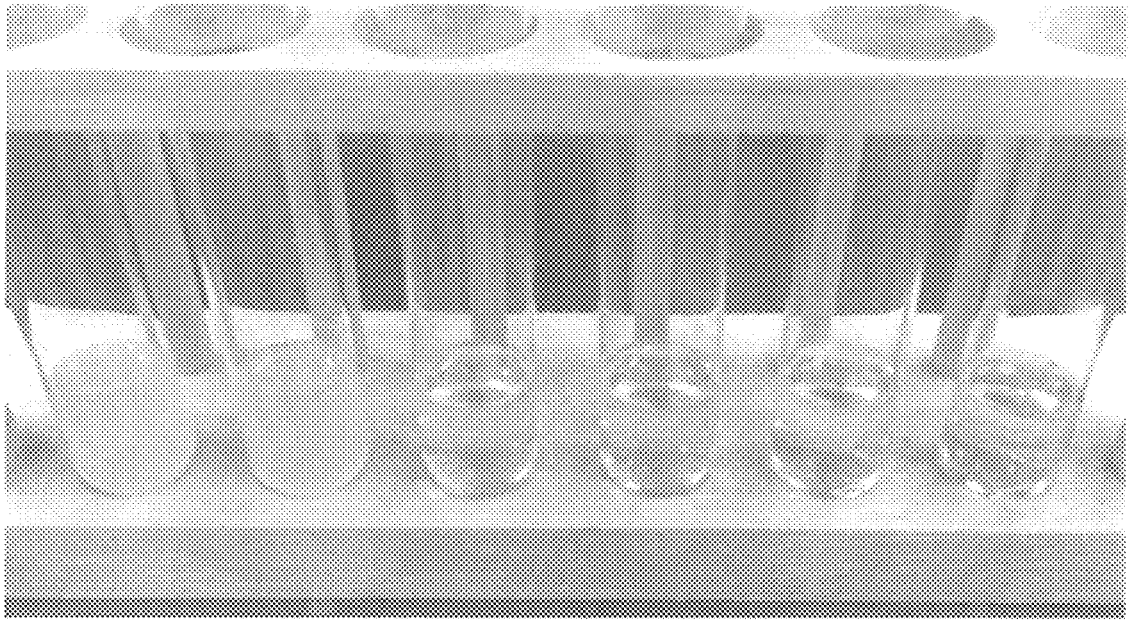
FIG. 11A is a photograph of MIC experiments with *E. coli* cultures.
Figure 11B:
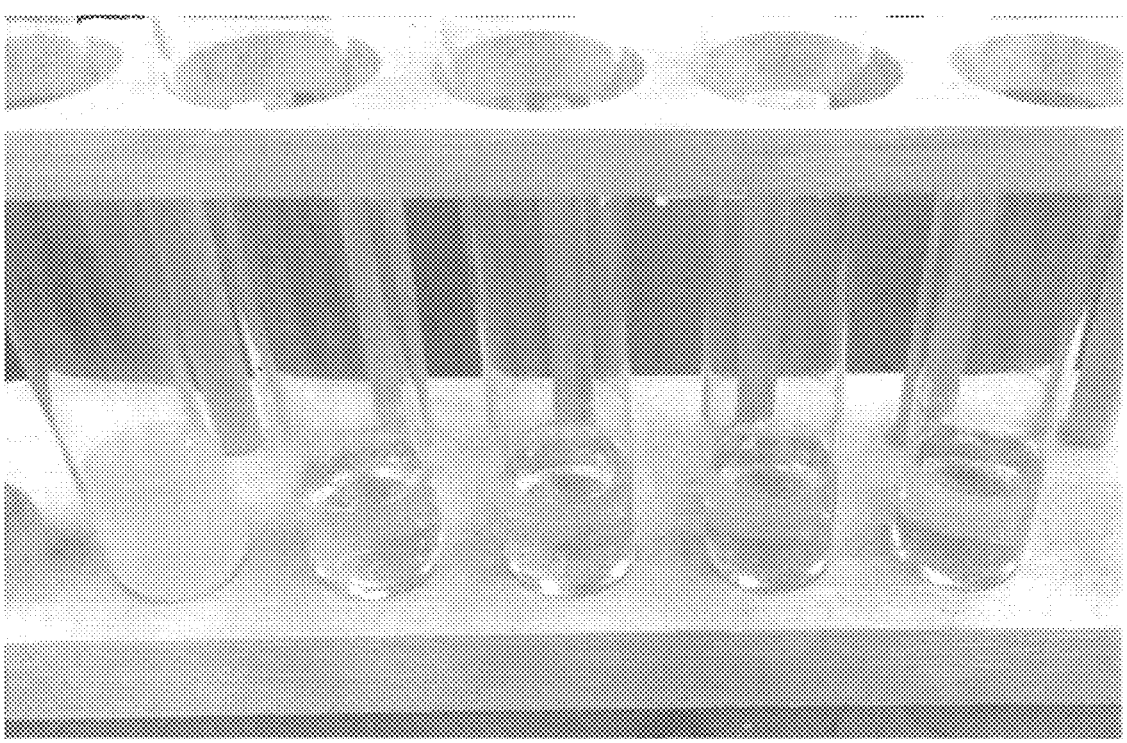
FIG. 11B is a photograph of MIC experiments with *E. coli* cultures.

Experimental for MIC with Liptin:

An *E. Coli* (JMR 223-MC4100) plate was grown up overnight in LB agar at 37° C. A good colony was selected and added to 5 mL LB growth media. This was incubated at 37° C. with shaking at 250 rpm until the solution reaches an OD of at least 0.5 or higher at 600 nm. A final solution was diluted 500× to an OD of 0.001, correlating to a CFU of 1×10⁶. 5 ml solutions of the diluted bacterial broth were measured out. Liptins were added to make solutions of 20 μM, 15 μM, 10 μM, 5 μM, 4 μM, 3 μM, 2 μM, and 1 μM (This means adding 0.2 mL, 0.15 mL, 0.1 mL, 0.05 mL, 0.04 mL, 0.03 mL, 0.02 mL, 0.01 mL of the 500 μM solution). Cultures were allowed to incubate overnight at 37° C. with shaking at 250 rpm. The following day, cultures were analyzed to evaluate the presence or absence of bacterial growth by spectrophotometry at 600 nm (0.66 mg of liptin in 0.95 mL of water; 0.15 OD Diluted 150× to OD of 0.001). Growth was observed in the control and 1 μM cultures. Growth was not observed in the 2 μM and up solutions. See FIGS. 11A-11B for a visual image of the *E. coli* cultures.

Figure 11C:
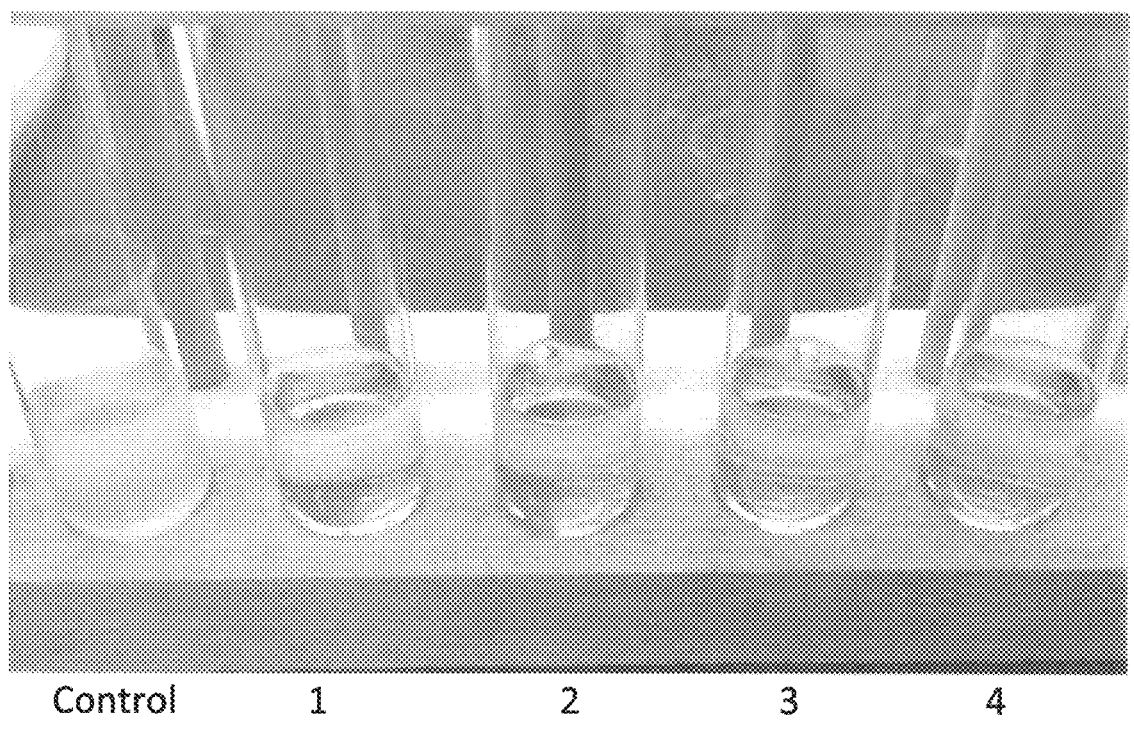
FIG. 11 C is a photograph of MIC experiments with *S. aureus* cultures.

*Staph aureus* (33186) cultures were prepared and analyzed as above. A good colony was selected and added to 5 mL LB growth media, incubated at 37° C./250 rpm until the solution reached an OD of at least 0.5 or higher at 600 nm. The final solutions were diluted 500× to an OD of 0.001. This correlates to a CFU of 1×10⁶. The liptin solution was made by adding 0.68 mg of liptin in 1 ml of water to yield 500 μM solution. The control showed significant growth overnight. (OD600=0.63), However, none of the solutions with the liptin showed any growth indicating an MIC for liptin 3e of less than 1 μM. See FIG. 11C for a visual image of the *S. aureus* cultures.

Figure 11D:
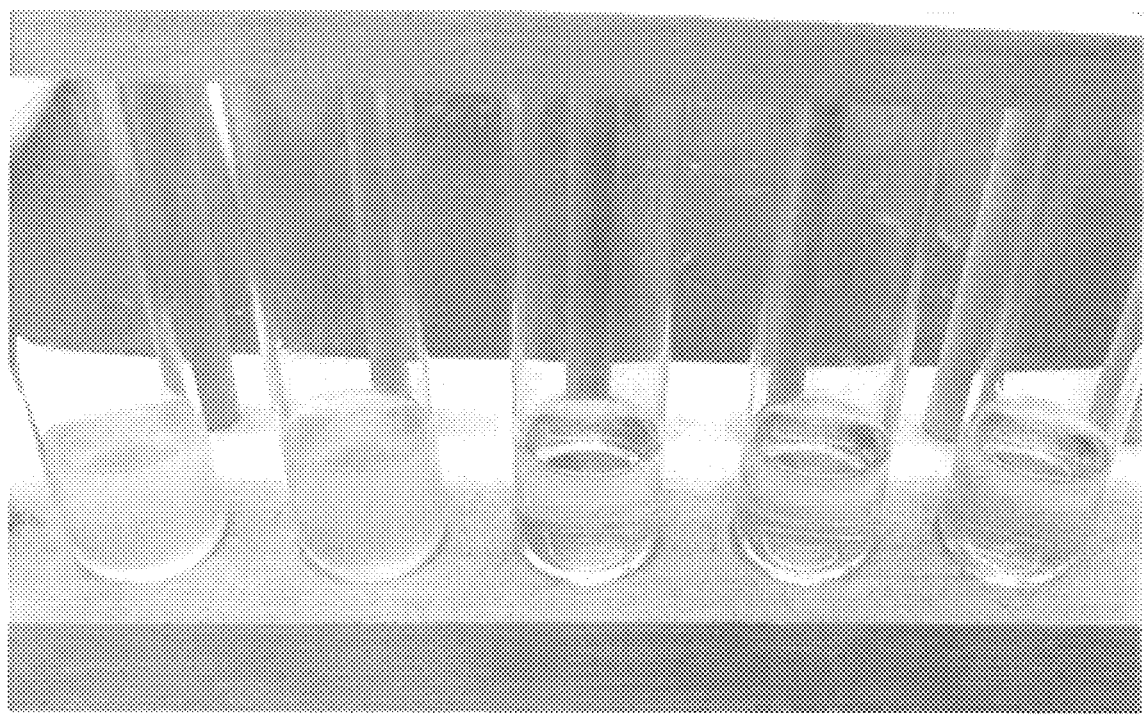

*Strep fuecalis* (aka *Enterococcus faecalis* 29213) cultures were prepared the same way as *S. aureus*, and analyzed as above. The control and 1 microM solutions showed significant growth. The OD600 of the control was 0.72. None of the others showed any growth. See photos for visual representation. See FIG. 11D for a visual image of the *S. fuecalis* cultures.

(3.2) Bacterial Experiments: Growth Experiments:

We further examined the effect of 3e on bacterial growth and 3e stability overnight.

(3.2.1) Overnight Study.

Figure 12A:
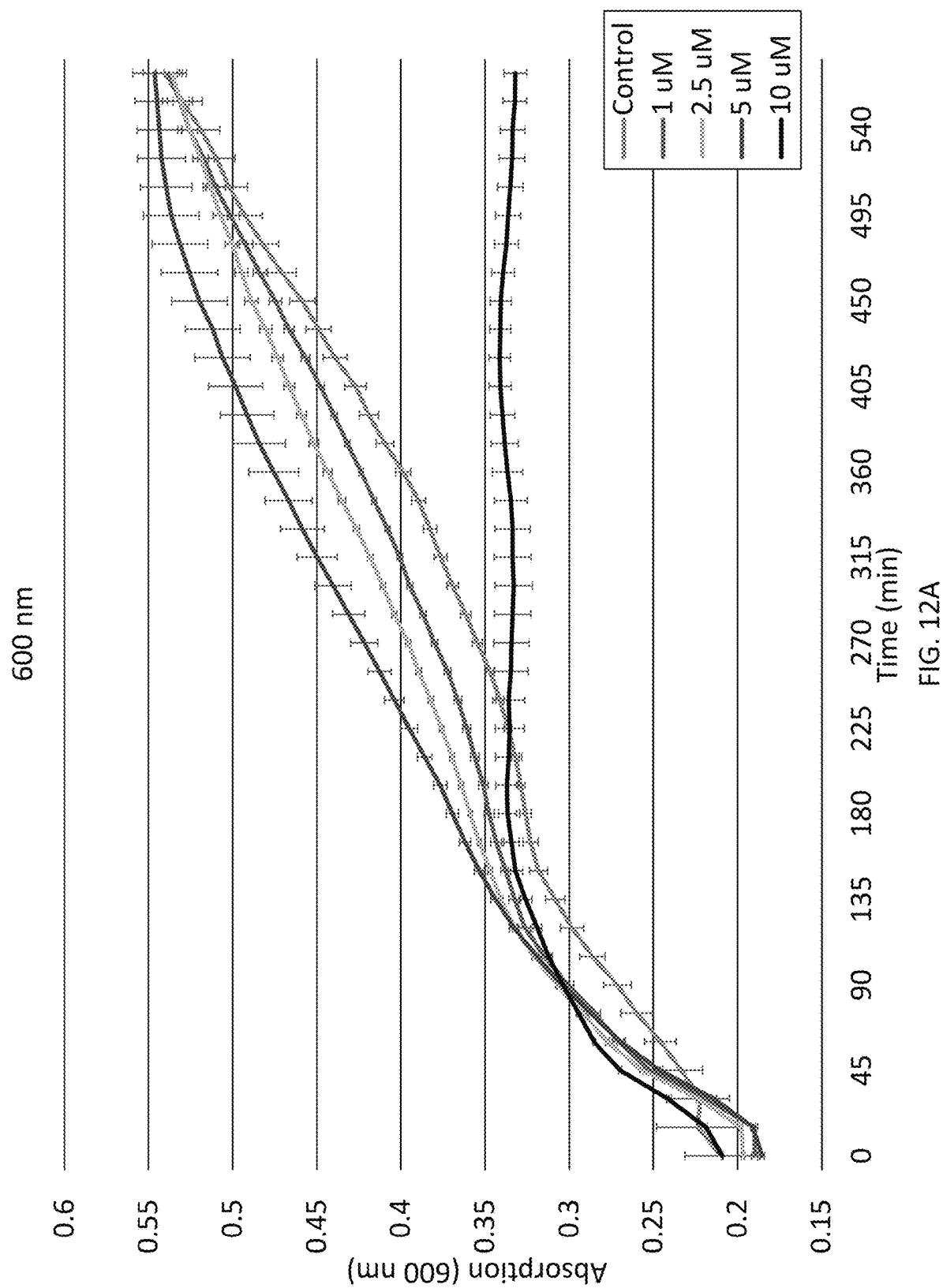
FIG. 12A is a graph of growth inhibition of liptin 3e on *E. coli* (MC4100)
Figure 12B:
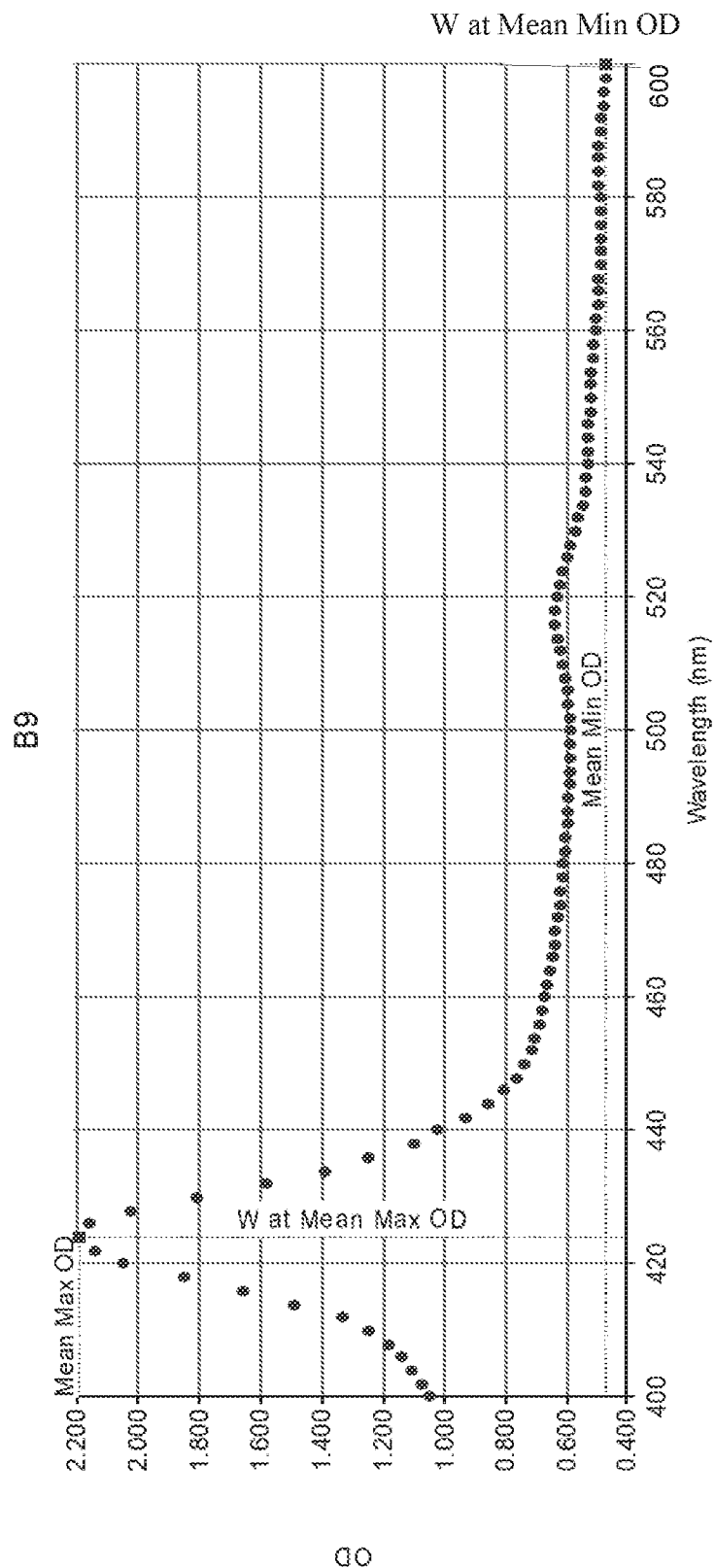
FIG. 12B is a graph of the UV/Visible spectrum of bacterial solution and liptin 3e after 12 hours.

A one-time addition of a 10 μM solution of liptin 3e to an *E. coli* (MC4100) bacterial culture (growth phase, 37° C., OD=0.2) in LB broth completely stops bacterial replication within 1-2 hours (stops at OD=0.35) for 12 hours while the UV/Visible spectrum of membrane-bound 3e shows no change over the same time period (OD vs time in minutes). Specifically, FIG. 12A illustrates the growth inhibition of liptin 3e on *E. coli* (MC4100), demonstrating complete stoppage of *E. coli* replication at 10 μM. The UV/Visible spectrum of bacterial solution and liptin after 12 hours is shown in FIG. 12B. This spectrum is identical to the spectrum of just liptin in water illustrating that the liptin is not degraded or metabolized when exposed to bacteria over long periods of time.

(3.2.2) Long Term Study in BH culture.

Figure 13A:
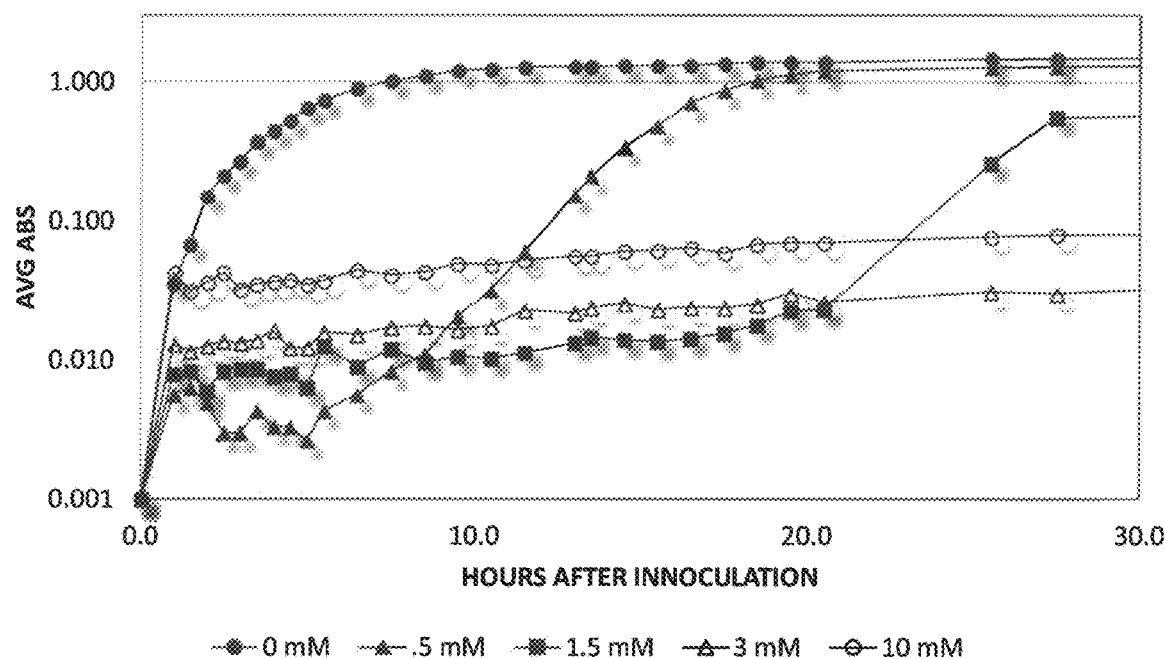
FIG. 13A is a graph showing data of long term growth experiments with *S. aureus* inoculated with various concentrations of liptin 3e.
Figure 13B:
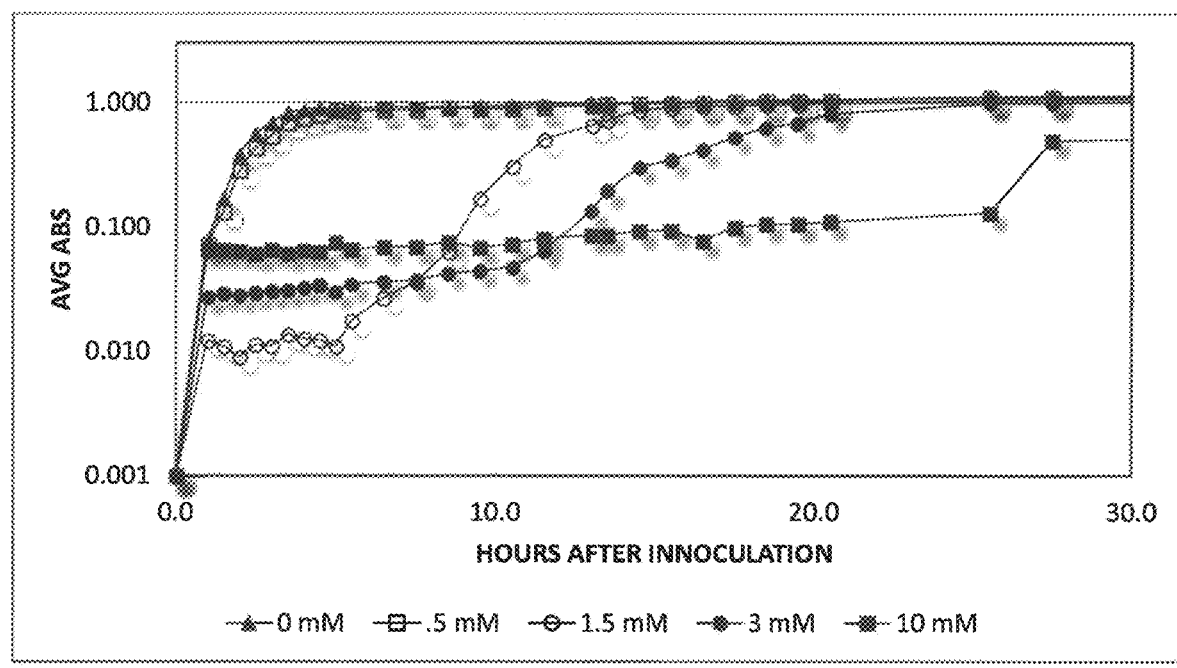
FIG. 13B is a graph showing data of long term growth experiments with *E. coli* inoculated with various concentrations of liptin 3e.

*Staphylococcus aureus* str. ATCC 29213 was grown as shake-tubes in brain-heart infusion medium supplemented with liptin and culture densities were measured by turbidity (FIG. 13A). At 0.5 μM 3e, there was an 8-h lag phase before culture density began to increase, which was not seen without addition of liptin 3e. Further, the growth rate was substantially lower over the next 12 h as culture density approached that of controls. Lag phases were on the order of days to weeks at liptin concentrations of ≥1.5 μM, and slow recovery followed. While growth was seen at 10 μM, the density of cultures after two weeks were much lower than controls. Growth of *Escherichia coli* str. MC4100 under similar conditions was substantially inhibited by liptin, but somewhat less so than *Staphylococcus*. Long lag phases of 8 h were observed at 1.5 μM liptin, as shown in FIG. 13B. Lag phases greater than 24 h were observed at 10 μM liptin with *E. coli* and culture densities were approaching those of controls within a week. Our novel antibacterial compounds attack plasma membranes through a less specific mode of action, which may avoid the pitfalls that lead to antibiotic resistance.

Figure 14:
FIG. 14 shows photographs of *S. aureus* plated on LB plates in the presence of 1 µM 3e (top left plate) or 5 µM 3e (top right plate), with the control (no liptin) in the bottom panel.

(3.3) Bacterial Experiments: Bactericidal Experiments:

MBC results for *E. coli* (MC4100) and *E. feucalis* (29213) were similar, in that low or no growth was only seen in LB plates grown from LB cultures that contained much more than four times the MIC concentrations. Cultures (5 mL) starting at 0.001 OD were grown overnight at 37° C. with different concentrations of liptin, and then a sample of culture was added to an LB plate and then it was incubated for 16 hours at 37° C. However, results for *S. aureus* (33186) showed strong bactericidal effects at 5 µM concentration of 3e. The LB plates shown in FIG. 14 for *S. aureus* are representative: top left plate, 1 µM 3e; top right, 5 µM 3e; bottom, control (left plate, 2 uL of the LB culture was put in 1 mL of LB growth media to dilute it, then this was placed onto an LB plate; right plate, 1 mL of the culture was directly plated onto a LB plate). All experiments were done in triplicate, including control. MIC of *S. aureus* previously determined to be 1 µM or less.

(3.4) Bacterial Experiments: Resistance Experiments:

Triplicate serial passage experiments were undertaken with *E. coli* (MC4100), *S. aureus* (33186) and *E. feucalis* (29213). In brief, after the growing bacterial culture exhibited an OD between 0.5-1.0, a small amount was removed and added to new LB culture broth for a starting OD around 0.001. In each experiment the concentration of 3e was kept at 0.5 MIC determined for each bacterial strain in LB culture at 37° C. Preliminary experimental data shows that although liptin-PG complex formation initially stunts bacterial growth, at 0.5 MIC it is not bactericidal. Based on the OD change from bacterial growth during each experiment, we estimate that over the 15 serial passages a total of 80-100 generations of bacteria were grown. MICs (not shown) determined from bacterial cultures taken the end of the 15 serial passages were no different than initial MICs.

Figure 15A:
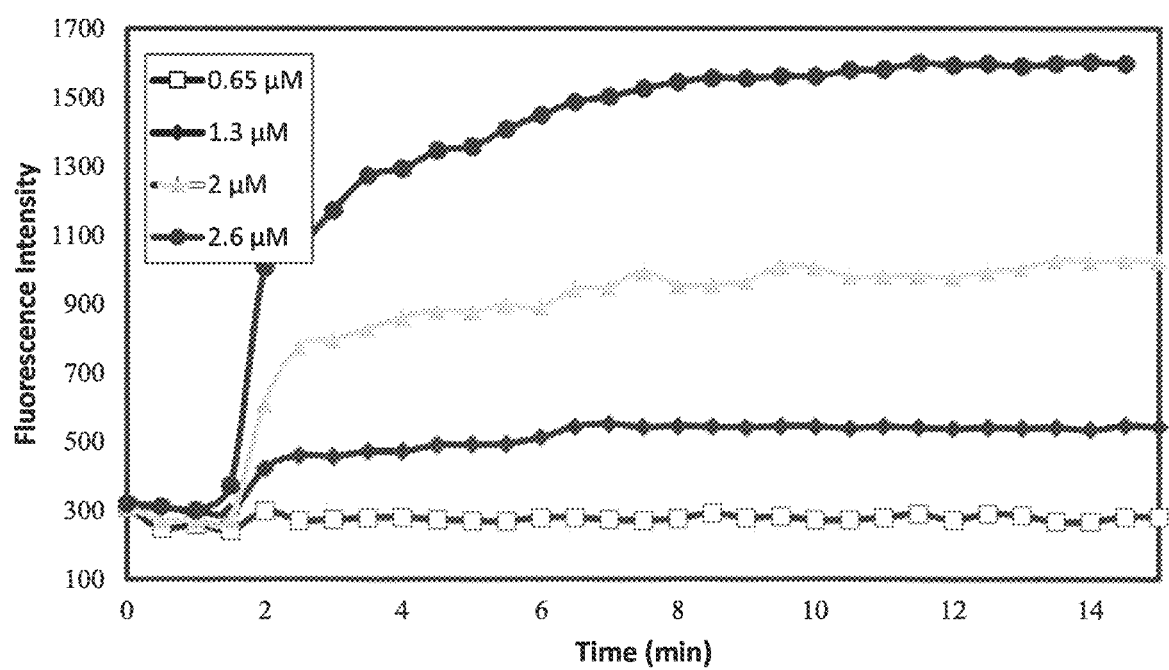
FIG. 15A is a graph of data from depolarization experiments measuring fluorescence of 3,3' diethylthiodicarbodyanine iodide in *S. aureus* incubated in the presence of a known antimicrobial (CSA-25) at varying concentrations.
Figure 15B:
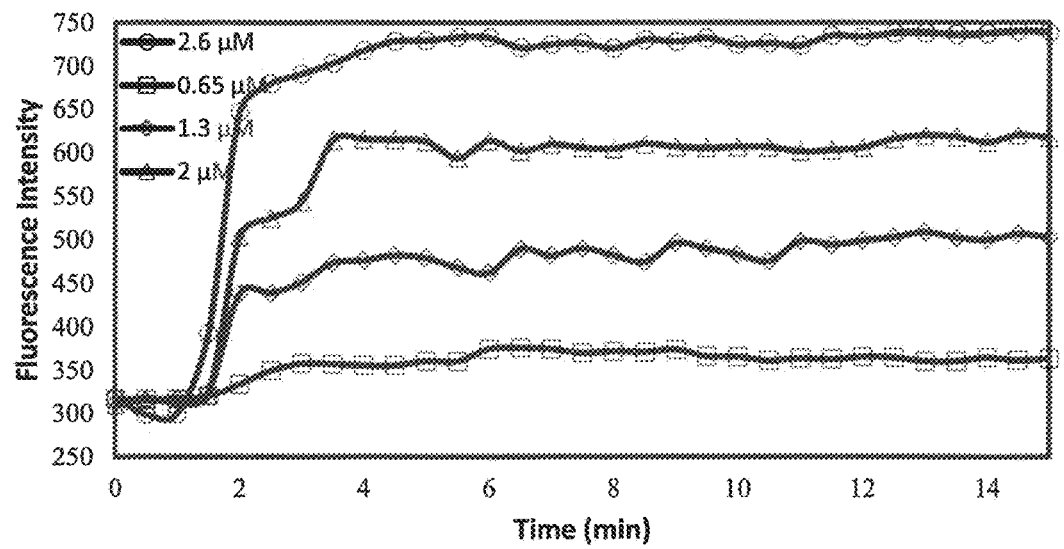
FIG. 15B is a graph of data from depolarization experiments measuring fluorescence of 3,3' diethylthiodicarbodyanine iodide in *S. aureus* incubated in the presence of an ammonium-picket porphyrin at varying concentrations.
Figure 15C:
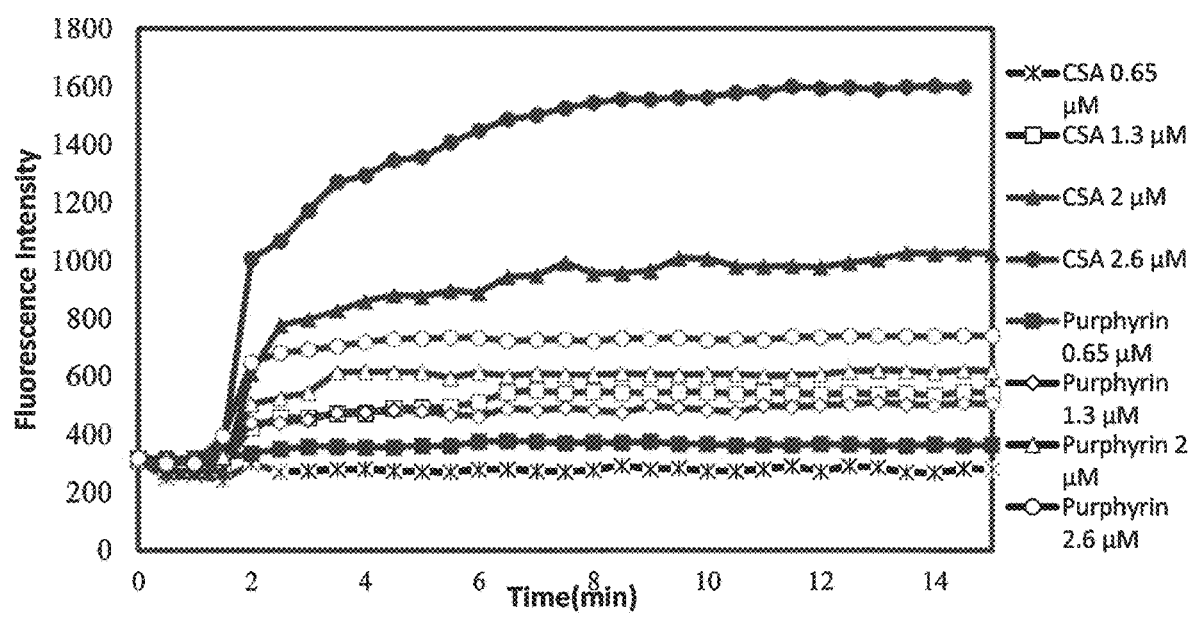
FIG. 15C is a graph of data from depolarization experiments measuring fluorescence of 3,3' diethylthiodicarbodyanine iodide in *S. aureus* incubated in the presence of a combination of ammonium-picket porphyrin and CSA-25 at varying concentrations

(3.5) Bacterial Experiments: 3e *S. aureus* Causes Plasma Membrane Depolarization Upon Complexation with PG:

The graph in FIGS. 15A-15C represents the depolarization of *S. aureus* plasma membrane measured by an increase in the fluorescence of 3,3-diethylthiodicabodyanine iodide. The dye, which has direct access to the Gram-positive plasma membrane, becomes highly fluorescent in membranes where polarization is lost. Liptin 3e was added after 1.5 min at concentrations shown, and fluorescence increased in a concentration-dependent manner. The membrane effects were measured against the known membrane-disruptive agent, cationic steroid antimicrobial-25 (CSA-25), one of a group of cholic acid-derived antimicrobial also known as ceragenins. This assay measured the effects of the Ammonium-picket porphyrin alone those of CSA-25 alone or a combination of Ammonium-picket porphyrin and CSA-25.

Experimental

Bacterial cultures were grown overnight in TSB at 37° C. Cells were harvested by centrifugation and washed in a buffer containing 250 mM sucrose, 5 mM MgSO4, and 10 mM potassium phosphate (pH 7.0). After three washings, pellets were re-suspended in the same buffer. Fractions from each cell suspension were diluted in the same buffer in a cuvette to an optical density (A600) of 0.085 along with the dye DiS-C2(5) at a concentration of 1 M. The dye was allowed to incorporate for 7 min at room temperature, followed by 7 min at 37° C., which gave a stable baseline. An excitation wavelength of 600 nm and an emission wavelength of 660 nm were used to monitor depolarization. Samples were stirred during the experiment at a constant temperature of 37° C. Fluorescence measurements were taken at 30-s intervals before and after addition of ceragenins. FIG. 15A illustrates the depolarization of *S. aureus* measured by an increase in fluorescence of 3,3' diethylthiodicarbodyanine iodide (DiS-C2(5)). CSA-25 was added at 90 s at the following concentration: 0.69 µM, 1.3 µM, 2 µM, and 2.6 µM.

FIG. 15B illustrates the depolarization of *S. aureus* measured by an increase in fluorescence of 3,3' diethylthiodicarbodyanine iodide. Ammonium-picket porphyrin was added at 90 s at the following concentration: 0.69 µM, 1.3 µM, 2 µM, and 2.6 µM.

FIG. 15C illustrates the depolarization of *S. aureus* measured by an increase in fluorescence of 3,3' diethylthiodicarbodyanine iodide. CSA-25 and Ammonium-picket porphyrin was added at 90 s at the following concentration: 0.69 µM, 1.3 µM, 2 µM, and 2.6 µM.

(3.6) Bacterial Experiments: Membrane Depolarization in *E. coli*.

Figure 16:
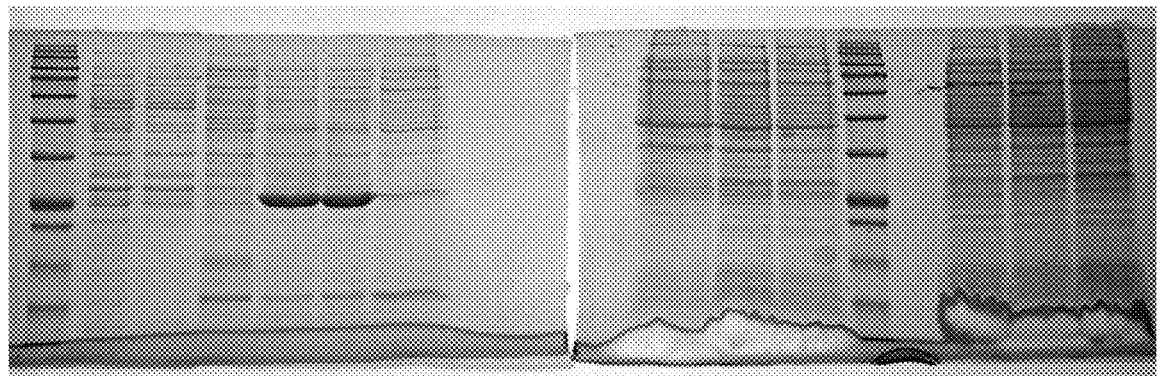
FIG. 16 is an image of a gel electrophoresis of the periplasmic and cytosolic proteins of *E. coli* bacteria (with and without IPTG induction of the overexpression of PapD)

The *E. coli* strain MC4100 will produce the pili chaperone PapD, a periplasmic protein, when induced by IPTG. When bacterial cultures were incubated with both IPTG and 5 µM 3e no PapD was found in either the periplasmic space or cytosol. Gel electrophoresis results shown in FIG. 16. The left panel represents the periplasmic fraction with lanes running left to right: ladder, NR, C, R, all with no IPTG; NR+IPTG, C+IPTG, R+IPTG (negative control was porphyrin A) or in the cytosol represented in the right panel with lanes running from left to right: NR, C, R, all with no IPTG; ladder, NR+IPTG, C+IPTG, R+IPTG (negative control was porphyrin A). (NR=no liptin, C=control, R=liptin). IPTG gets into the cytoplasm most efficiently via uphil symport via the plasma membrane protein lac permease when the plasma membrane is fully polarized. Thus, the lack of transport which stopped over expression of PapD strongly suggests that the plasma membrane has been depolarized and the pmf shut down.

On the other hand, with *E. coli* BL 21 (Tuner pLysS) tetracycline-induced protein YqhD (a cytosolic alcohol dehydrogenase) was produced whether or not 3e was present in the bacterial culture (gel not shown). Although different strains (liptin 3e was shown to pass through the cell wall in both strains) and proteins, the larger difference between the two gel electrophoresis experiments is that IPTG requires lac permease to efficiently transverse the plasma membrane, where the inducer tetracycline will permeate the membrane by itself. Since it would not be expected that inhibition of lac permease alone would inhibit bacterial growth (as many other food sources are available in the broth), las permease function in general was deleteriously affected, most likely by pmf disruption. When 3e was incubated with the bacteria at 10 µM most protein synthesis was effectively disrupted (not shown).

Example 4

Hepatocyte Toxicity

Toxicity of compounds to eukaryotic cells was assessed by MTT assay of cultured HepG2 human hepatocyte cells grown in media supplemented with 10% fetal bovine serum and antibiotics.

Cell Culture:

Human liver HepG2 cells were cultured in 100 mm$^2$ Falcon tissue culture plates in DMEM with high glucose (4500 mg/L) supplemented with 10% fetal bovine serum, 50 µg/ml streptomycin and 50 IU/ml penicillin at 37° C. and 5% $CO_2$. Cells were cultured to about 70-80% confluence, and then seeded into 96 well plates depending and grown to 70-80% confluence for 2-3 days unless otherwise stated.

Figure 17:
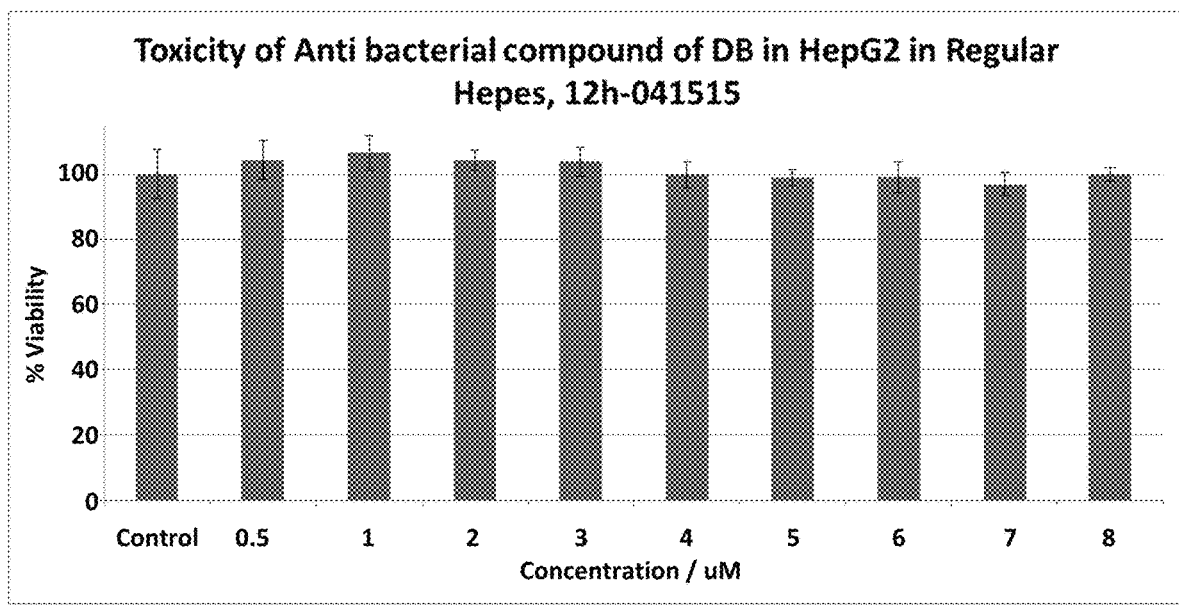
FIG. 17 is a graph of the toxicity of 3e when incubated with hepatocytes for 9-12 hours at varying concentrations.

Measurement of Cell Viability:

Cell viability was determined by MTT [3-(4,5-dimethylthiazol-2-yl)-2,5-diphenyltetrazolium bromide)] assay (Denizot & Lang 1986). Briefly, cells were seeded on 96-well plates and allowed to grow until 70-80% confluence. Prior to the experiment, medium was replaced with KRB containing a desired concentration of the toxin or other reagents and incubated for 9 h to 12 h depending on the experiment at 37° C. After the incubation, 10 µL of 5 mg/mL MTT solution was added to each well and was incubated for 2 h at 37° C. The resulting formazan was solubilized by the addition of 210 µL detergent solution (50% DMF, 20% SDS) followed by incubation for 4 h at 37° C. and was quantified based on the difference in the absorbance at 570 nm and 650 nm (Mosmann 1983). Results are expressed as viability of toxin treated cells with respect to control cells which were treated under the same conditions except in the absence of the toxin. Reference: Kadigamuwa C C, Le VQ Wimalasena K (2015) "2, 2'- and 4, 4'-Cyanines are Transporter Independent in vitro Dopaminergic Toxins with the Specificity of Toxicity similar to MPP+" *J. Neurochemistry*, 135, 755-767. FIG. 17 illustrates the toxicity of liptin 3e when incubated with Hepatocytes for 9-12 hours. These data demonstrate the lack of toxicity of liptin 3e down to 0.5 µM.

Example 5

Erythrocyte Toxicity

Figure 18:
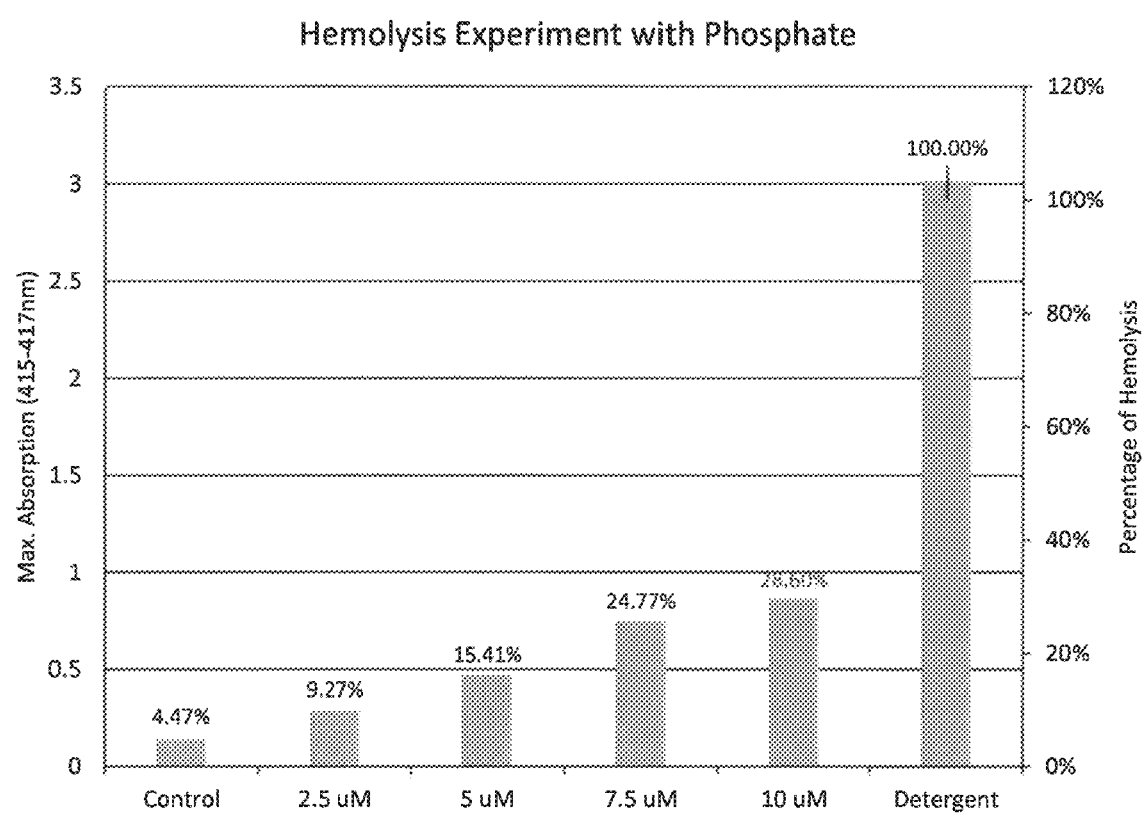
FIG. 18 is a graph demonstrating the lack of toxicity of liptin 3e to eukaryotic erythrocytes as assessed by UV/Visible spectroscopy.

Toxicity of liptin 3e to eukaryotic erythrocytes was assessed by UV/Visible spectroscopy, whereby the change in absorbance at 414 nm was used to quantify the release of hemoglobin, where 100% hemolysis was measured by adding 1% Triton X-100 detergent. Red blood cells (RBCs) were suspended in a buffer of 25 mM TRIS and 1.5 mM dihydrogenphosphate anion (serum inorganic phosphate levels). To the RBCs samples was added differing concentration of 3e—2.5 µM, 5 µM, 7.5 µM, and 10 µM, as well as control containing no 3e, and after 30 minutes incubation and gentle shaking at 37° C. spectra were obtained. FIG. 18 shows that at or near 3e's MIC concentrations of 2.5-5 µM, there was minimal 4.5-11% damage to red blood cells, compared to the absorbance of 100% hemolysis and release of hemoglobin minus the control release.

Example 6

Additional Characterization of Liptins 1h-k and 3e-h

Efflux Experiments with Liposomes Containing PG and Phosphatidylethanolamine (PA)

Figure 19A:
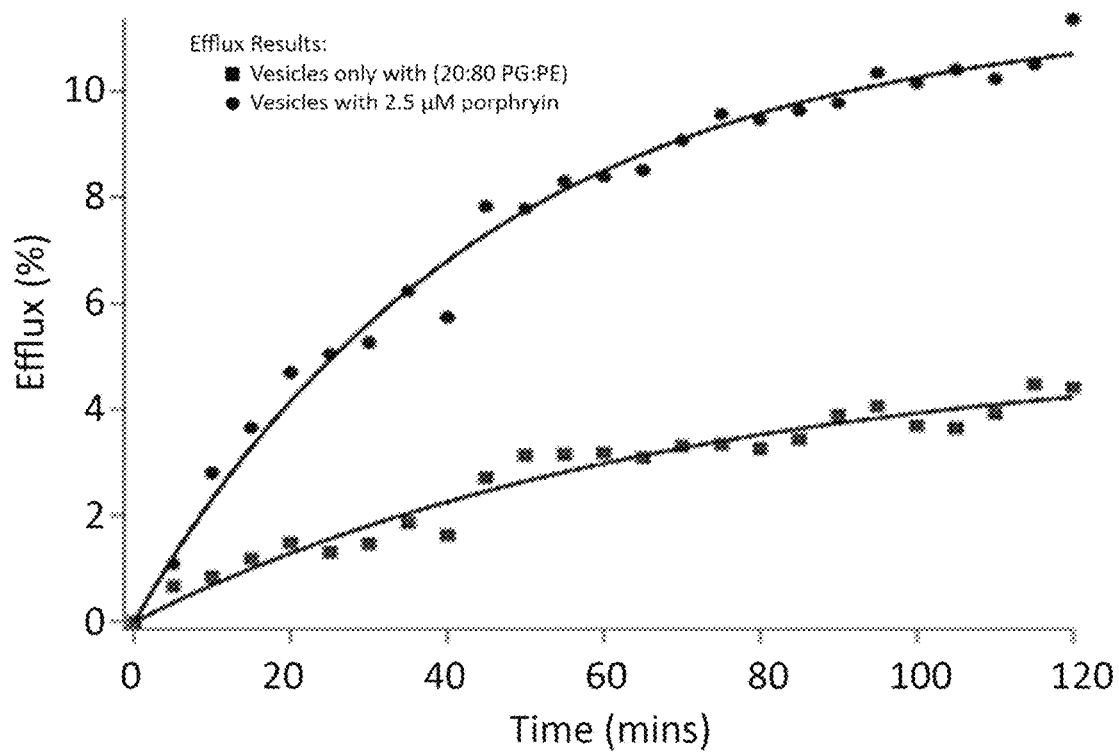
FIG. 19A is an efflux graph of liptin 3e with a PG liposome showing carboxy-fluorescein dye leakage.

Liptin 3e causes membrane leakage when it binds to PG in a membrane, as evidenced by the efflux of fluorescent carboxy-fluorescein from model lipid vesicles of 80% PE/20% PG (the approximate lipid content models *E. coli*'s plasma membrane), shown in FIG. 19A. In the graph, the circles represent the data for 2.5 mM liptin 3e, while the square are the control without liptin 3e. Not shown is the effect of the bee AMP melittin, which forms pores in membranes at 2.5 µM concentrations. Upon addition of melittin within a few minutes of addition the efflux is 100%. This strongly suggest that the liptins are not forming pores, but rather making the membrane more permeable to dye leakage.

Figure 19B:
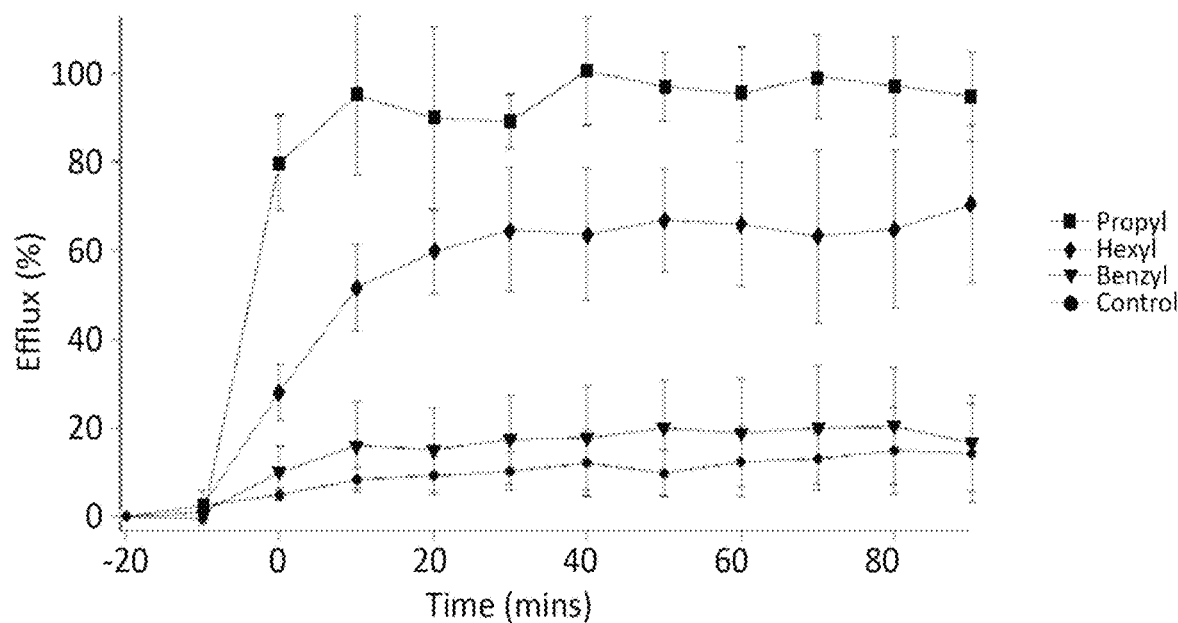
FIG. 19B is an efflux graph of liptins 3f-h with a PG liposome showing carboxy-fluorescein dye leakage.
Figure 19C:
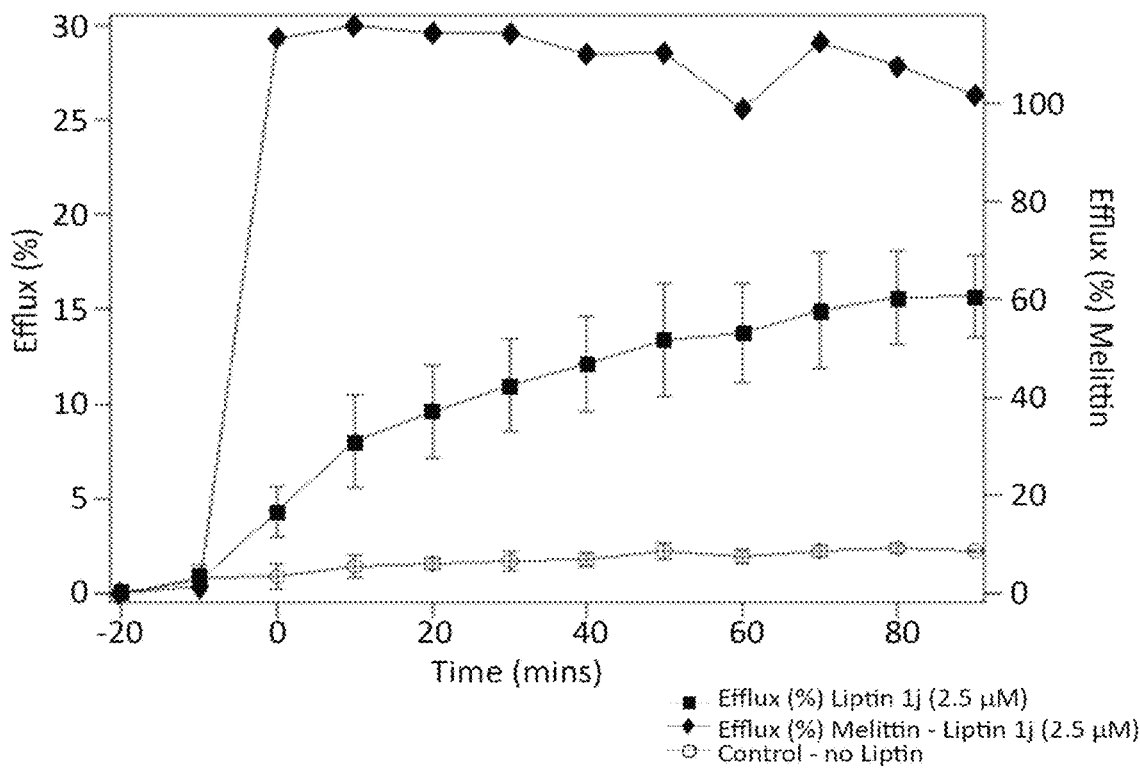
FIG. 19C is an efflux graph of liptin 1j with a PG liposome showing carboxy-fluorescein dye leakage.
Figure 19D:
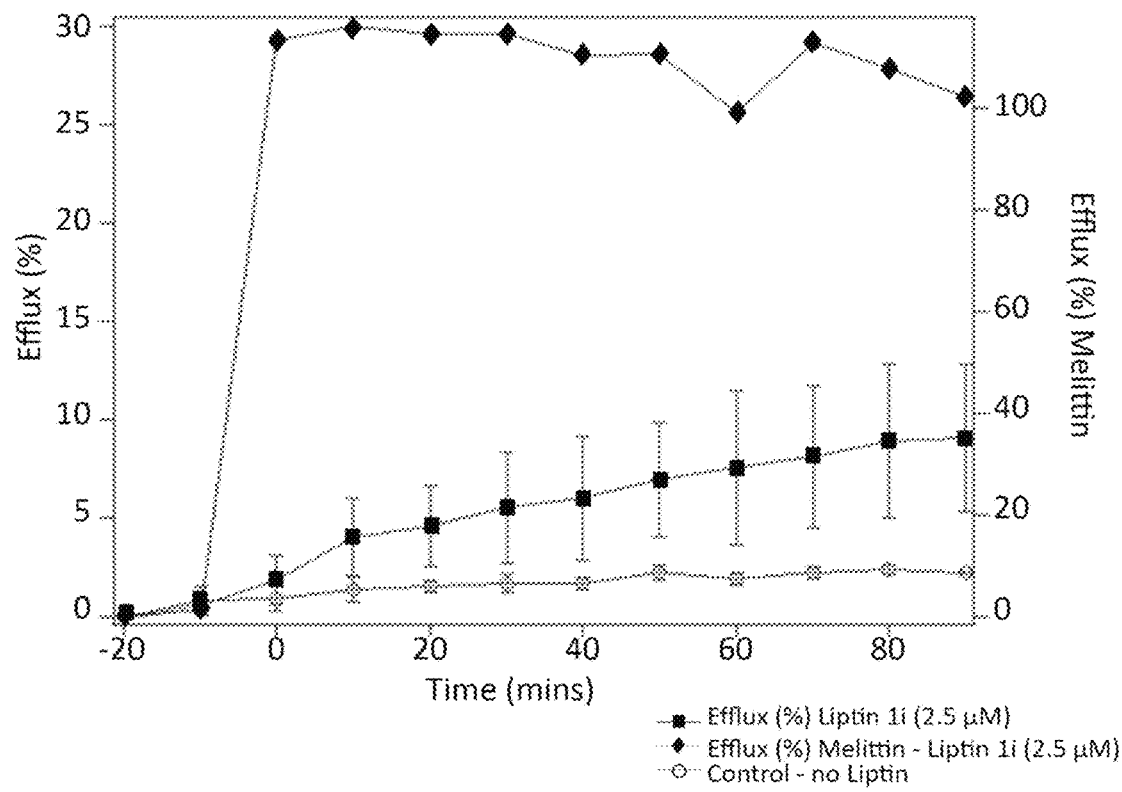
FIG. 19D is an efflux graph of liptin 1i with a PG liposome showing carboxy-fluorescein dye leakage.
Figure 19E:
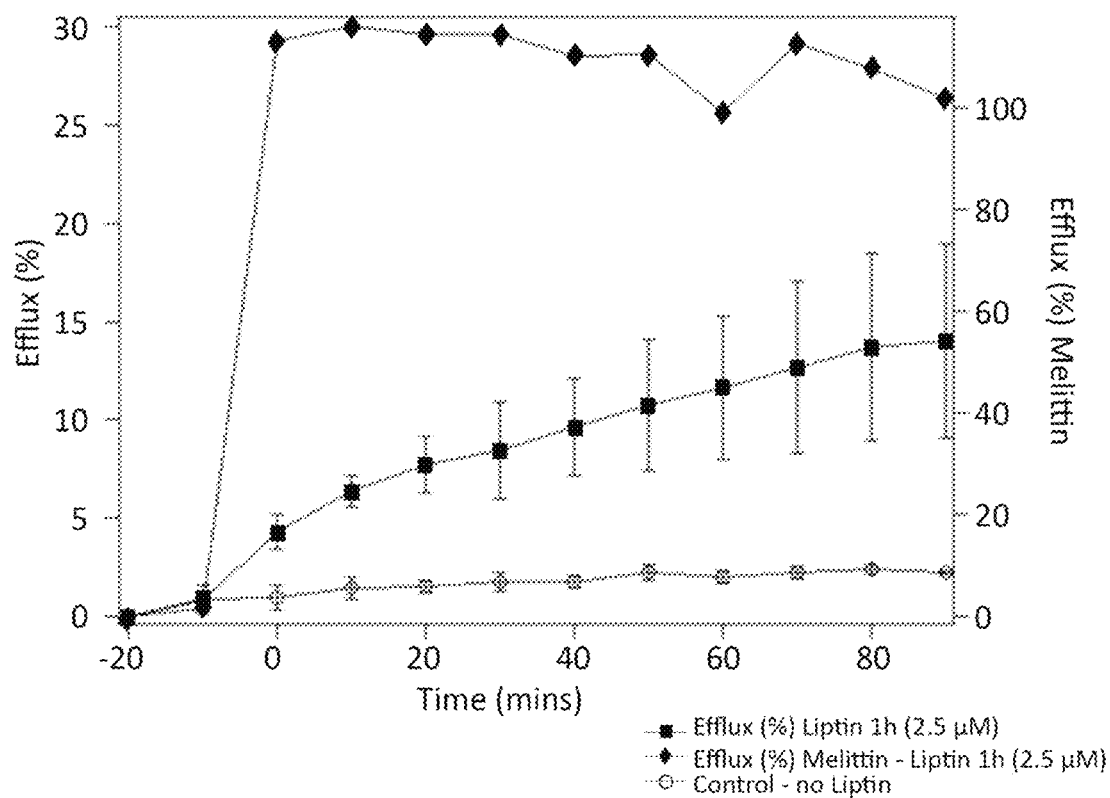
FIG. 19E is an efflux graph of liptin 1h with a PG liposome showing carboxy-fluorescein dye leakage.
Figure 19F:
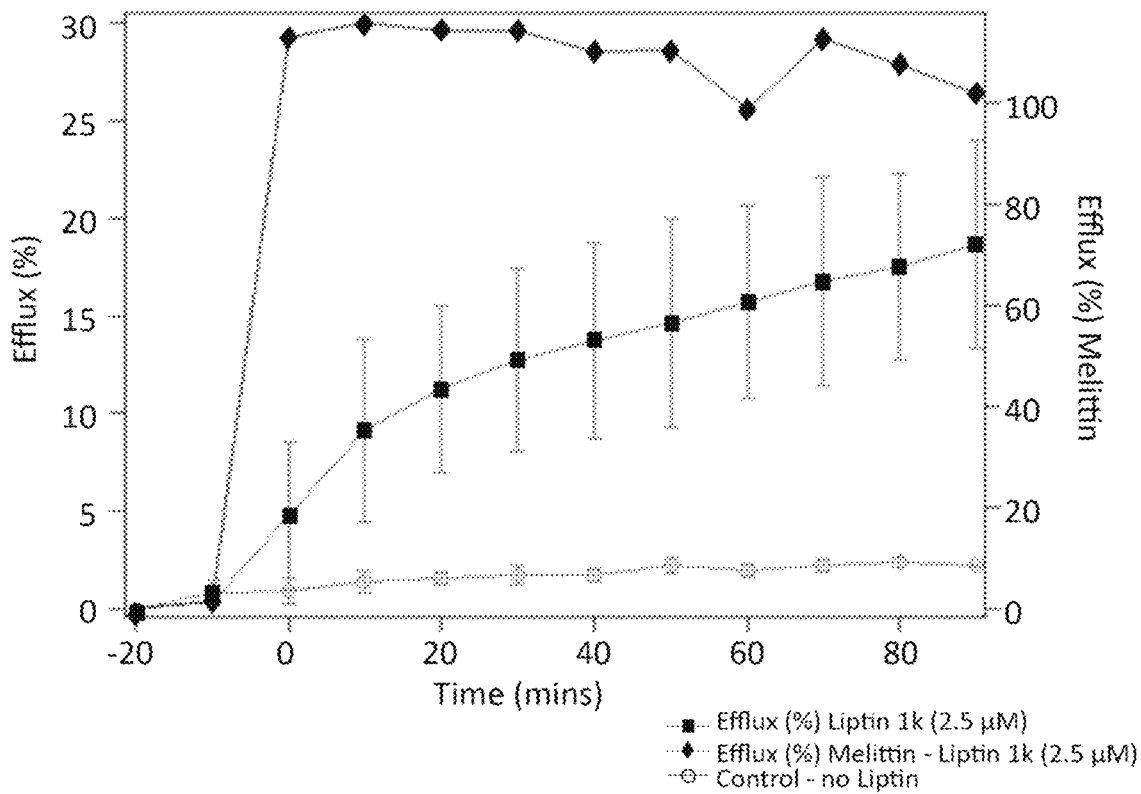
FIG. 19F is an efflux graph of liptin 1k with a PG liposome showing carboxy-fluorescein dye leakage.
Figure 20A:
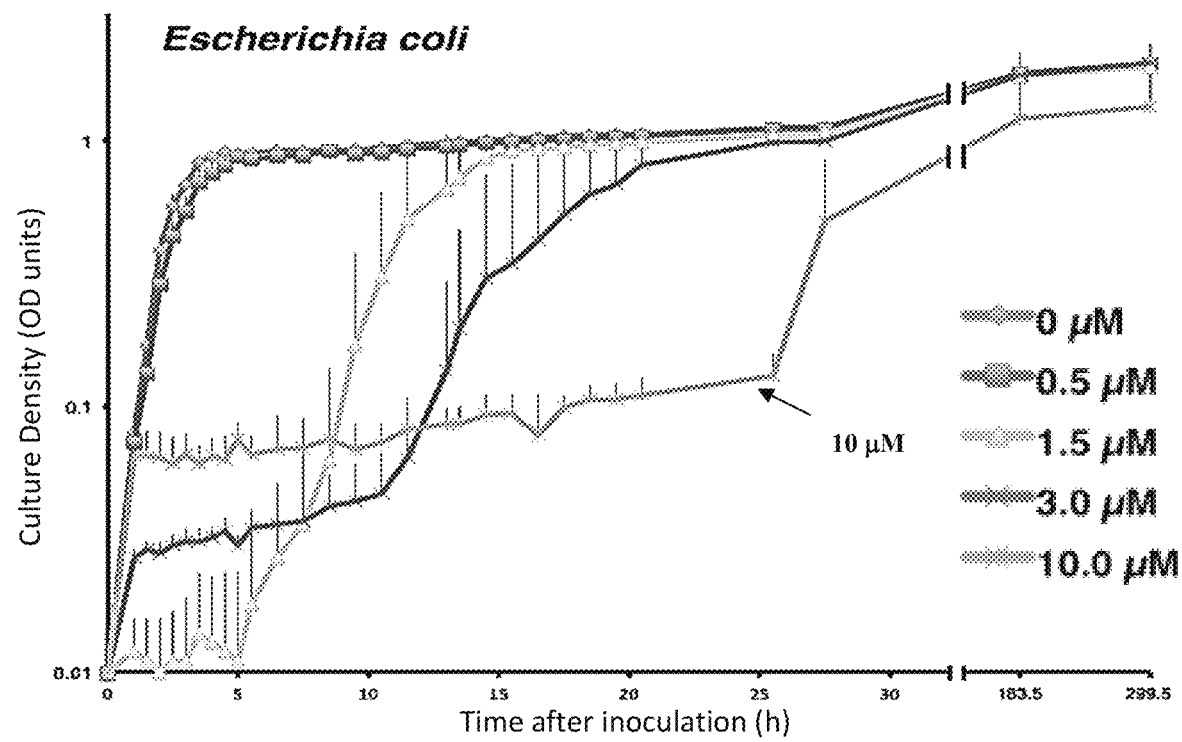
FIG. 20A is a growth curve in BHI culture for *E. coli* with one inoculation of liptin 3e.
Figure 20B:
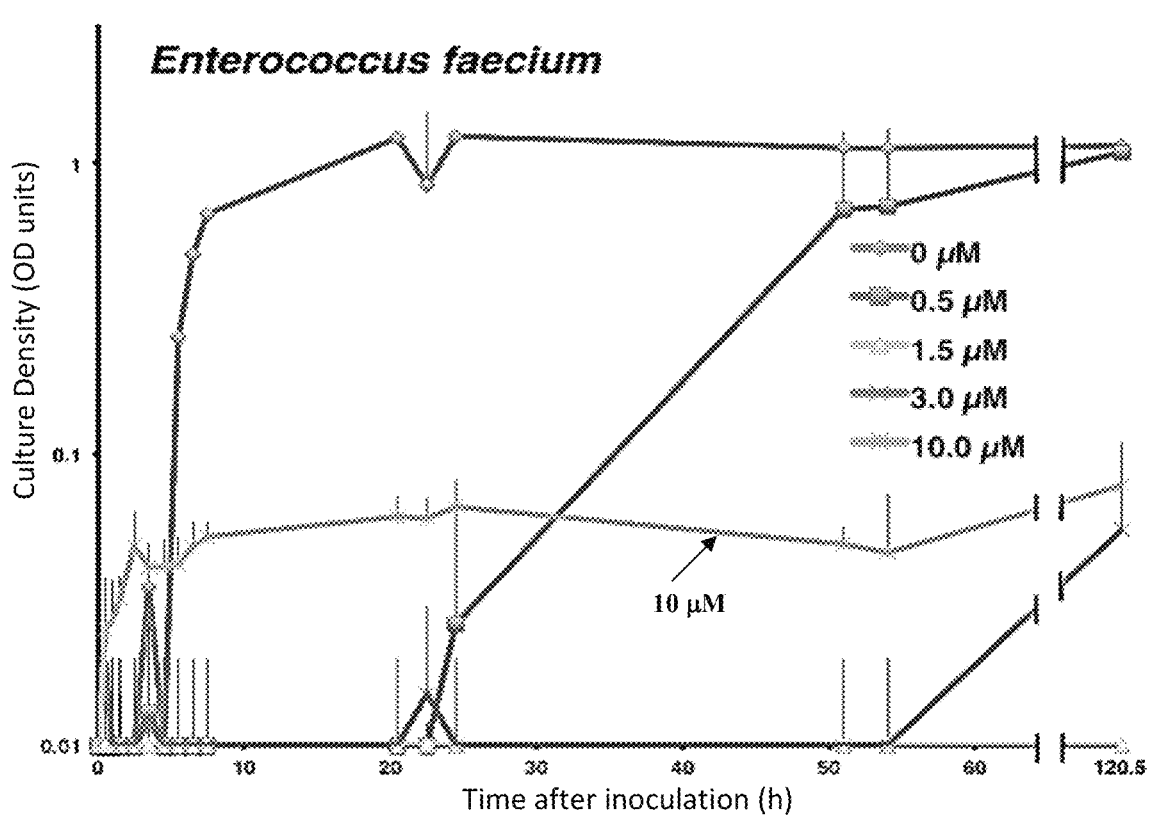
FIG. 20B is a growth curve in BHI culture for *E. faecium* with one inoculation of liptin 3e.
Figure 20C:
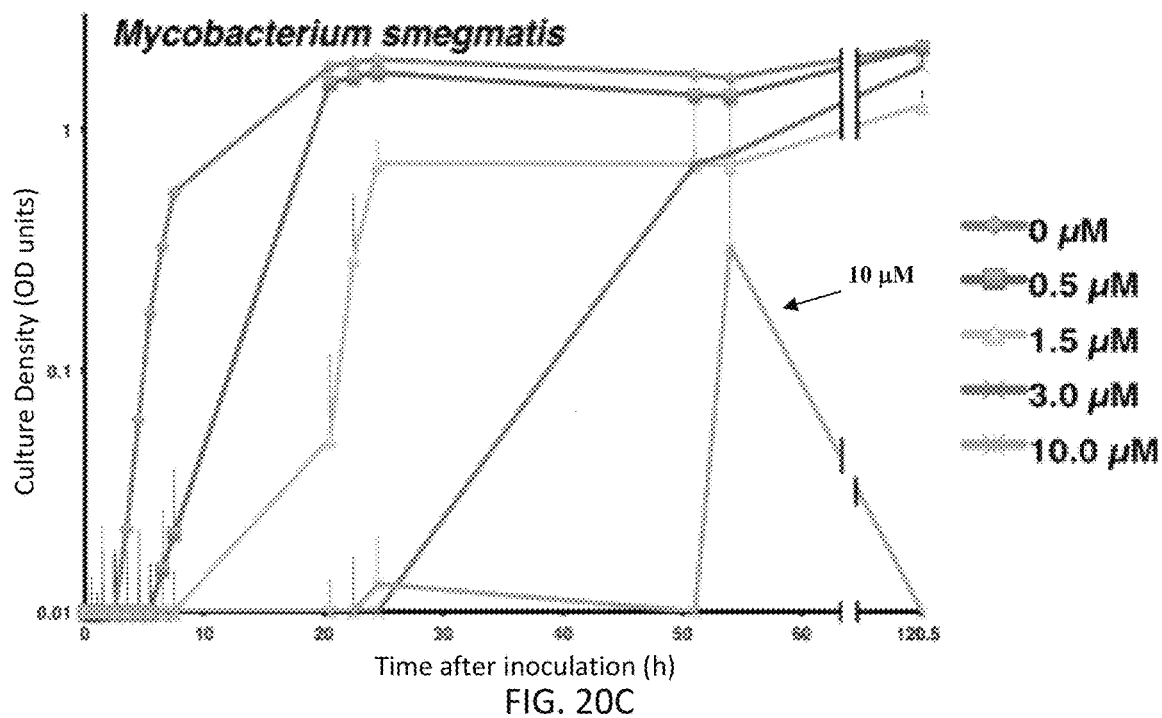
FIG. 20C is a growth curve in BHI culture for *M. smegmatis* with one inoculation of liptin 3e.
Figure 20D:
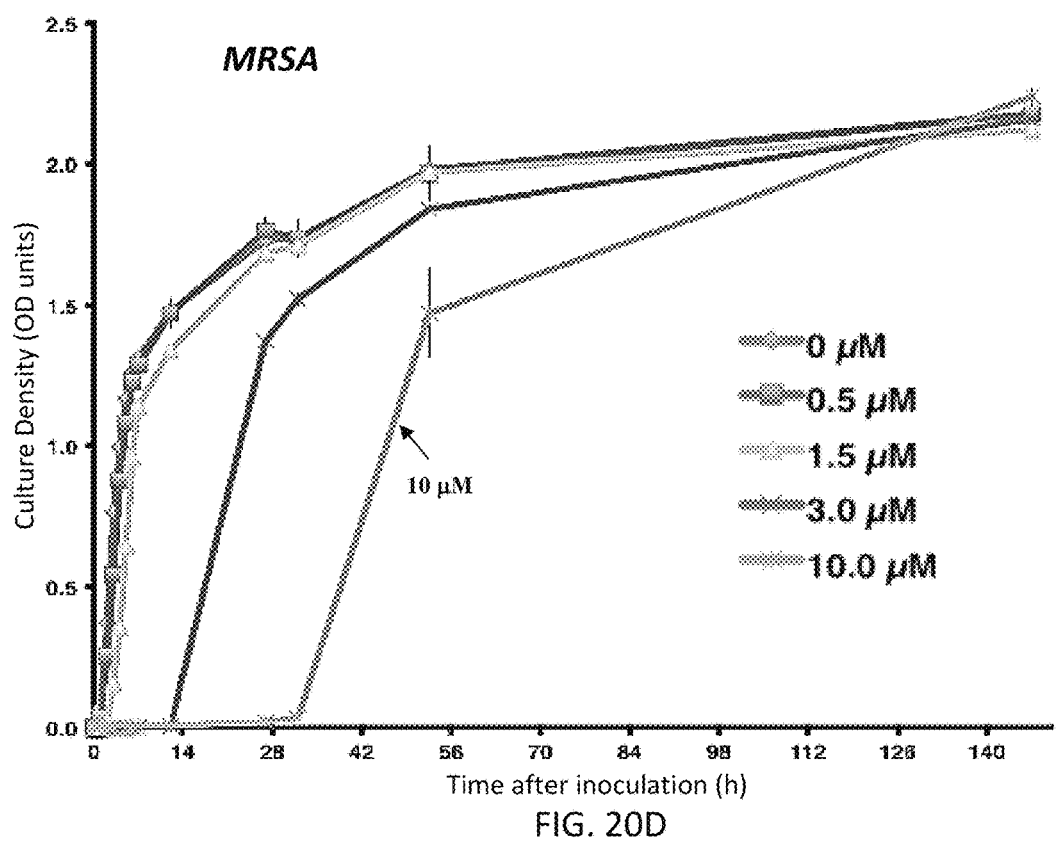
FIG. 20D is a growth curve in BHI culture for Methicillin-resistant *S. aureus* (MRSA) with one inoculation of liptin 3e.
Figure 20E:
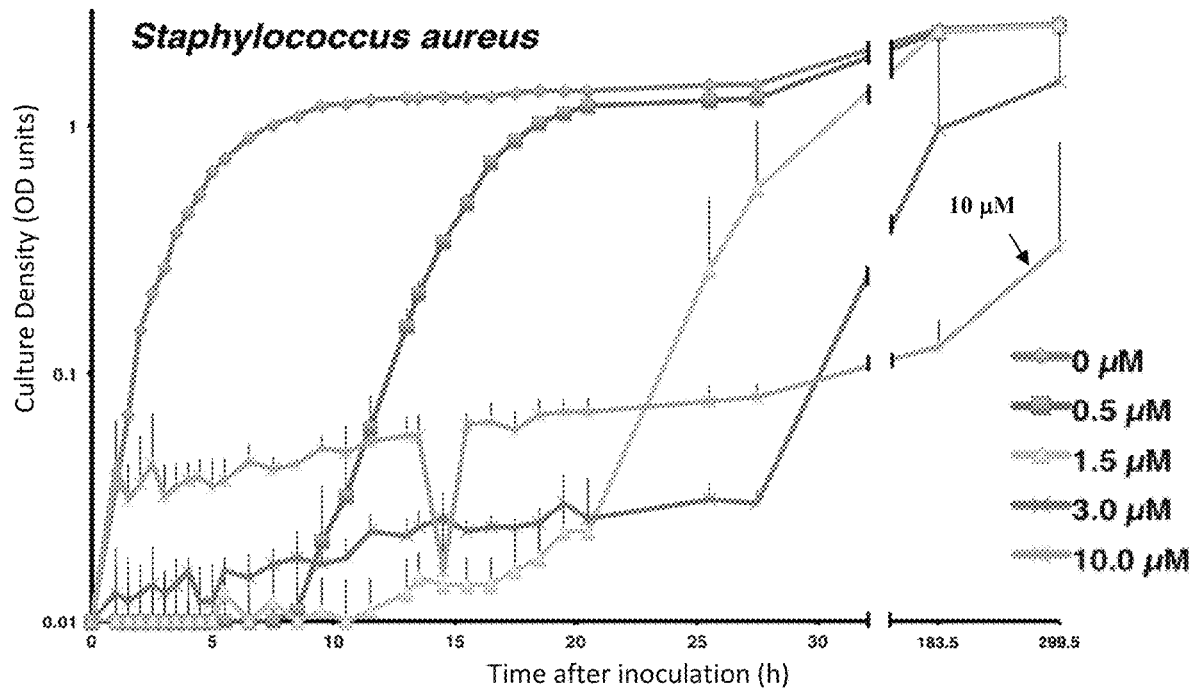
FIG. 20E is a growth curve in BHI culture for *S. aureus* with one inoculation of liptin 3e.
Figure 20F:
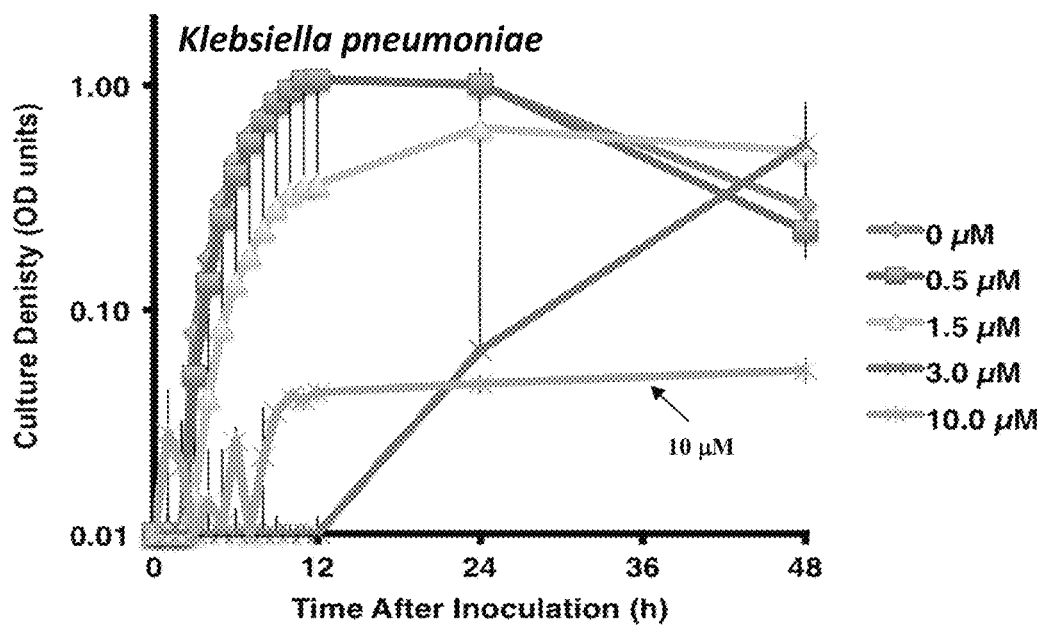
FIG. 20F is a growth curve in BHI culture for *K. pneumoniae* with one inoculation of liptin 3e.
Figure 20G:
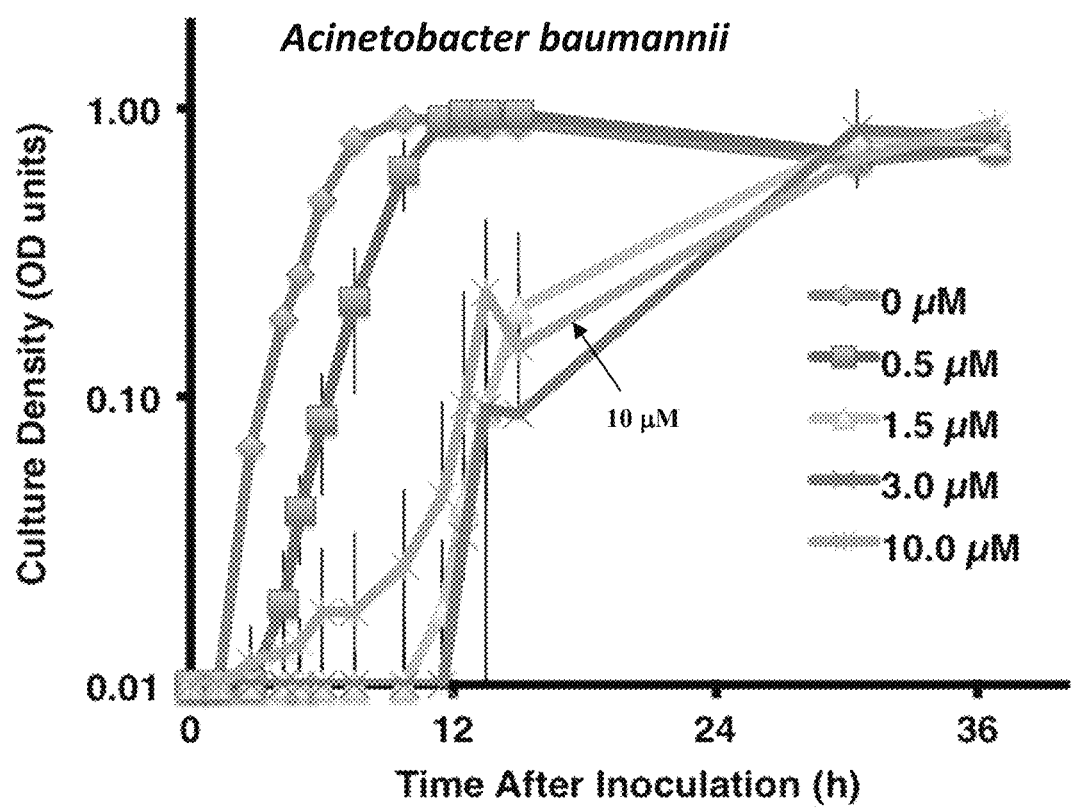
FIG. 20G is a growth curve in BHI culture for *A. baumannii* with one inoculation of liptin 3e.
Figure 20H:
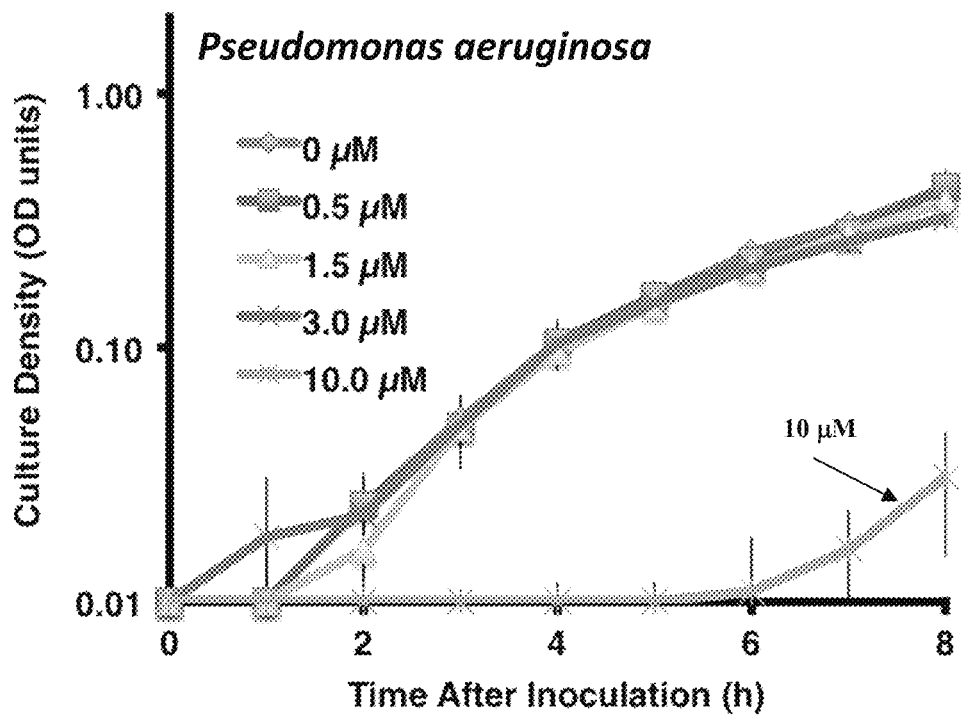
FIG. 20H is a growth curve in BHI culture for *P. aeruginosa* with one inoculation of liptin 3e.

Liptins 3f-h also cause membrane leakage when they bind to PG in a membrane, as evidenced by the efflux of fluorescent carboxy-fluorescein from model lipid vesicles of 80% PE/20% PG (the lipid content models *E. coli*'s plasma membrane), shown in FIG. 19B. The circle bottom line data set is the control without liptin. The triangle second to bottom line data set shows data for 1.5 µM liptin 3f. The diamond second to top line data set shows the data for 1.5 liptin 3h. The square top line data set shows data for 1.5 µM liptin 3g. Y-axis: % Efflux; X-axis: Time in minutes.

While the efflux caused by liptin 3e at 2.5 µM concentration resulted in approximately 5-10% dye leakage after 90 minutes, the porphyrins with extended pickets above the ammonium functionality, either propyl (3g) or hexyl (3h) groups, cause 60-80% dye leakage quickly after addition of the liptin to the liposomes at 1.5 µM concentration. Dynamic light scattering of the treated liposomes show that they are still extant, and leakage is not a result of dissolution of the synthetic vesicle. This greater efflux activity may well translate to lower MICs of these two compounds relative to liptin 3e, and may well change the liptin activity from bacteriostatic to bactericidal. The benzyl extension of the porphyrin's pickets above the ammonium functional groups does not lead to dye leakage, perhaps because it is unable to bind to the model membrane due to steric constraints of the larger pickets.

Liptins 1h-k causes membrane leakage as evidenced by the efflux of fluorescent carboxy-fluorescein from model lipid vesicles of 80% PE/20% PG (the lipid content models *E. coli*'s plasma membrane), as shown in FIGS. 19C-F. In all graphs the positive control bee AMP melittin, which forms pores in membranes at 2.5 µM concentrations, results in 100% loss of dye as shown in graphs below (efflux shown on Y-axis on right side). Liptins 1h-k when bound to model membrane cause dye leakage of 10-20% over ninety minutes. This strongly suggest that the liptins, unlike melittin, are not forming pores, but rather making the membrane more permeable to dye leakage.

New Growth Curves for several bacteria in BHI (brain-heart-infusion) culture media show liptin 3e to be highly bacteriostatic.

Growth curves were generated from liquid shake-flask cultures using absorbance measurements at 600 nm at different concentrations of liptin 3e. The results are shown in FIGS. 20A-20H. Unnoculated control flasks were used as blanks. Absorbance values of 0.1 OD unit was considered reasonable threshold for positive growth. The use of the nutrient-rich BHI culture allowed us to measure the effects of liptin 3e on bacterial growth rates over long periods of time, which showed that liptin 3e is more bacteriostatic with Gram-positive than Gram-negative bacteria. Liptin exposure appears to stop bacterial growth, as evidenced by long lag phases, which increase with liptin concentration. In most cases, cultures recover, but growth rates and maximum cell densities are decreased with liptin treatment. Gram-positive, Gram-negative, and Mycobacteria were all inhibited by liptin 3e with one inoculation, demonstrating the liptin's highly bacteriostatic activity.

Liptin 3e reduces bacterial growth rates.

Figure 21:
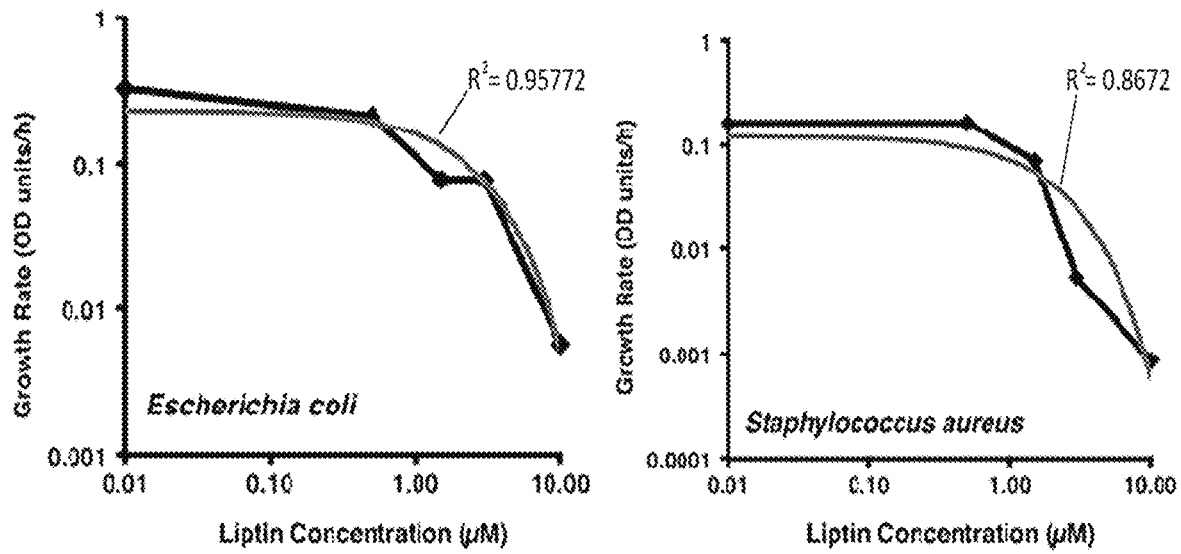
FIG. 21 is a graph that shows the reduction of growth rate of *E. coli* and *S. aureus* with one inoculation of liptin 3e in a concentration-dependent manner.

Bacterial growth rates were reduced by liptin 3e treatment in a concentration-dependent manner. The data is shown in FIG. 21. Rates were determined as the slope of the log phase of the growth curve, after the lag phase. An exponential relationship exists with marginally significant differences ($p<0.1$).

Liptin 3e decreases maximum culture density.

Figure 22:
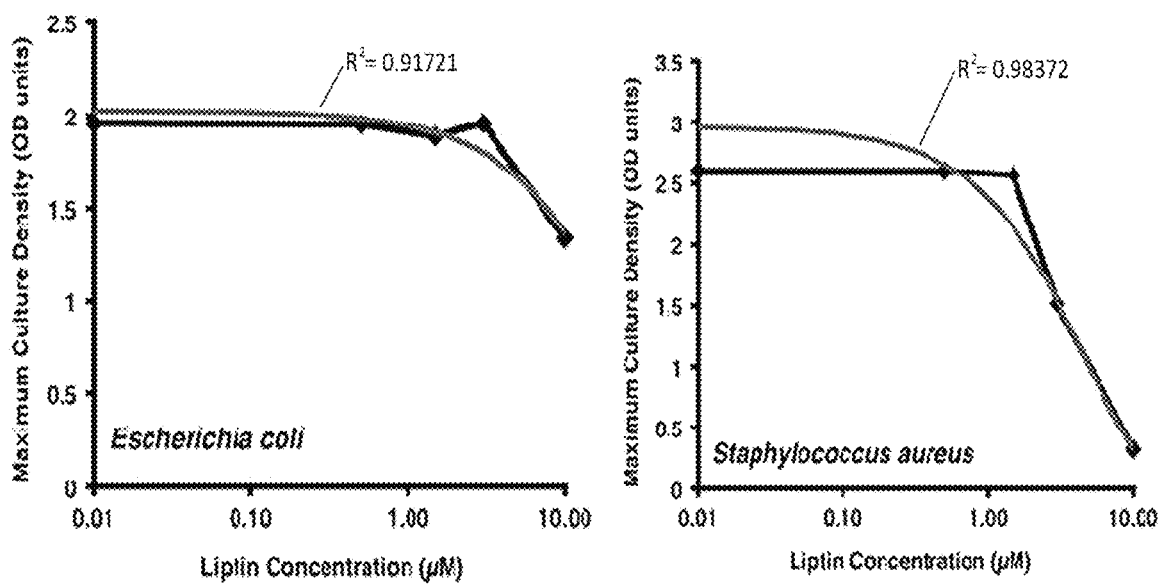
FIG. 22 is a graph that shows the decrease in culture density of *E. coli* and *S. aureus* with one inoculation of liptin 3e in a concentration-dependent manner.

The highest culture densities observed were marginally significantly correlated ($p<0.1$) to liptin 3e concentration. Maximum culture densities represent the carrying capacity of a culture flask. As shown in FIG. 22, cells grow less robustly while using energy to resist environmental insult (liptin), and hence reach lower final culture densities before the medium is expended.

Minimum Inhibitory Concentration (MIC) Determinations in Muller Hinton Culture Media and Growth Curves for Bacteria in BHI (Brain-Heart-Infusion) Culture Media Show that Minor Structural Changes in Liptins 1h-k Modulates their Antibacterial Activity.

MICs were determined in cation-adjusted Muller Hinton culture. Standard CLSI protocol for serial dilutions of liptin concentrations were used to determine the MIC, starting at 0.01 OD. Two different experimental cultures were used and each data point measured in triplicate. The liptin concentrations that show no growth after 24 hours are shown in the table below.

TABLE 3

| | MIC ($\mu$M) | | | |
|---|---|---|---|---|
| Bacteria | Liptin 1j | Liptin 1i | Liptin 1h | Liptin 1k |
| Escherichia coli | 3.5 | 3 | 2 | 1.5 |
| Staphylococcus aureus | 4 | 3 | 2.5 | 2 |
| MRSA | 4.5 | 3.5 | 3 | 2.5 |
| Mycobacterium smegmatis | 3.5 | 3 | 2.5 | 2 |
| Pseudomonas aeruginosa | 14 | 12 | 9 | 8 |
| Klebsiella pneumoniae | 3.5 | 4 | 3 | 2.5 |
| Acinetobacter baumannii | 4 | 3.5 | 2.5 | 2 |

Growth curves in BHI culture were generated (not shown) from liquid shake-flask cultures using absorbance measurements at 600 nm at different concentrations of liptins 1h-k. Uninoculated control flasks were used as blanks. Absorbance values of 0.1 OD unit was considered reasonable threshold for positive growth. The use of the nutrient-rich BHI culture allowed us to measure the effects of the small structural differences in liptins 1h-k on bacterial growth rates over long periods of time. The growth curves showed that the liptins are bactericidal, and that liptins 1h and 1k were the most potent with Gram-positive and Gram-negative bacteria. Liptin exposure appears to stop bacterial growth, as evidenced by long lag phases, which increase with liptin concentration, and growth rates and maximum cell densities are decreased with liptin treatment. Most Gram-positive and Gram-negative bacteria were all killed or greatly slowed in growth by liptins 1h and 1k with one inoculation in BHI culture, demonstrating the liptin's highly bactericidal activity. Liptins 1h-k showed high bacteriostatic effects with *Pseudomonas aeruginosa* in BHI culture but not bactericidal effects.

Minimum Bactericidal Concentration (MBC) Determination.

Minimum bactericidal concentration (MBC) were determined in cation-adjusted Muller Hinton culture. Standard CLSI protocol for serial dilutions of liptin concentrations were used to determine the MBC, starting at 0.01 OD. Two different experimental cultures were used and each data point measured in triplicate. *P. aeruginosa* did not exhibit MBC below 20 $\mu$M liptin concentration.

The MBC for liptins 1h-k was determined. The results are shown below.

TABLE 4

| | MBC ($\mu$M) | | | |
|---|---|---|---|---|
| Bacteria | Liptin 1j | Liptin 1i | Liptin 1h | Liptin 1k |
| Escherichia coli | 15 | 14 | 9 | 7.5 |
| Staphylococcus aureus | 15.5 | 10.5 | 11 | 9.5 |
| MRSA | 15 | 11.5 | 10 | 11.5 |
| Mycobacterium smegmatis | 12 | 10.5 | 11.5 | 9.5 |

TABLE 4-continued

| | MBC ($\mu$M) | | | |
|---|---|---|---|---|
| Bacteria | Liptin 1j | Liptin 1i | Liptin 1h | Liptin 1k |
| Pseudomonas aeruginosa | n/a | n/a | n/a | n/a |
| Klebsiella pneumoniae | 13 | 12 | 8.5 | 9.5 |
| Acinetobacter baumannii | 12.5 | 11.5 | 8.5 | 7.5 |

As can be seen from the data in the table above, the MBCs for these liptins are roughly 4-5 times the concentrations of their respective MICs, and are therefore mostly bactericidal.

Live-Dead stains for bacteria inoculated with liptins 1h and 1k.

Molecular Probes BacLight© kits containing the SYTO 9 green-fluorescent dye and propidium iodide red-fluorescent dye were used to detect live or dead bacteria after ninety minute exposure of bacteria to liptins 1h or 1k. Bacteria in Muller Hinton culture were grown to an OD=0.3, were inoculated with liptins 1h and 1k and after ninety minutes stained with a mixture of the above dyes and affixed to a slide to be examined under a light microscope (40×) to determine the number of live and dead cells (green colored cells considered alive and red-colored cells considered dead). Data was calculated based upon an average of 5 different plate counts from each slide, and is based on a percent of total bacteria counted (live and dead). Control sample contains no liptin. The results presented demonstrate the potent bactericidal efficacy of liptins after bacteria have been exposed to either 5 or 10 $\mu$M liptin for only 90 minutes after one inoculation.

TABLE 5

| | Live-Dead Stains | | | | | |
|---|---|---|---|---|---|---|
| | Liptin 1h | | Liptin 1k | | Control | |
| Bacteria | Live | Dead | Live | Dead | Live | Dead |
| Escherichia coli (10 $\mu$M) | 35% | 75% | 35% | 65% | 100% | 0 |
| Staphylococcus aureus (5 $\mu$M) | 61% | 39% | 58% | 42% | 97% | 3% |
| MRSA (5 $\mu$M) | 28% | 72% | 30% | 70% | 98% | 2% |
| MRSA (10 $\mu$M) | 15% | 84% | 0 | 100% | | |
| Mycobacterium smegmatis (5 $\mu$M) | 7% | 93% | 0 | 100% | 100% | 0 |
| Klebsiella pneumoniae (5 $\mu$M) | 33% | 67% | 0 | 100% | 86% | 14% |
| Klebsiella pneumoniae (10 $\mu$M) | 0 | 100% | na | na | — | — |
| Acinetobacter baumannii (5 $\mu$M) | 12% | 88% | 3% | 97% | 95% | 5% |

Plasma membrane depolarization as mechanism of bactericidal action of liptins 1h and 1k.

Figure 23A:
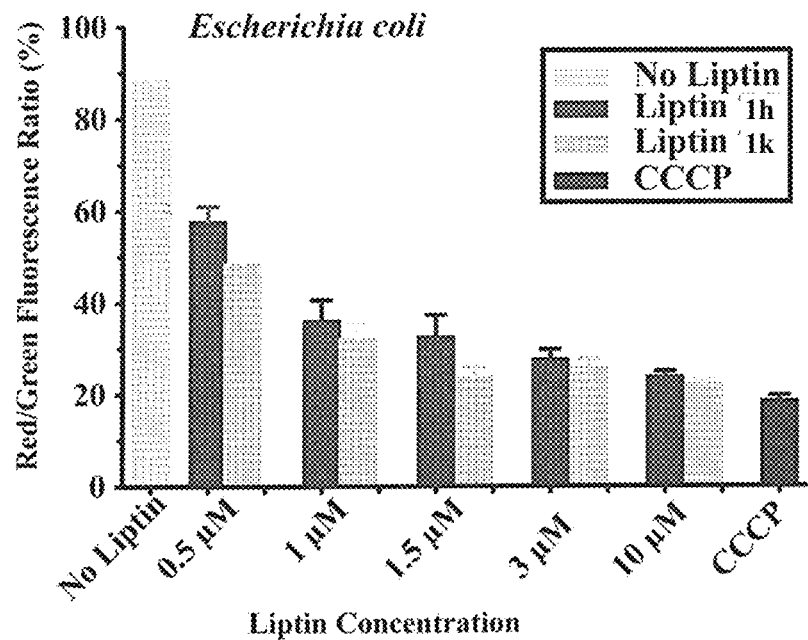
FIG. 23A is a graph depicting the plasma membrane depolarization in *E. coli* caused by liptins 1h and 1k in a concentration-dependent manner.
Figure 23B:
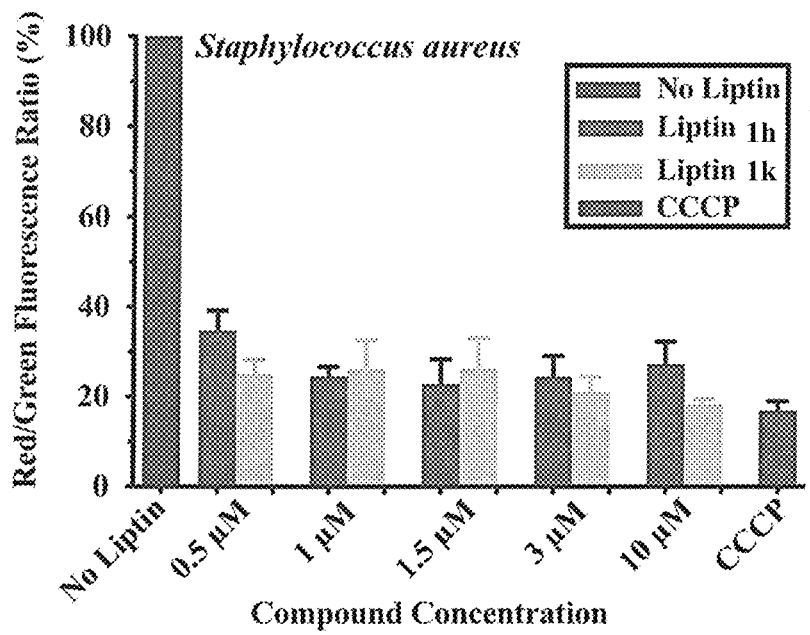
FIG. 23B is a graph depicting the plasma membrane depolarization in *S. aureus* caused by liptins 1h and 1k in a concentration-dependent manner.

The Molecular Probes BacLight® Bacterial Membrane Potential kit was used to detect changes in the polarization of the bacterial plasma membrane upon inoculation of bacteria with varying concentrations of liptins 1h or 1k. The dye 3,3-diethyloxacarbocyanine iodide exhibits either green or red fluorescence depending on the membrane potential, and the graph is a ratio of red (high membrane potential) to green (low membrane potential) fluorescence. CCCP (carbonyl cyanide 3-chlorophenylhydrazone) is a proton ionophore that destroys plasma membrane potential and as such is a positive control. The results in FIGS. 23A and 23B show that both a Gram-positive and Gram-negative bacteria exhibit large membrane depolarization when the bacteria are exposed to one half than the liptins' MICs, and the loss of membrane potential is concentration dependent. With plasma membrane depolarization the bacterial cell loses its ability to synthesize ATP and proteins. Additionally loss of membrane potential stops the ability for cell replication due to an inability for proper placement of divisome proteins in the plasma membrane. While this may be a result of plasma membrane cation leakage, as stated above the liptins do not appear to make pores in the membrane. Thus, it is possible that the liptin's mechanism of action is a result of their deleterious effect on the functioning of electron transport proteins found in the plasma membrane.

Scanning Electron Microscopy.

Figure 24:
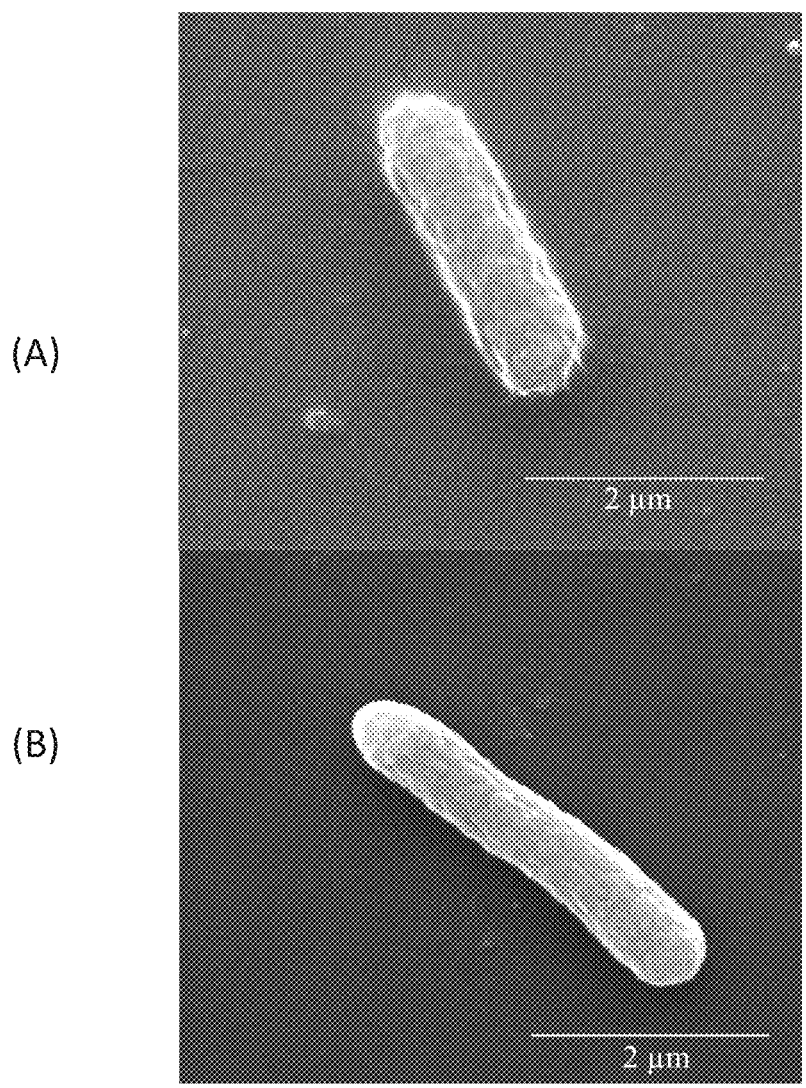
FIG. 24 shows scanning electron micrographs (SEM) of (A) treated and (B) untreated *E. coli* cells with 5 µM liptin 1k, evidencing a clear stunting of growth but no holes in the outer membrane.

FIG. 24 shows a comparison of scanning electron micrographs of *E. coli* (A) treated or (B) untreated with 5 μM of liptin 1k. The images are to the same scale. There is a clear stunting of growth in the *E. coli* that was exposed to the liptin. There also seems to be a wrinkling of the outer membrane of the *E. coli* exposed to liptin 1k as opposed to a smoother outer membrane in the unexposed bacterial cell. Importantly, no hole or apparent destruction of the outer membrane is seen in the liptin-exposed bacterial cell.

Figure 25:
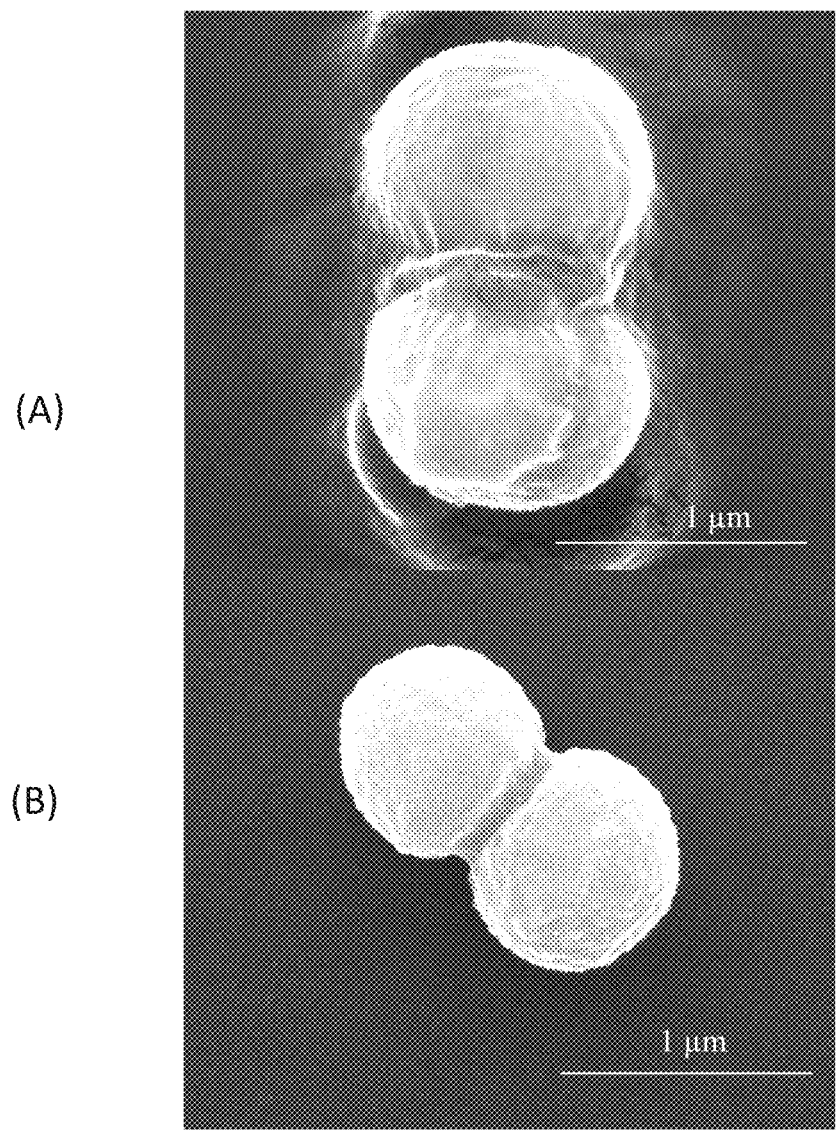
FIG. 25 shows scanning electron micrographs (SEM) of (A) treated and (B) untreated MRSA cells with 5 µM liptin 1k, evidencing a wrinkling or non-uniformity of the outer membrane of the MRSA exposed to liptin 1k.

FIG. 25 shows a comparison of SEM images of MRSA (A) treated or (B) untreated with 5 of liptin 1k. The images are to the same scale. There appears to be a wrinkling or non-uniformity of the outer membrane of the MRSA exposed to liptin 1k as opposed to a smoother outer membrane in the unexposed bacterial cell. Importantly, no hole or apparent destruction of the outer membrane is seen in the liptin-exposed bacterial cells. The liptin treated MRSA cells also appear to be somewhat desiccated compared to those that are untreated.

Figure 26:
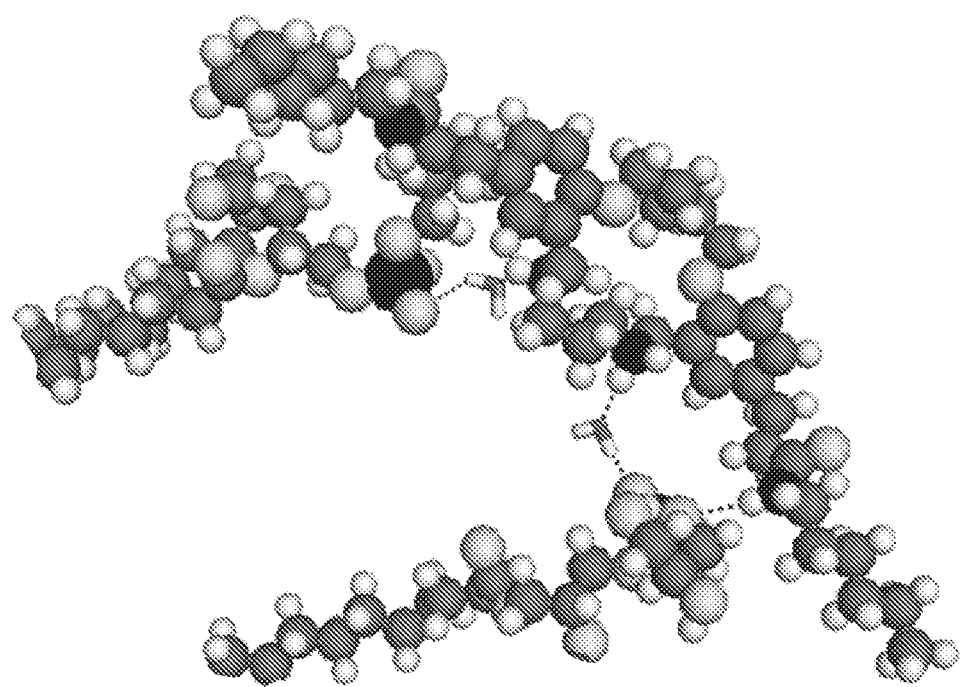
FIG. 26 depicts the molecular dynamics simulation of how liptin 1h binds to PG in a membrane.

Molecular Dynamics (MD) of Liptin 1h Binding to Two PG Lipid Head Groups in Lipid Patch FIG. 26 shows an MD simulation of the binding of the liptin 1h to two PG head groups, showing multiple hydrogen bonding interactions between the lipid head group and liptin. Only two lipids, hydrogen-bound water molecules, and liptin 1h shown—patch lipids and other waters removed for purposes of clarity. The simulation was run with six liptin 1h molecules (10 mM) in aqueous solution above an equilibrated lipid membrane of 80:20 DPPE:DPPG (DP=Dipalmitoyl) with 52 DPPE and 13 DPPG per side in explicit water. Binding occurs within 20 ns, with no input to steer liptin toward PG lipid head group. Unlike liptin 3e, which binds to one PG lipid head group, the liptin 1h is seen interaction with two PG lipid head groups. One head group exhibits hydrogen bonding to the liptin's para amide functionality as well as the ammonium hydrogen via an interceding water molecule, both bound to the lipid's phosphorus negatively charged oxygen. The other ammonium hydrogen is also hydrogen bound to the second PG lipid head group via an interceding water molecule to the phosphorus oxygen that is negatively charged.

Example 7

Initial Toxicity Study

Toxicity Studies of human HeLa (vaginal carcinoma) and A549 (lung carcinoma epithelial) cells with Liptins 1h and 1k.

Eukaryote cell toxicity was determined using a Pierce LDH assay kit including the Chemical Compound-Mediated Cytotoxicity assay. This kit measures cell death by measuring the amount of lactate dehydrogenase released from cells. Lactate dehydrogenase (LDH) is a cytosolic enzyme present in many different types of cells. When the plasma membrane is damaged, LDH is released into cell culture media. The released LDH can be quantified by a coupled enzymatic reaction. First, LDH catalyzes the conversion of lactate to pyruvate via reduction of NAD+ to NADH. Second, diaphorase uses NADH to reduce a tetrazolium salt (INT) to a red formazan product. Therefore, the level of formazan formation is directly proportional to the amount of released LDH in the medium.

Figure 27:
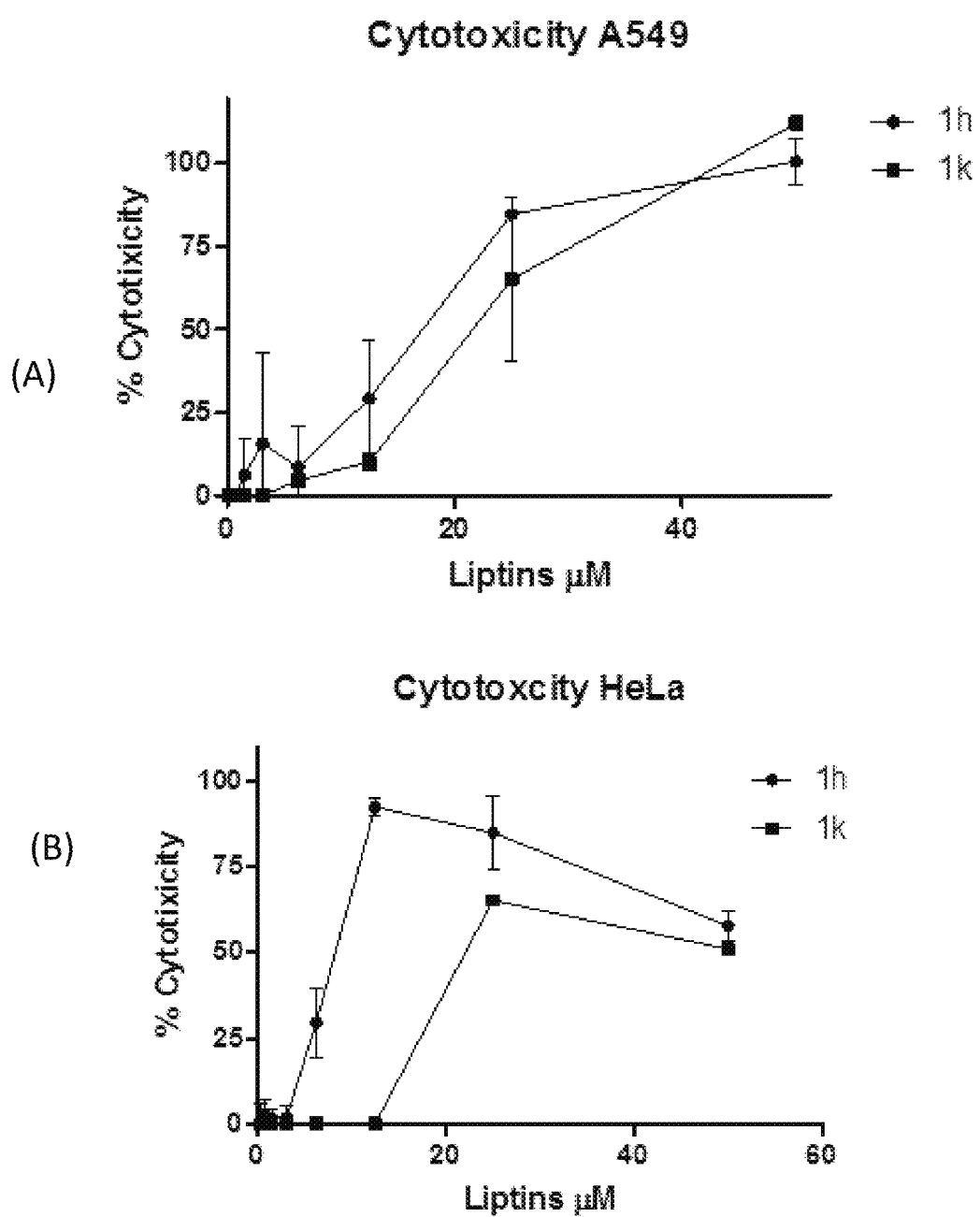
FIG. 27 details toxicity studies of liptins 1h and 1k with eukaryotic cell lines HeLa and A459.

The results are shown in FIG. 27. With both cell lines the toxicity associated with liptin 1h was substantially greater than that observed with liptin 1k. For example, with HeLa cells there is no cell toxicity observed up to about 15 μM with liptin 1k, where there is large toxicity with liptin 1h at that concentration. With the A549 lung epithelial cells the toxicity near 15 μM liptin 1k is around 8%, whereas with liptin 1h the cytotoxicity of the lung cells was over 25%. The MICs of 1k determined for the 6 bacteria stated above was measured at 1.5-2.5 μM liptin, thus there is no measured cytotoxicity observed in the two cells lines between 5-10 times the concentrations of 1k's MICs.

The invention claimed is:

1. An antibacterial small molecule compound that binds to phosphatidylglycerol in bacterial plasma membranes, said small molecule comprising a central scaffold and a plurality of functional groups cooperatively forming a three-dimensional complementary binding pocket for said phosphatidylglycerol, wherein said compound is selected from the group consisting of 1h, 1i, 1j, and 1k of the formula:

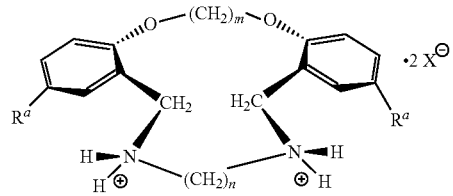

1h: m is 5, n is 3, and each $R^a$ is —$(CH_2)_2CONHC_6H_{13}$,
1i: m is 4, n is 3, and each $R^a$ is —$(CH_2)_2CONHC_6H_{13}$,
1j: m is 4, n is 4, and each $R^a$ is —$(CH_2)_2CONHC_6H_{13}$,
1k: m is 4, n is 4, each $R^a$ is —$CH_2CONHC_6H_{13}$,
where $X^-$ is any anionic counter ion.

2. The compound of claim 1, wherein said compound is bacteriostatic.

3. The compound of claim 1, wherein said compound is bactericidal.

4. An antibacterial composition comprising a bacteriostatic or bactericidal amount of an antibacterial small molecule compound according to claim 1 dispersed in a pharmaceutically-acceptable carrier.

5. The composition of claim 4, wherein said carrier is selected from the group consisting of saline, buffered saline, sterile water, aqueous dextrose solutions, aqueous glycerol solutions, ethanol, allantoic fluid, oil-in-water emulsion, water-in-oil emulsions, dimethyl sulfoxide, petroleum jelly, cocoa butter, cottonseed oil, olive oil, sodium pyruvate, vitamin E, white petrolatum, white wax, stearyl alcohol, cholesterol, mineral oil, ceryl ester wax, sodium lauryl sulfate, propylene glycol, polyethylene glycol, and mixtures thereof.

6. The composition of claim 4, said composition being substantially free of antibiotics and/or antimicrobial peptides.

7. The composition of claim 4, said composition consisting essentially of said small molecule compound and said carrier.

8. The composition of claim 4, said compound has a minimum inhibitory concentration (MIC) of from about 1 to about 4 µM.

* * * * *